(12) United States Patent
Kato et al.

(10) Patent No.: US 8,792,975 B2
(45) Date of Patent: Jul. 29, 2014

(54) ELECTROENCEPHALOGRAM MEASUREMENT APPARATUS, METHOD OF ESTIMATING ELECTRICAL NOISE, AND COMPUTER PROGRAM FOR EXECUTING METHOD OF ESTIMATING ELECTRICAL NOISE

(75) Inventors: Yumiko Kato, Osaka (JP); Shinobu Adachi, Nara (JP); Yoshihisa Terada, Tokyo (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 263 days.

(21) Appl. No.: 13/408,091

(22) Filed: Feb. 29, 2012

(65) Prior Publication Data

US 2012/0172744 A1 Jul. 5, 2012

Related U.S. Application Data

(63) Continuation of application No. PCT/JP2011/002189, filed on Apr. 13, 2011.

(30) Foreign Application Priority Data

Apr. 28, 2010 (JP) .................................. 2010-103144

(51) Int. Cl.
*A61B 5/04* (2006.01)

(52) U.S. Cl.
USPC .......................... 600/544; 381/71.6; 381/94.1

(58) Field of Classification Search
USPC .......................... 600/544, 545; 381/71.6, 94.1
See application file for complete search history.

(56) References Cited

U.S. PATENT DOCUMENTS

| | | | | |
|---|---|---|---|---|
| 5,170,434 | A * | 12/1992 | Anderson | 381/317 |
| 6,349,231 | B1 | 2/2002 | Musha | |
| 7,133,715 | B1 * | 11/2006 | Smits et al. | 600/544 |
| 2003/0073920 | A1 * | 4/2003 | Smits et al. | 600/544 |
| 2007/0003083 | A1 * | 1/2007 | Rikimaru | 381/312 |

FOREIGN PATENT DOCUMENTS

| | | |
|---|---|---|
| JP | 02-068035 A | 3/1990 |
| JP | 05-293172 A | 11/1993 |
| JP | 06-030908 A | 2/1994 |
| JP | 07-204168 A | 8/1995 |

(Continued)

OTHER PUBLICATIONS

International Search Report for corresponding International Application No. PCT/JP2011/002189 mailed May 24, 2011.

*Primary Examiner* — Navin Natnithithadha
*Assistant Examiner* — Etsub Berhanu
(74) *Attorney, Agent, or Firm* — Renner, Otto, Boisselle & Sklar, LLP

(57) ABSTRACT

An electroencephalogram measurement apparatus includes: an electroencephalogram measurement section for measuring an electroencephalogram of a user by using a plurality of electrodes; an electro-acoustic transducer for presenting an acoustic signal to the user, the electro-acoustic transducer being in a vicinity of at least one electrode among the plurality of electrodes while the electroencephalogram measurement section is worn by the user; an amplitude envelope extraction section for extracting an amplitude envelope of the acoustic signal presented by the electro-acoustic transducer; a frequency analysis section for applying a frequency analysis to the amplitude envelope extracted by the amplitude envelope extraction section; and a noise estimation section for estimating an electrical noise which is mixed at the at least one electrode by using a previously provided set of transform rules and the extracted amplitude envelope.

26 Claims, 38 Drawing Sheets

(56) References Cited

FOREIGN PATENT DOCUMENTS

| | | |
|---|---|---|
| JP | 09-131331 A | 5/1997 |
| JP | 2001-061800 A | 5/2001 |
| JP | 2001-187034 A | 7/2001 |
| JP | 2002-017697 A | 1/2002 |
| JP | 2005-034620 A | 2/2005 |
| JP | 2010-082375 A | 4/2010 |
| WO | 03/032811 A2 | 4/2003 |

* cited by examiner

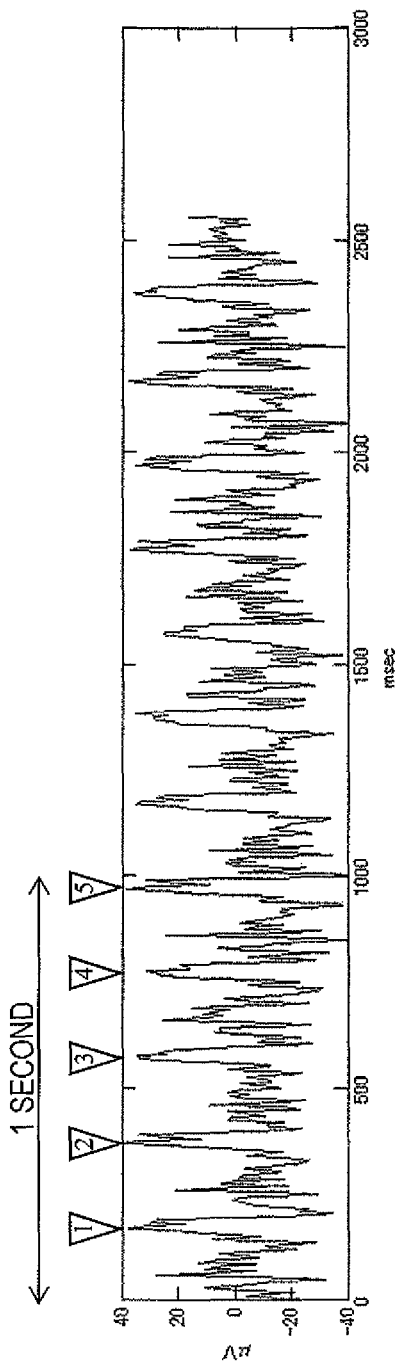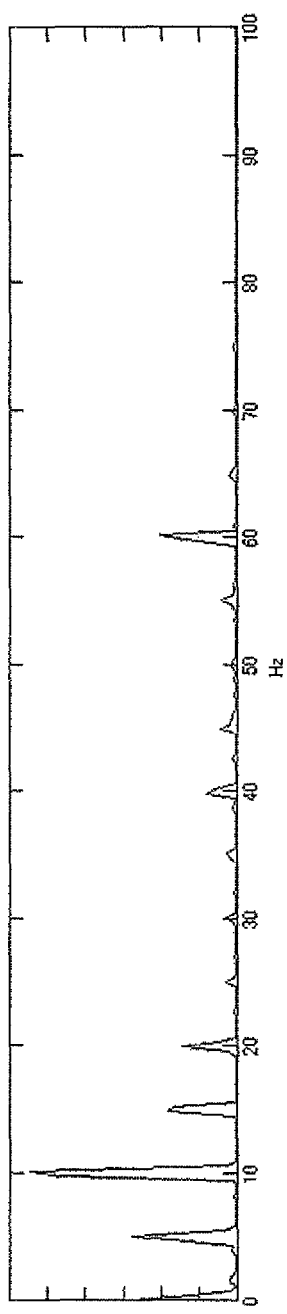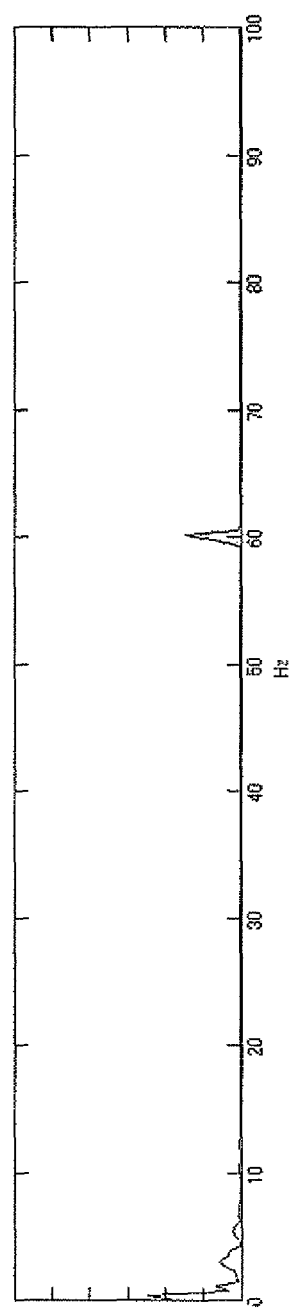
FIG.2A
FIG.2B
FIG.2C

1170ms

ENVELOPE

1200ms

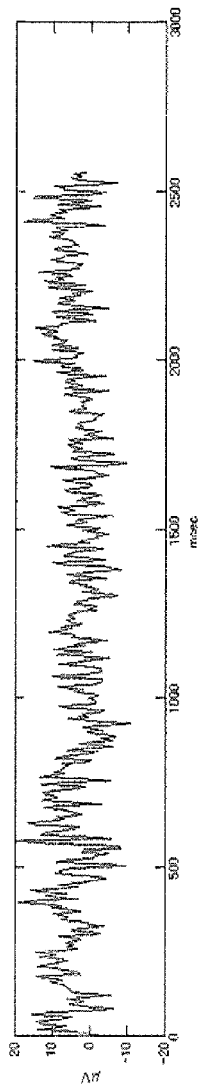
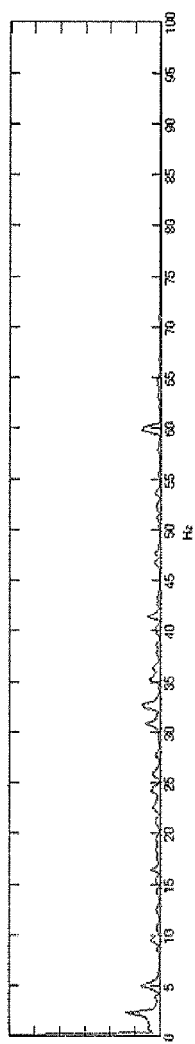
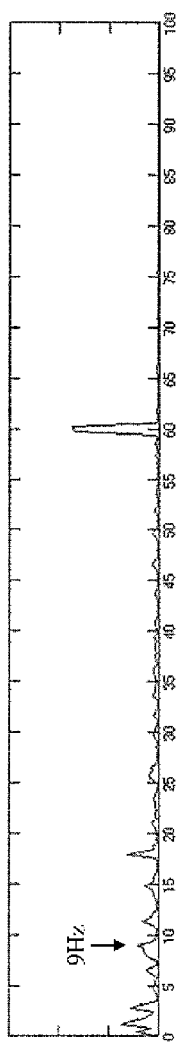
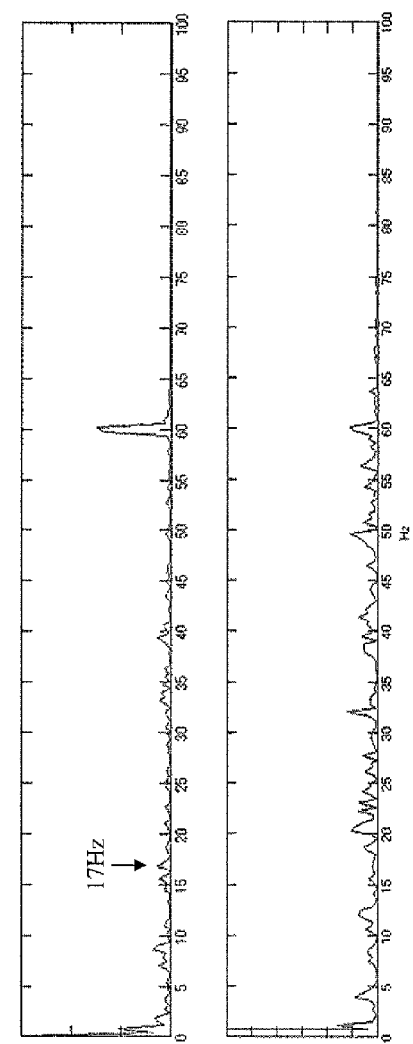
FIG. 4A
FIG. 4B
FIG. 4C
FIG. 4D
FIG. 4E

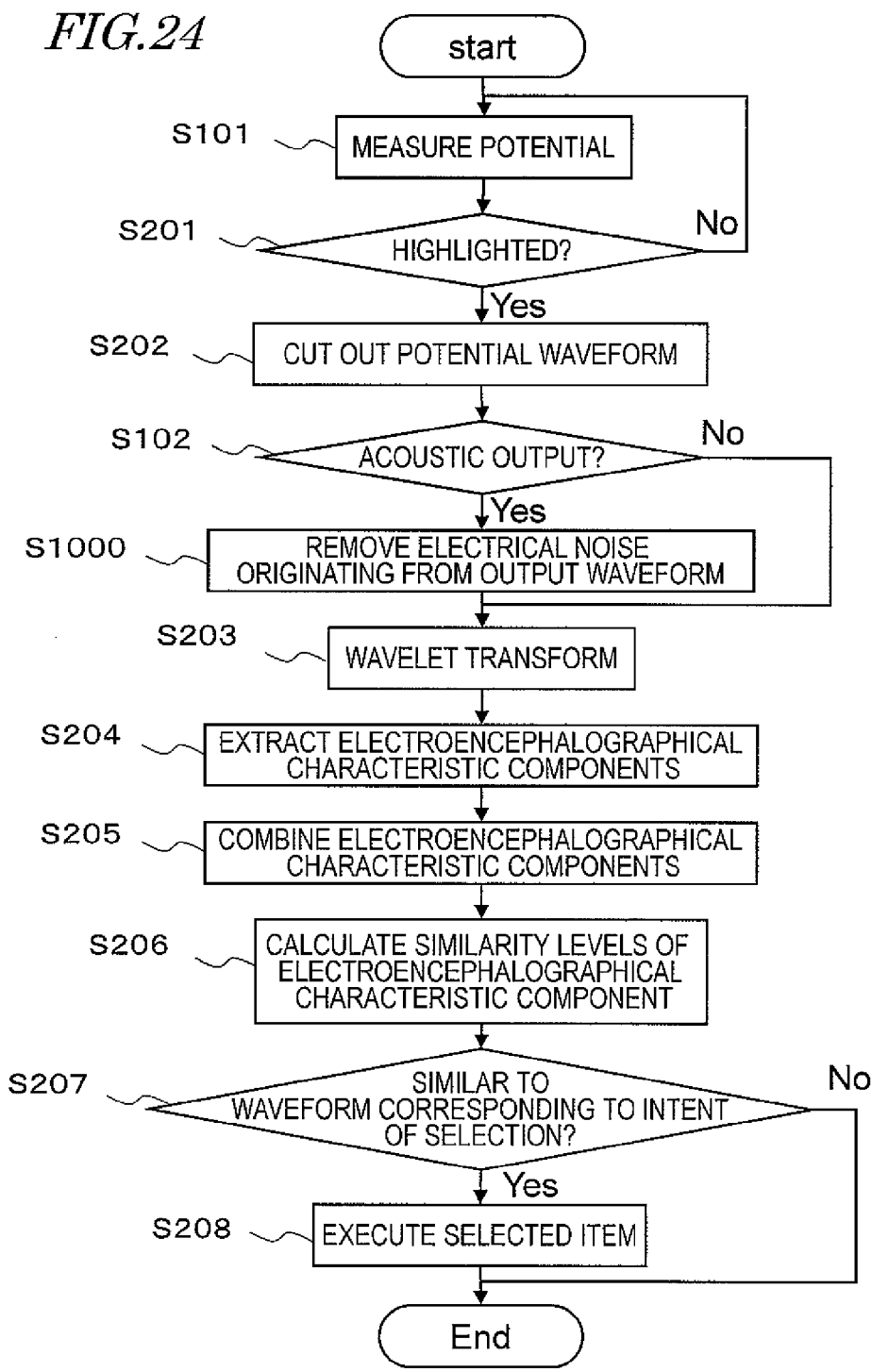

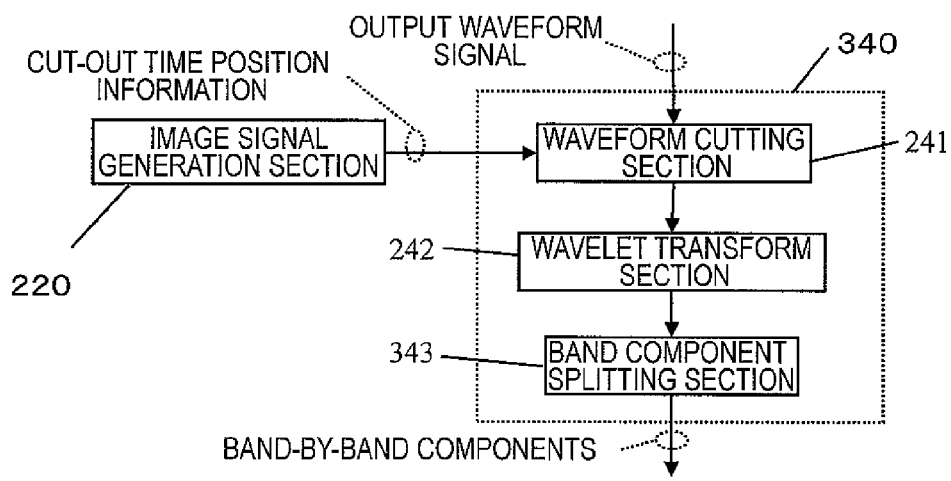
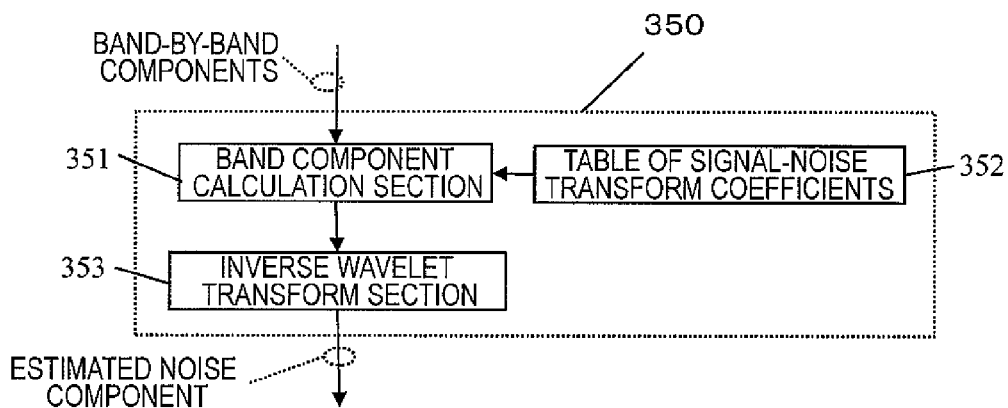

| | | BAND COMPONENT POWER OF OUTPUT WAVEFORM | | | |
|---|---|---|---|---|---|
| | | LESS THAN 10dB | LESS THAN 20dB | LESS THAN 30dB | 30dB OR MORE |
| BAND | 0Hz~2Hz | 0.0 | 0.05 | 0.08 | 0.15 |
| | 2Hz~4Hz | 0.0 | 0.05 | 0.12 | 0.20 |
| | 4Hz~8Hz | 0.0 | 0.05 | 0.12 | 0.18 |
| | 8Hz~16Hz | 0.0 | 0.02 | 0.08 | 0.15 |
| | 16Hz~32Hz | 0.0 | 0.0 | 0.0 | 0.05 |

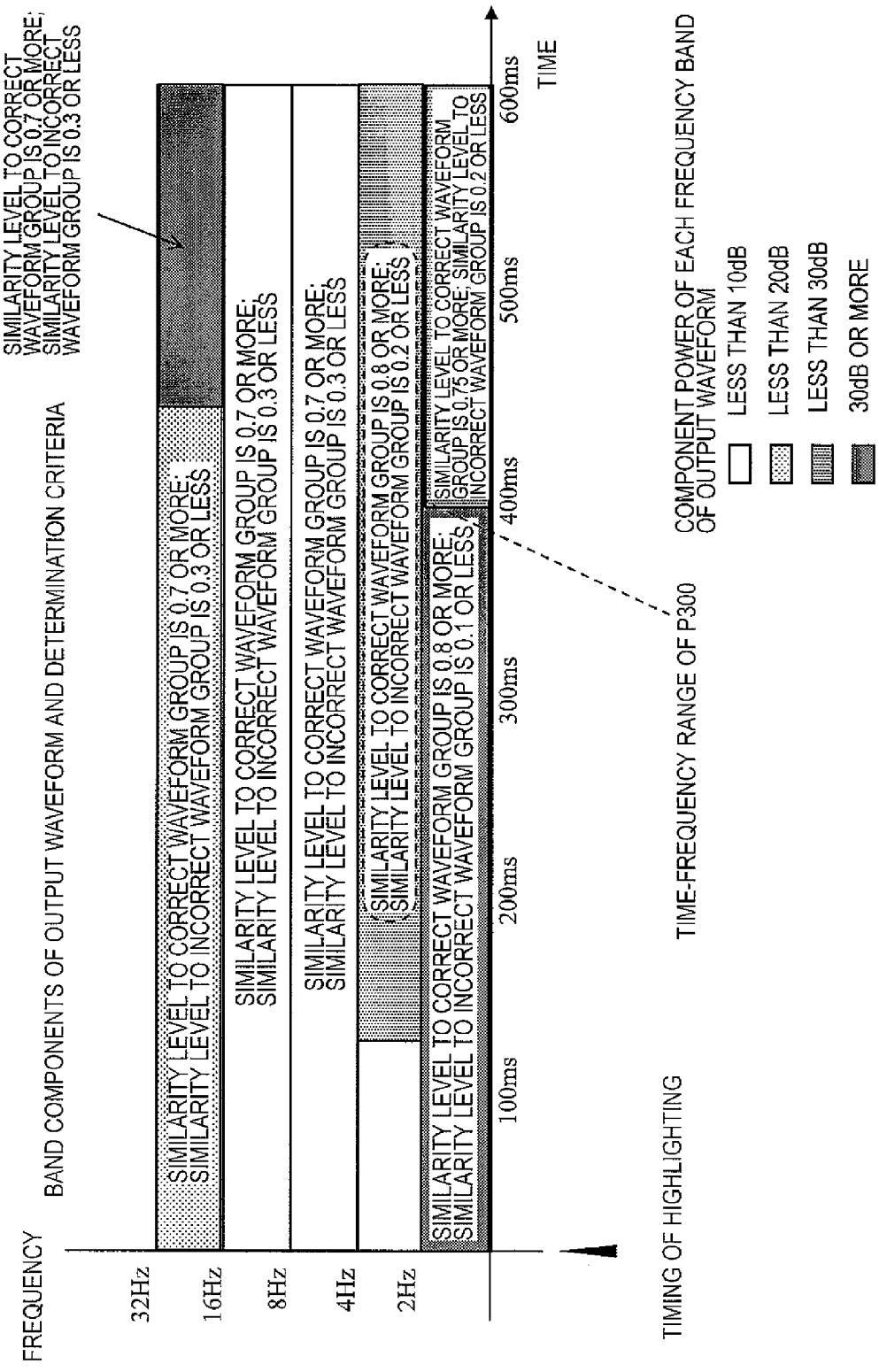

FIG.39

| BAND | | BAND COMPONENT POWER OF OUTPUT WAVEFORM | | | |
|---|---|---|---|---|---|
| | | LESS THAN 10dB | LESS THAN 20dB | LESS THAN 30dB | 30dB OR MORE |
| 0Hz~2Hz | LOWER LIMIT OF SIMILARITY LEVEL TO CORRECT WAVEFORM GROUP | 0.7 | 0.7 | 0.75 | 0.8 |
| | UPPER LIMIT OF SIMILARITY LEVEL TO INCORRECT WAVEFORM GROUP | 0.3 | 0.2 | 0.2 | 0.2 |
| 2Hz~4Hz | LOWER LIMIT OF SIMILARITY LEVEL TO CORRECT WAVEFORM GROUP | 0.7 | 0.75 | 0.8 | 0.8 |
| | UPPER LIMIT OF SIMILARITY LEVEL TO INCORRECT WAVEFORM GROUP | 0.3 | 0.2 | 0.2 | 0.1 |
| 4Hz~8Hz | LOWER LIMIT OF SIMILARITY LEVEL TO CORRECT WAVEFORM GROUP | 0.7 | 0.7 | 0.7 | 0.75 |
| | UPPER LIMIT OF SIMILARITY LEVEL TO INCORRECT WAVEFORM GROUP | 0.3 | 0.2 | 0.2 | 0.2 |
| 8Hz~16Hz | LOWER LIMIT OF SIMILARITY LEVEL TO CORRECT WAVEFORM GROUP | 0.7 | 0.7 | 0.7 | 0.7 |
| | UPPER LIMIT OF SIMILARITY LEVEL TO INCORRECT WAVEFORM GROUP | 0.3 | 0.3 | 0.2 | 0.2 |
| 16Hz~32Hz | LOWER LIMIT OF SIMILARITY LEVEL TO CORRECT WAVEFORM GROUP | 0.7 | 0.3 | 0.3 | 0.3 |
| | UPPER LIMIT OF SIMILARITY LEVEL TO INCORRECT WAVEFORM GROUP | 0.3 | 0.3 | 0.3 | 0.3 |

FIG.45

| NOISE AMPLITUDE | DETERMINATION CRITERION ||
| --- | --- | --- |
| | LOWER LIMIT OF SIMILARITY LEVEL TO CORRECT WAVEFORM GROUP | UPPER LIMIT OF SIMILARITY LEVEL TO INCORRECT WAVEFORM GROUP |
| ~1μV | 80% | 20% |
| 1μV~3μV | 70% | 20% |
| 3μV~7μV | 70% | 40% |
| 7μV~ | AVOID DETERMINATION ||

FIG.49

| NOISE AMPLITUDE | AMOUNT OF INCREASE IN NOISE AMPLITUDE | RATE OF CHANGE IN CRITERION OF α WAVE INCREASE/DECREASE DETERMINATION | |
|---|---|---|---|
| | | LOWER LIMIT OF AMOUNT OF INCREASE | LOWER LIMIT OF AMOUNT OF DECREASE |
| ~5μV | ~1μV | 0% | 0% |
| | 1μV~3μV | 20% | 10% |
| 5μV~ | ~1μV | 0% | 0% |
| | 1μV~3μV | 10% | 10% |
| | 3μV~5μV | 30% | 20% |
| | 5μV~ | AVOID DETERMINATION | |

ELECTROENCEPHALOGRAM MEASUREMENT APPARATUS, METHOD OF ESTIMATING ELECTRICAL NOISE, AND COMPUTER PROGRAM FOR EXECUTING METHOD OF ESTIMATING ELECTRICAL NOISE

This is a continuation of International Application No. PCT/JP2011/002189, with an international filing date of Apr. 13, 2011, which claims priority of Japanese Patent Application No. 2010-103144, filed on Apr. 28, 2010, the contents of which are hereby incorporated by reference.

BACKGROUND OF THE INVENTION

1. Field of the Invention

The present invention relates to a technique of reducing influences of acoustic signals in electroencephalogram measurement.

2. Description of the Related Art

In recent years, due to decreases in the size and weight of devices, wearable devices such as stereo headphone-type music players and head-mount displays (hereinafter also referred to as "HMDs") are gaining prevalence.

Usually, as an interface with which to manipulate a device, physical input manipulations using an input device have been employed, e.g., "pressing a button", "moving a cursor and making a confirmation", or "manipulating a mouse while watching a screen". However, if the aforementioned physical input manipulations are required when manipulating a device whose main body has a small size and which is characterized to be handsfree, e.g., an HMD, the handsfree feature will be undermined, thus being ineffective. Furthermore, in the case of manipulating a very small device such as a hearing aid, the operation buttons and/or dials will become very small, which will be inconvenient for frequent manipulations.

Therefore, an interface which utilizes an electroencephalogram, such that it can be easily manipulated by a mere thought of a user, will be convenient because physical manipulations are not required. What will be even more convenient to have is an ability to monitor the state (e.g., emotions) of a user by utilizing an electroencephalogram or the like of the user, and automatically control the mode, etc., of a device in accordance with the monitored state.

As used herein, an "electroencephalogram" refers to the electrical activities of cranial nerve cells (encephalic activities) which are measured based on a difference between the potential of a reference electrode which is placed on the head of a human and the potential of a measurement electrode, for example. It is known that an electroencephalogram represents encephalic activities.

In recent years, development efforts have been directed toward techniques which utilize an electroencephalogram. Japanese Laid-Open Patent Publication No. 2005-34620 discloses an interface which utilizes an electroencephalogram. This publication discloses a technique of determining an option which a user wishes to select, by using a characteristic signal of the electroencephalogram called an event-related potential. Japanese Laid-Open Patent Publication No. 7-204168 discloses a technique which determines an emotional state based on an electroencephalogram and renders it into a numerical representation.

Conventionally, an electroencephalogram has been measured with electrodes being worn according to the position notation of the International 10-20 system. For example, the measurement electrode has been worn at the parietal. In Japanese Laid-Open Patent Publication No. 2005-34620, supra, electroencephalogram measurements are taken at the Pz and Cz positions according to the International 10-20 system. In Japanese Laid-Open Patent Publication No. 7-204168, supra, electroencephalogram measurements are taken at positions centered around the occiput in the neighborhood of Pz. This publication utilizes α waves, i.e., electroencephalograms in a band from 8 to 13 Hz, which are known to be recordable with a relatively large amplitude.

However, having to wear any electrodes for electroencephalogram measurement at the parietal or the occiput, other than at the portions where a wearable device (e.g., an HMO, a music player, and a hearing aid; the same notion will similarly apply hereinafter) would come in contact with the body, will present a burden on the user engaging or disengaging it, and cause discomfort or the like due to the fact that they are always worn on the scalp.

Therefore, it is necessary to accommodate the electrodes for electroencephalogram measurement within the range which is occupied by a shape that is usually needed by conventional wearable devices, so that the electrode placement is completed as soon as the wearable device is worn, thus reducing the burden of the user.

FIG. 1 shows an example of headphones 1001 on which electrodes 1000 for electroencephalogram measurement are provided, according to Japanese Laid-Open Patent Publication No. 2001-187034. In this publication, the electrodes 1000 for electroencephalogram measurement are provided on a support band portion of the headphones 1001, thus resulting in a shape such that the electrodes for electroencephalogram measurement will come in contact with the scalp as soon as the headphones 1001 is worn.

The potential of an electroencephalogram which is measurable on the scalp is very weak, e.g., on the order of 10 μV to 100 μV. Therefore, the electroencephalogram is susceptible to the influences of electrical noises that are generated by neighboring devices. When electrodes are provided in the vicinity of audio signal generators (electro-acoustic transducers) as in Japanese Laid-Open Patent Publication No. 2001-187034, supra, electrical noises from the electro-acoustic transducers will be superposed on the measured electroencephalogram. On the other hand, Japanese Laid-Open Patent Publication No. 9-131331 discloses removing noises in a band from 4 to 30 Hz of the electroencephalogram, by using a preestimated noise spectrum shape.

However, it has hitherto been considered that the frequency band of the audible range is not a noise source. The reason is a belief that the frequency band of an electroencephalogram for use does not overlap the audible range. The frequency band of an acoustic signal which is output from an audio-visual device spans the whole or a part of the frequency band of the human audible range, i.e., 20 Hz to 20000 Hz. The frequency band of electrical noises ascribable to the electro-acoustic transducers which output acoustic signals extends beyond the lower frequency limit (about 20 Hz) of acoustic signals. On the other hand, the frequency band of the electroencephalogram for use contains event-related potentials at 10 Hz or less, θ waves from 4 Hz to 8 Hz, and α waves from 8 Hz to 13 Hz, for example. In other words, the acoustic signal frequency band differs from the electroencephalogram frequency band. Also for the β waves at 13 Hz or higher which are contained in the electroencephalogram, it is often the case that a low-pass filter with a cutoff frequency of about 100 Hz is used at measurement. Thus, it has been believed that most of the electrical noises ascribable to acoustic signals in the audible range are not a major problem to electroencephalogram measurement.

SUMMARY OF THE INVENTION

Through experimentation, the inventors became the first to realize that low-frequency electrical noises contained in an acoustic signal may be superposed on an electroencephalogram under the influence of an electro-acoustic transducer which is in proximity of an electrode(s) for electroencephalogram measurement.

The present disclosure has been made in view of the above problems, and an objective thereof is to reduce influences of influences of electrical noises in electroencephalogram measurement.

An electroencephalogram measurement apparatus according to an embodiment of the present disclosure comprises: an electroencephalogram measurement section for measuring an electroencephalogram of a user by using a plurality of electrodes; an electro-acoustic transducer for presenting an acoustic signal to the user, the electro-acoustic transducer being in a vicinity of at least one electrode among the plurality of electrodes while the electroencephalogram measurement section is worn by the user; an amplitude envelope extraction section for extracting an amplitude envelope of the acoustic signal presented by the electro-acoustic transducer; a frequency analysis section for applying a frequency analysis to the amplitude envelope extracted by the amplitude envelope extraction section; and a noise estimation section for estimating an electrical noise which originates from the electro-acoustic transducer and is mixed at the at least one electrode by using a previously provided set of transform rules and a result of frequency analysis of the extracted amplitude envelope.

Other features, elements, processes, steps, characteristics and advantages of the present invention will become more apparent from the following detailed description of preferred embodiments of the present invention with reference to the attached drawings.

BRIEF DESCRIPTION OF THE DRAWINGS

FIG. 2A is a potential waveform graph of an electroencephalogram (electroencephalogram waveform) which was recorded when a sufficiently large sine-wave acoustic signal at 5 Hz was output while bone-conduction headphones were held at a position 1 cm above an electrode on the scalp.

FIG. 2B is a diagram showing a frequency spectrum of the waveform of FIG. 2A.

FIG. 2C is a diagram showing a frequency spectrum of an electroencephalogram which was recorded with the same electrode as in FIG. 2A when the bone-conduction headphones were moved away from the electrode for electroencephalogram measurement, thus ensuring a sufficient distance between the electrode and the bone-conduction headphones.

FIG. 4A is a potential waveform graph of an electroencephalogram (electroencephalogram waveform) which was recorded with an electrode when a signal (FIG. 3B) obtained by fluctuating the amplitude of pink noise at 5 Hz was output from a proximate electro-acoustic transducer.

FIG. 4B is a diagram showing a frequency spectrum of the waveform of FIG. 4A.

FIG. 4C is a diagram showing a frequency spectrum of a potential recorded when a signal obtained by fluctuating the amplitude of pink noise at 9 Hz was output.

FIG. 4D is a diagram showing a frequency spectrum of a potential recorded when a signal obtained by fluctuating the amplitude of pink noise at 17 Hz was output.

FIG. 4E is a diagram showing a frequency spectrum of an electroencephalogram recorded with the same electrode as in FIG. 4A when the bone-conduction headphones were moved away from the electrode for electroencephalogram measurement, thus ensuring a sufficient distance between the electrode and the bone-conduction headphones.

FIG. 24 is a flowchart showing a procedure of processing by the electroencephalogram measurement apparatus 52 of Embodiment 2.

FIG. 29 is a diagram showing the detailed construction of a band component analysis section 340.

FIG. 30 is a diagram showing the detailed construction of a noise estimation section 350.

FIG. 38 is a diagram schematically showing an example where determination criteria are set based on the band components of an output waveform.

FIG. 39 is a diagram showing an example of a determination criteria changing table 482.

FIG. 45 is an example of a determination criteria changing table 582 which is referred to by a linear discriminant criteria setting section 581.

FIG. 49 is a diagram showing a look-up table between noise amplitudes and determination criteria.

DETAILED DESCRIPTION OF PREFERRED EMBODIMENTS

Figure 1:
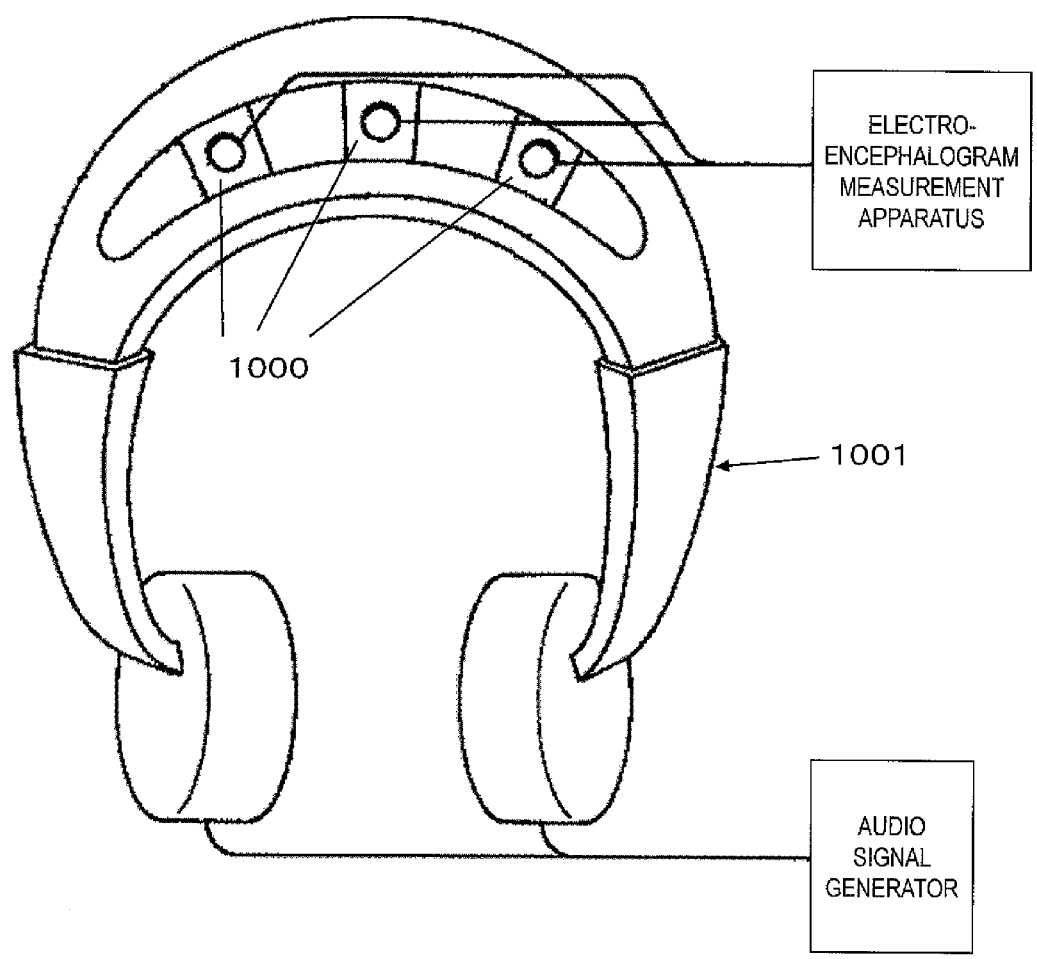
FIG. 1 is a diagram showing an example of headphones 1001 on which electroencephalogram electrodes are provided, according to Japanese Laid-Open Patent Publication No. 2001-187034.

An electroencephalogram measurement apparatus according to an embodiment of the present invention comprises: an electroencephalogram measurement section for measuring an electroencephalogram of a user by using a plurality of electrodes; an electro-acoustic transducer for presenting an acoustic signal to the user, the electro-acoustic transducer being in a vicinity of at least one electrode among the plurality of electrodes while the electroencephalogram measurement section is worn by the user; an amplitude envelope extraction section for extracting an amplitude envelope of the acoustic signal presented by the electro-acoustic transducer; a frequency analysis section for analysing a frequency of the amplitude envelope extracted by the amplitude envelope extraction section; and a noise estimation section for estimating an electrical noise which originates from the electro-acoustic transducer and is mixed at the at least one electrode by using a previously provided set of transform rules and the frequency of the extracted amplitude envelope analyzed by the frequency analysis section.

The set of transform rules may define correspondence between frequencies of amplitude envelope and transform coefficients; and the noise estimation section may estimate the electrical noise by using an instantaneous frequency of the amplitude envelope and the set of transform rules to determine a transform coefficient corresponding to the instantaneous frequency, and multiplying the amplitude envelope by the determined transform coefficient.

The noise estimation section may estimate the electrical noise by using a set of transform rules which defines smaller transform coefficients for larger frequencies.

The noise estimation section may estimate the electrical noise by using a set of transform rules such that the transform coefficient converges to zero between frequencies of 20 Hz and 30 Hz.

The electroencephalogram measurement apparatus may further comprise a reduction section for removing the estimated electrical noise from the electroencephalogram.

The set of transform rules may be a previously provided transform function; and the noise estimation section may determine a transform coefficient from the frequency of the extracted amplitude envelope into a noise estimate value according to the previously provided transform function, and, based on the transform coefficient, may estimate a noise which originates from the electro-acoustic transducer due to the amplitude envelope and is electrically mixed into an input signal at the at least one electrode.

The electroencephalogram measurement apparatus may further comprise a reduction section for removing the estimated electrical noise from the electroencephalogram.

An electroencephalogram measurement apparatus according to an embodiment of the present invention is an electroencephalogram measurement apparatus for determining an intent of a user from a measured electroencephalogram according to a previously provided determination criterion, comprising: an electroencephalogram measurement section for measuring an electroencephalogram of the user by using a plurality of electrodes; an electro-acoustic transducer for presenting an acoustic signal to the user, the electro-acoustic transducer being in a vicinity of at least one electrode among the plurality of electrodes while the electroencephalogram measurement section is worn by the user; an amplitude envelope extraction section for extracting an amplitude envelope of the acoustic signal presented by the electro-acoustic transducer; a frequency analysis section for analysing a frequency of the amplitude envelope extracted by the amplitude envelope extraction section; a noise estimation section for estimating an electrical noise which originates from the electro-acoustic transducer and is mixed at the at least one electrode by using a previously provided set of transform rules and the frequency of the extracted amplitude envelope analyzed by the frequency analysis section; and a determination criteria setting section for changing the determination criterion in accordance with the estimated noise.

The set of transform rules may be a previously provided transform function; and the noise estimation section may determine a transform coefficient from the frequency of the extracted amplitude envelope into a noise estimate value according to the previously provided transform function, and, based on the transform coefficient, may estimate a noise which originates from the electro-acoustic transducer due to the amplitude envelope and is electrically mixed into an input signal at the at least one electrode.

The transform function may be a mathematical function defining a transform coefficient such that the transform coefficient becomes smaller for higher frequencies, and converges to zero between frequencies of 20 Hz and 30 Hz of a component contained in the output acoustic signal.

The transform function may define mapping of transform coefficients onto a predetermined plurality of bands.

The amplitude envelope extraction section may extract the amplitude envelope of the acoustic signal by applying a time-frequency separation to the acoustic signal through a wavelet transform.

The amplitude envelope extraction section may extract the amplitude envelope of the acoustic signal by applying a time-frequency separation to the acoustic signal through the Fourier transform.

Among components which are obtained by applying a time-frequency separation to the acoustic signal, the amplitude envelope extraction section may extract a frequency component that is equal to or less than a predetermined upper-limit frequency between 20 Hz and 30 Hz as the amplitude envelope of the acoustic signal.

The amplitude envelope extraction section may determine from the acoustic signal a frequency component of a time-frequency domain by applying a wavelet transform for a frequency band containing a predetermined electroencephalogram frequency and a predetermined time zone, and extract and output the amplitude envelope of the acoustic signal by applying an inverse wavelet transform to the determined frequency component of the time-frequency domain.

The noise estimation section may use the transform function to determine a transform coefficient corresponding to a frequency component contained in the acoustic signal.

The electroencephalogram measurement apparatus may further comprise a storage section for storing the transform function.

The determination criterion may be a criterion to be used for determining an intent of the user based on similarity levels between the measured electroencephalogram and a plurality of pieces of reference electroencephalogram data, and comprise a threshold value or a combination of a plurality of threshold values for the similarity levels.

The at least one electrode may be integral with the electro-acoustic transducer.

A method of estimating an electrical noise according to the present invention comprises the steps of: measuring an electroencephalogram of a user by using a plurality of electrodes; presenting an acoustic signal to the user by using an electro-acoustic transducer which is in a vicinity of at least one electrode among the plurality of electrodes while the electroencephalogram measurement section is worn by the user; extracting an amplitude envelope of the acoustic signal presented by the electro-acoustic transducer; and analysing a frequency of the amplitude envelope; and estimating an electrical noise which originates from the electro-acoustic transducer and is mixed at the at least one electrode by using a previously provided set of transform rules and the frequency of the extracted amplitude envelope.

A computer program according to the present invention is a computer program, stored on a non-transitory computer-readable medium, to be executed by a computer mounted in an electroencephalogram measurement apparatus, wherein the computer program causes the computer to execute the steps of: receiving data of an electroencephalogram of a user measured by using a plurality of electrodes; presenting an acoustic signal to the user by using an electro-acoustic transducer which is in a vicinity of at least one electrode among the plurality of electrodes while the electroencephalogram measurement section is worn by the user; extracting an amplitude envelope of the acoustic signal presented by the electro-acoustic transducer; and analysing a frequency of the amplitude envelope; and estimating an electrical noise which originates from the electro-acoustic transducer and is mixed at the at least one electrode by using a previously provided set of transform rules and the frequency of the extracted amplitude envelope.

In accordance with an electroencephalogram measurement apparatus of the present invention, an electroencephalogram measurement apparatus can be operated without being influenced by a low-frequency electrical noise originating from an electro-acoustic transducer which is in proximity to or in contact with an electrode for electroencephalogram measurement.

The inventors have found a phenomenon where a low-frequency electrical noise is superposed on an electroencephalogram under the influence of an electro-acoustic transducer which is in proximity to an electrode for electroencephalogram measurement. Hereinafter, an experiment through which this phenomenon was confirmed will be described in detail. Thereafter, embodiments of the present invention will be described.

FIG. 2A is a potential waveform graph of an electroencephalogram (electroencephalogram waveform) which was recorded when a sufficiently large sine-wave acoustic signal at 5 Hz was output while bone-conduction headphones were held at a position 1 cm above the electrode on the scalp. The electroencephalogram waveform was recorded with an electrode for electroencephalogram measurement which was worn at the left temple. The vertical axis represents electroencephalogram potential, whereas the horizontal axis represents time. The potential is in units of microvolts, whereas the time is in units of milliseconds. The frequency of 5 Hz is meant to be a lower frequency than those of α waves, which are supposed to be 8 Hz to 13 Hz. In a zone of one second indicated by a both-sided arrow in FIG. 2A, five potential peaks appear as indicated by reversed triangle marks. The peaks are at an equal interval, thus indicative of five periodic fluctuations in potential during one second. What this electroencephalogram waveform indicates is that a 5 Hz signal is superposed on the electroencephalogram.

FIG. 2B is a diagram showing a frequency spectrum of the waveform of FIG. 2A. The vertical axis represents relative energy, whereas the horizontal axis represents frequency. The frequency is in units of hertz (Hz). This frequency spectrum contains components at frequencies which are multiples of 5, e.g., 10 Hz, 15 Hz, 20 Hz, other than that of 5 Hz observed in FIG. 2A.

In the measurements taken by the inventors, these components were also observed in an electroencephalogram potential recorded with an electrode which was worn at the right temple, in addition to the electrode to which the bone-conduction headphones were brought near. That is, the noises were spread over the entire head.

FIG. 2C is a diagram showing a frequency spectrum of an electroencephalogram which was recorded with the same electrode as in FIG. 2A when the bone-conduction headphones were moved away from the aforementioned electrode for electroencephalogram measurement, thus ensuring a sufficient distance between the electrode and the bone-conduction headphones. Other than the fact that an AC noise of 60 Hz is observed, no noise components at frequencies which are multiples of 5 are observed unlike in FIG. 2B, and an electroencephalogram component is observed in a low range of 10 Hz or less.

When listening to music or voices, it would be rare for a large low-frequency signal such as what would result in the electroencephalogram of FIG. 2A to be output through an electro-acoustic transducer of a wearable device. In many cases, any low-frequency signal that is lower than the lower-limit frequency of the audible range would appear in the form of amplitude fluctuations of an acoustic signal that pertains to a higher-frequency audible range. Rhythms of music, repetitive patterns of vowels and consonants of a voice, and so on are examples thereof.

Figure 3A:
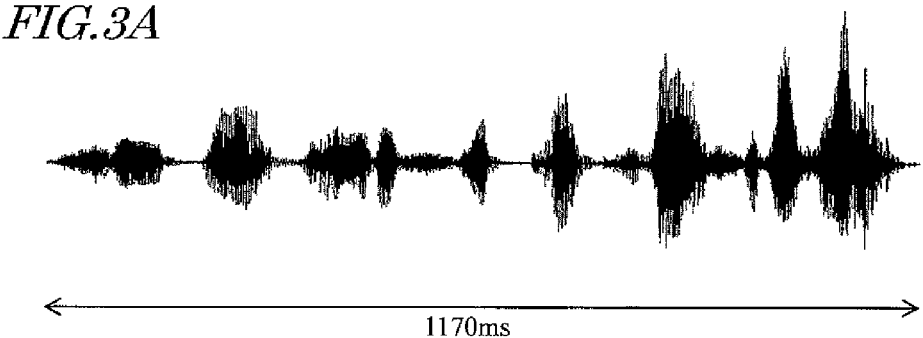
FIG. 3A is a diagram showing the waveform of a recorded voice.

FIG. 3A shows the waveform of a recorded voice when an adult male speaker says "supa 'gyoretsu' de tokubai shite-masuyo (meaning "there is a sale going on at Supermarket Gyoretsu" in Japanese.

Within a voice, a vowel is a sound which occurs as the vibration of the vocal cords is allowed to resonate in the throat, the oral cavity, and the nasal cavity. When a vowel is uttered, there is a large energy (i.e., sound pressure level) that is released from the mouth, which would appear as a large amplitude in a waveform presentation.

On the other hand, a consonant has as its main component the noises which are associated with a turbulent flow occurring when a breath flow is narrowed or temporarily stopped by articulatory organs such as the throat, the tongue, the teeth, and/or the lips. The energy of a turbulent flow noise is smaller than the vibration energy of the vocal cords. Speech sounds are uttered by combinations of consonants and vowels, thus resulting in signals with periodic amplitude fluctuations as shown in FIG. 3A.

Although most of the acoustic signals which are output from an electro-acoustic transducer of a wearable device are within the audible range, the amplitude of such acoustic signals will fluctuate at a low frequency which is below the audible range. Therefore, the inventors have conducted an experiment to confirm the possibility that the low-frequency component which is contained as amplitude fluctuations of an acoustic signal may generate electrical noises.

In order to confirm the influence of amplitude fluctuations alone, a kind of pink noise to which amplitude fluctuations were introduced at a low frequency was used, instead of an actual voice. Pink noise is a noise having characteristics such that its power spectral density is in inverse proportion to frequency, thus resulting in frequency characteristics whose power becomes weaker toward higher frequencies. Since the sounds of musical instruments and voices have frequency characteristics such that their power becomes weaker toward higher frequencies, pink noise is conveniently employed for mocking the frequency characteristics of music, voices, or ambient noise.

Figure 3B:
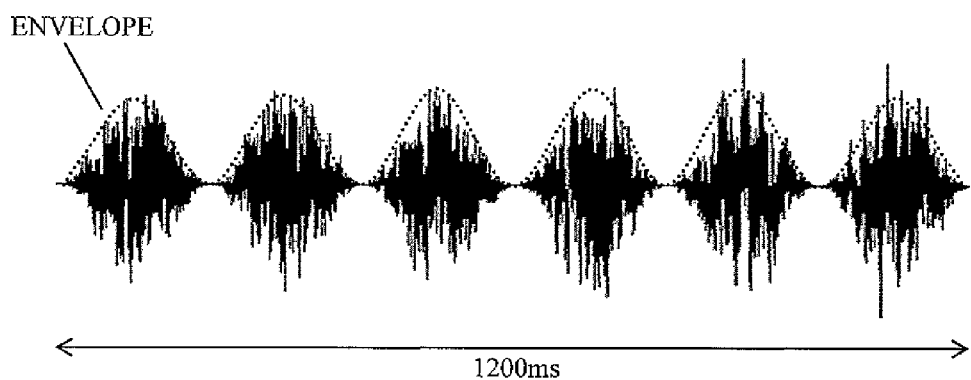
FIG. 3B is a diagram showing a time waveform of a signal, as well as an envelope of its amplitude, which is obtained by fluctuating the amplitude of pink noise with a 5 Hz sine wave.

FIG. 3B shows a time waveform of a signal, as well as an envelope of its amplitude, which is obtained by fluctuating the amplitude of pink noise with a 5 Hz sine wave. The solid line represents the time waveform, whereas the dotted line represents the envelope. The envelope is obtained by connecting amplitude values (local maximums) of the waveform across the time axis.

As shown by the broken line in FIG. 3B, the 5 Hz sine wave is manifested in the time waveform as an envelope which contours the amplitude fluctuations of the acoustic signal. By using an acoustic signal such as that shown in FIG. 3B, the inventors have conducted an experiment as to whether low-frequency electrical noises are superposed on an electrode for electroencephalogram measurement or not.

The inventors ensured that a pair of bone-conduction headphones was held at a position 1 cm above an electrode on the scalp, and an acoustic signal as shown in FIG. 3B was output. This experiment is similar to the experiment using a low-frequency (5 Hz) sine wave, of which results are shown in FIGS. 2A to 2C.

The acoustic signal had a signal level such that it was not audible as a sound. Thus, the electroencephalogram was prevented from fluctuating in synchronization with the amplitude fluctuations of the signal.

FIG. 4A is a potential waveform graph of an electroencephalogram (electroencephalogram waveform) which was recorded with an electrode when a signal (FIG. 3B) obtained by fluctuating the amplitude of pink noise at 5 Hz was output from a proximate electro-acoustic transducer. Similarly to FIG. 2A, the vertical axis represents electroencephalogram potential, whereas the horizontal axis represents time. The potential is in units of microvolts, whereas the time is in units of milliseconds.

FIG. 4B shows a frequency spectrum of the waveform of FIG. 4A. FIG. 4E shows a frequency spectrum of an electroencephalogram recorded with the same electrode as in FIG. 4A when the bone-conduction headphones were moved away from the electrode for electroencephalogram measurement, thus ensuring a sufficient distance between the electrode and the bone-conduction headphones. Similarly to FIGS. 2B and 2C, the vertical axis represents relative energy, whereas the horizontal axis represents frequency in FIGS. 4B and 4E. The frequency is in units of hertz (Hz).

While the 5 Hz component is not distinguishable in the waveform of FIG. 4A, a slight peak is observed at 5 Hz in the frequency spectrum of FIG. 4B. On the other hand, this peak is not observed in FIG. 4E. Therefore, it can be said that the peak near 5 Hz in FIG. 4B is a result of superposition of a noise that is in synchronization with the amplitude envelope.

In this experiment, in order to prevent the electroencephalogram from fluctuating in synchronization with the amplitude envelope of the acoustic signal, an acoustic signal having a low level below the audible range was used. Nevertheless, an electrical noise was mixed at the electrode for electroencephalogram measurement.

FIG. 4C shows a frequency spectrum of a potential recorded when a signal obtained by fluctuating the amplitude of pink noise at 9 Hz was output. FIG. 4D is a frequency spectrum showing a potential recorded when a signal obtained by fluctuating the amplitude of pink noise at 17 Hz was output. A slight peak is observed near 9 Hz in FIG. 4C, and near 17 Hz in FIG. 4D. These peaks are not observable in FIG. 4E.

Similarly to FIG. 4A, no low-frequency signal was recognized from the waveform in the case where the amplitude was fluctuated at 9 Hz or in the case where the amplitude was fluctuated at 17 Hz. Therefore, such waveform diagrams are omitted from illustration in FIG. 4A to 4E.

Figure 5:
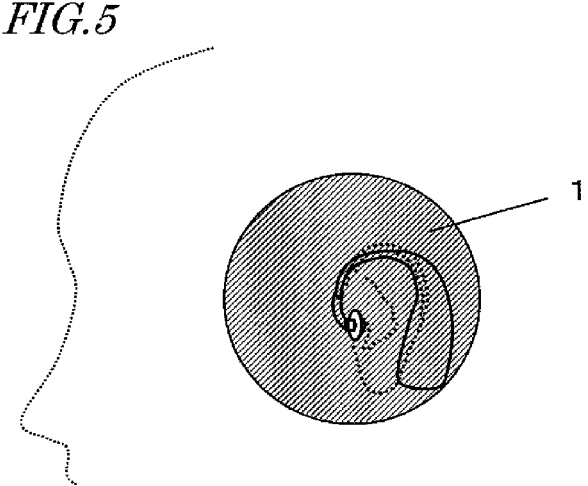
FIG. 5 is a diagram schematically showing a range 1 which is considered to be affected by electrical noises when an electro-acoustic transducer is located near an ear hole, as in the case of a hearing aid.

FIG. 5 schematically shows a range 1 which is considered to be affected by electrical noises when an electro-acoustic transducer is located near an ear hole, as in the case of a hearing aid. Electrical noises caused by the electro-acoustic transducer will presumably be mixed in the range 1 shown hatched in FIG. 5. The range 1 measures several centimeters around the electro-acoustic transducer, for example. If an acoustic signal at an audible level is used, even greater electrical noises will be mixed, and such mixing will occur over a broader range. For example, even in the case where the acoustic signal is below the audible range, the noise influence will appear in the acoustic signal up to about 2 cm around the electro-acoustic transducer as a center. In the case where the acoustic signal is well within the audible range, for example, if an acoustic signal which is not too loud to a person with normal hearing is output, the noise influence will appear in the acoustic signal up to about 5 cm around the electro-acoustic transducer as a center.

Through this experiment, it was confirmed that an electro-acoustic transducer used for outputting an acoustic signal in the audible range in electroencephalogram measurement may become a noise source in the frequency band that is utilized in connection with the electroencephalogram. As mentioned earlier, electro-acoustic transducers have never been regarded as problem noise sources.

Many of the contents which a user may play back on an HMD or a music player, and sounds in daily life which are heard through a hearing aid, have amplitude fluctuations. Voices of conversations or the like, which are the main subject of hearing, undergo syllable-by-syllable changes in the sound pressure level as shown in the example of FIG. 4B. In the exemplary case of Japanese, the utterance of an announcer in a TV news program may change at a speed of about 7 moras per second (where the mora is a unit of Japanese syllables). In other words, the changes in the sound pressure level ascribable to syllables are around 7 Hz. This means that a voice which is output from headphones or the like may have low-frequency noises of around 7 Hz being mixed.

A wearable device is worn on the head or over the ears of a user. For example, an HMD is worn on the head in the basic shape of goggles or eyeglasses. By taking an eyeglasses-shaped HMD for instance, the portions of the body of the user which come in contact with the HMD are limited to the nasion which comes in contact with nose pad portions 6a, the temples which come in contact with temple portions 6b of the frame, and an ear periphery 6d which comes in contact with each endpiece portion 6c, in the HMD 6 shown in FIG. 6, for example.

Figure 7:
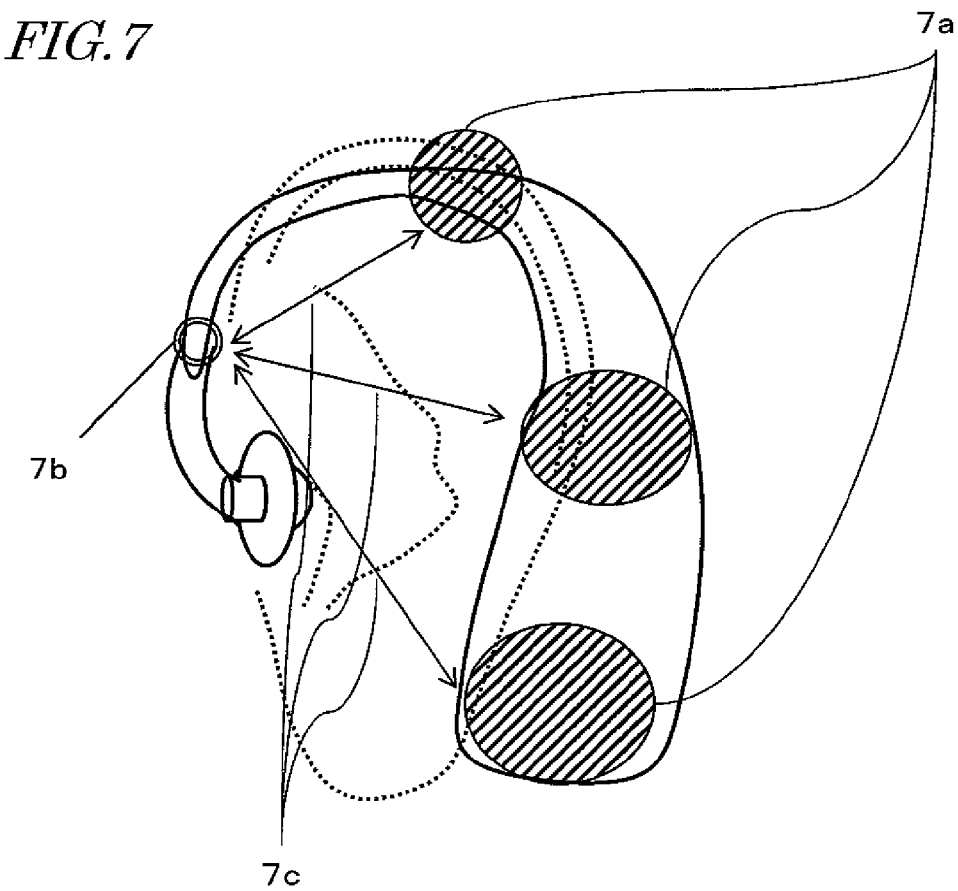
FIG. 7 is a diagram showing an example of wearing an ear-hung type hearing aid.

In the case of a music player, as in headphones which are shaped so as to be fitted in the ear holes or clip-type headphones which sandwich the auricles, the portions of the body that come in contact with the device are confined in the ear peripheries. An ear-hole type hearing aid is to be worn in the ear hole. FIG. 7 shows an ear-hung type hearing aid 7. The ear-hung type hearing aid 7 is worn by being hung on the auricle, as shown in FIG. 7. An ear-hole type or ear-hung type device will come in contact with the body only at the ear or the peripheral positions 7a thereof. Thus, electrodes are attached at such positions of contact. Therefore, in order to accommodate electrodes for electroencephalogram measurement in such a device, the electrodes for electroencephalogram measurement will be disposed in proximity to an electro-acoustic transducer 7b of the headphone or the like that is disposed in the ear hole or over the auricle. It can be seen from FIG. 7 that the distances 7c between the positions 7a where the electrodes are disposed and the electro-acoustic transducer 7b, which is the noise source, are sufficiently short for noise influences to occur.

The potential of an electroencephalogram which is measurable on the scalp is on the order of 10 μV to 100 μV. Accurate electroencephalogram measurement will be difficult if AC noises which are generated by neighboring electronic devices, or noises such as an electromyographic potential caused by a user motion or an electrooculographic potential caused by blinking, are superposed on the electroencephalogram. This makes it necessary to remove noises from the electroencephalogram. For this purpose, many commercially-available electroencephalographs incorporate a notch filter for the AC source frequency, for example. Also performed are filtering based on a difference between the frequency band effectively defining the electroencephalogram and the noise band, and noise reduction by separating any signal that is of a different frequency from the electroencephalogram through signal processing such as a wavelet transform, as in Japanese Laid-Open Patent Publication No. 2001-61800, for example.

When the electrodes are placed in the vicinity of an electro-acoustic transducer as described above, a low-frequency band noise from the electro-acoustic transducer that corresponds to the band of the electroencephalogram will be superposed on the electroencephalogram.

The electroencephalogram is recorded through a differential amplification which extracts a potential difference between a reference electrode and a measurement electrode. Therefore, if the same noise is superposed on the reference electrode and the measurement electrode, that is, if the reference electrode and the measurement electrode are at the same distance from the electro-acoustic transducer which is the noise source, the noise will be canceled through differential amplification, thus being removed.

However, the noise level will differ depending on the distance from the noise source. Therefore, as in the hearing aid shown in FIG. 7, the noise will not be canceled when two electrodes are at different distances from an electro-acoustic transducer, thus not being completely removed.

The inventors arrived at the concept of extracting an amplitude envelope of an output acoustic signal, and applying a frequency analysis to the amplitude envelope in order to estimate an electrical noise which arises from the amplitude envelope and is mixed at an electrode for electroencephalogram measurement, which in itself is a low-frequency signal. Then, relying on the estimated noise to perform a noise counteracting process for the potential derived from the electrode for electroencephalogram measurement, the inventors have succeeded in obtaining an electroencephalogram which is not affected by the noise originating in the acoustic signal even during the outputting of the acoustic signal.

Figure 8:
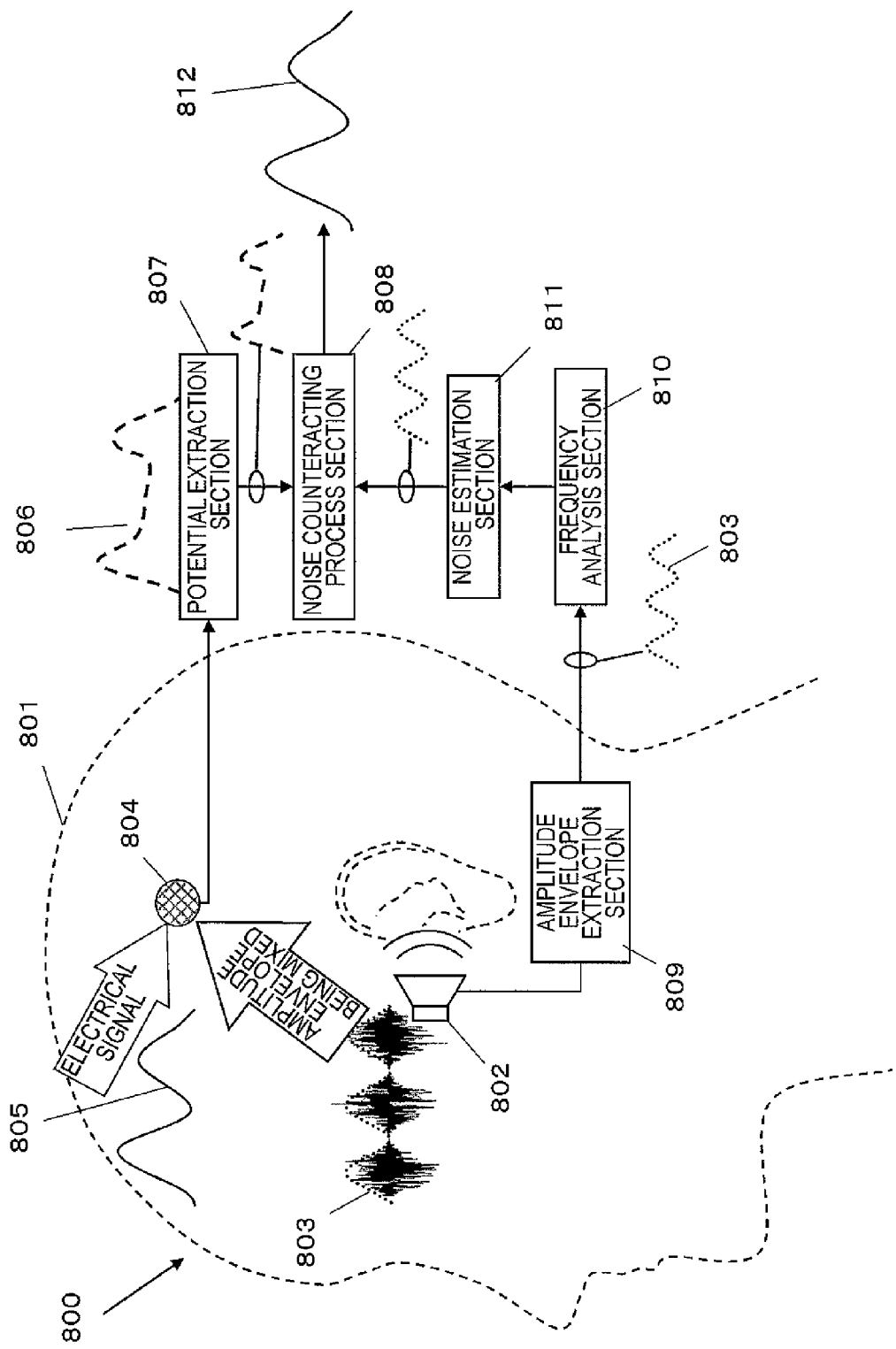
FIG. 8 is a diagram showing the present invention in outline.

FIG. 8 shows the present invention in outline. A contour line 801 in FIG. 8 depicts a contour of the head of a user 800 as viewed from the left, together with the left ear. To the ear of the user 800, an acoustic signal is presented via an earphone 802, and an amplitude envelope 803 of the acoustic signal, shown by the dotted line, is mixed as a low-frequency noise at an electrode 804 which is worn on the head of the user 800 via the head tissue. On the other hand, an electrical signal indicative of encephalic activities 805 arrives at the electrode 804. The electrode 804 acquires a potential 806 which contains both the electrical signal which is derived from the encephalic activities 805 and the low-frequency noise which originates from the amplitude envelope 803 of the acoustic signal. Via a potential extraction section 807, this potential is sent to a noise counteracting process section 808. From the acoustic signal which is output from the earphone 802, the amplitude envelope extraction section 809 extracts the amplitude envelope 803 of the acoustic signal, and outputs it to a frequency analysis section 810. In accordance with the result of frequency analysis by the frequency analysis section 810, a noise estimation section 811 estimates a potential which is associated with the amplitude envelope 803 being mixed as a noise, and outputs it to the noise counteracting process section 808. From the waveform containing both the electrical signal derived from the encephalic activities 805 (which is output from the potential extraction section 807) and the mixed amplitude envelope 803, the noise counteracting process section 808 subtracts the noise as estimated from the amplitude envelope of the acoustic signal (which is output from the noise estimation section 811), thus carrying out a noise counteracting process. As a result, a true electroencephalogram 812 which is free from the noise can be measured.

The inventors also arrived at the concept of extracting the low-frequency signal contained in the acoustic signal by analyzing the output acoustic signal, and setting a determination criterion for the electroencephalogram which takes into account the influence of the low-frequency signal on the electrode for electroencephalogram measurement. This method also makes it possible to obtain an electroencephalogram which is not affected by the noise originating in the acoustic signal even during the outputting of the acoustic signal.

By applying an electroencephalogram obtained through either one of the aforementioned processes to device manipulations based on an interface which utilizes the electroencephalogram, or a device having the function of monitoring user states on the basis of the electroencephalogram, such that the device is wearable and has an output section for outputting the acoustic signal, it has become possible to provide an electroencephalogram interface based on the electroencephalogram away from the influences of the noise originating in the acoustic signal, or realize monitoring of a user based on such an electroencephalogram.

Hereinafter, with reference to the attached drawings, embodiments of the electroencephalogram measurement apparatus according to the present invention will be described. The electroencephalogram measurement apparatus described in each embodiment has a mechanism for converting an electrical signal into sounds (acoustic output means). One example of the acoustic output means is an electro-acoustic transducer.

Embodiment 1

Figure 9:
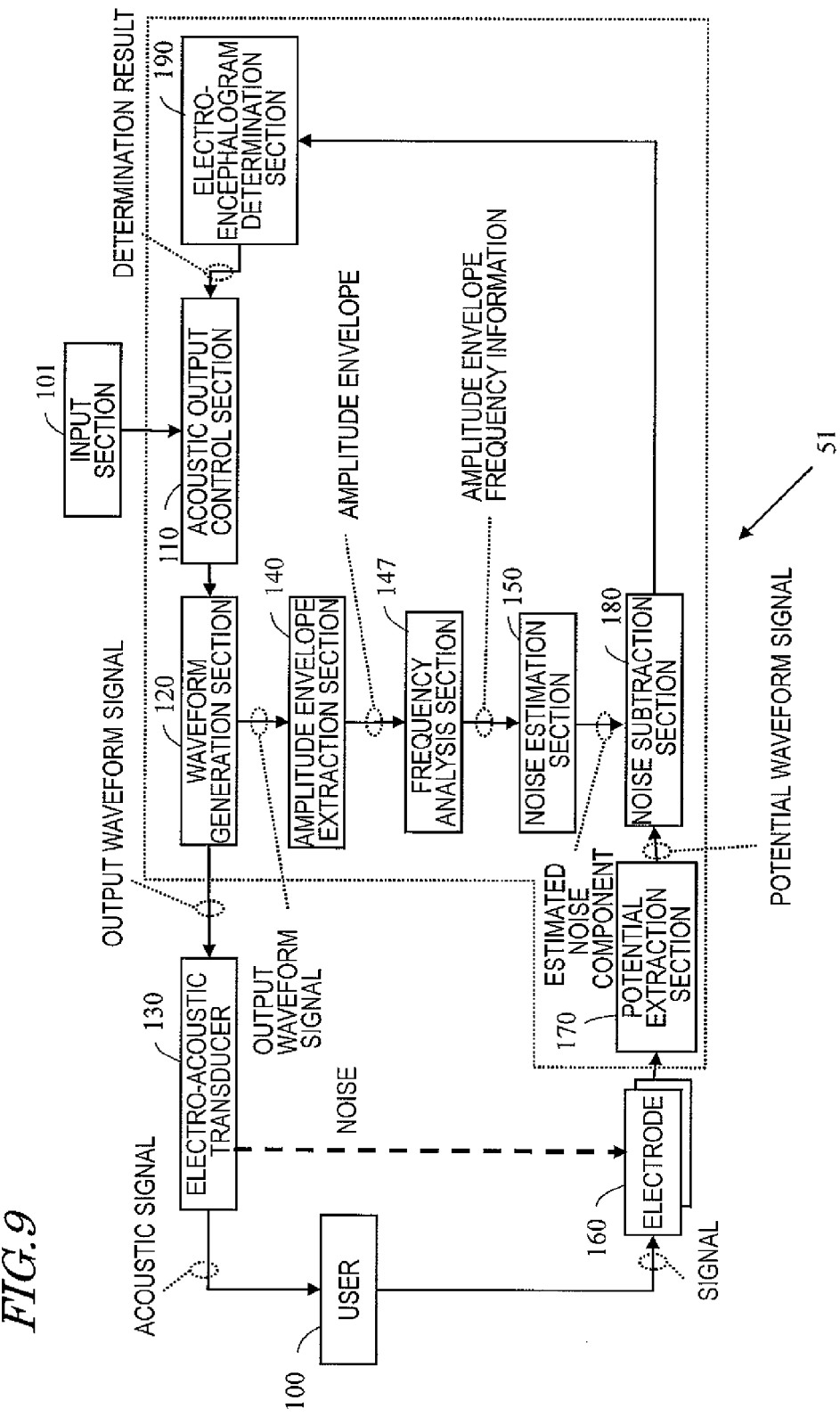
FIG. 9 is a construction diagram of an electroencephalogram measurement apparatus 51 according to Embodiment 1.

FIG. 9 is a construction diagram of an electroencephalogram measurement apparatus 51 according to the present embodiment. FIG. 10 to FIG. 13 respectively show the detailed constructions of constituent elements of the present embodiment. Note that a user 100 is illustrated for convenience of explanation; it will be appreciated that the user 100 is no constituent element of the electroencephalogram measurement apparatus 51.

Figure 6:
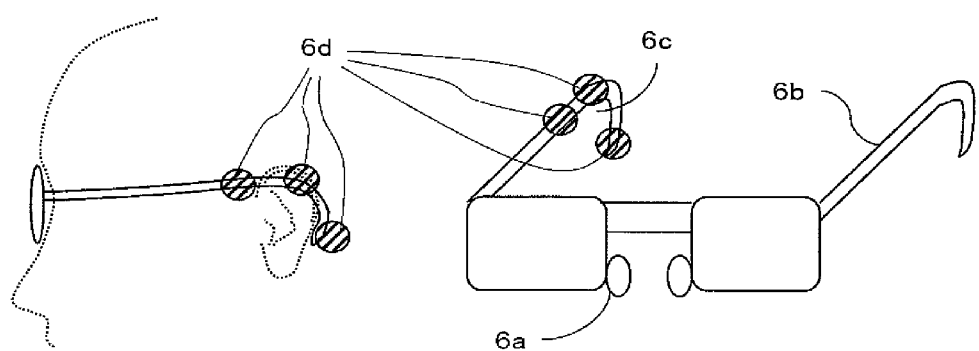
FIG. 6 is a diagram showing the construction of an HMD 6 which is in the shape of eyeglasses.

The present embodiment illustrates an example where user states are monitored based on an electroencephalogram and a device is automatically controlled in accordance with changes in the electroencephalogram. More specifically, it is an example where the sound volume of an acoustic output is manipulated in accordance with the frequency of occurrence of α waves in the electroencephalogram. Applications to an HMD as shown in FIG. 6 or a hearing aid as shown in FIG. 7 are possible.

The electroencephalogram measurement apparatus 51 includes an input section 101, an acoustic output control section 110, a waveform generation section 120, an electro-acoustic transducer 130, an amplitude envelope extraction section 140, a noise estimation section 150, an electrode section 160, a potential extraction section 170, a noise subtraction section 180, and an electroencephalogram determination section 190.

The input section 101 is a switch or the like with which the user 100 may manipulate an acoustic output.

The acoustic output control section 110 controls the acoustic signal to be output.

In accordance with a control signal from the acoustic output control section 110, the waveform generation section 120 generates a waveform of the acoustic signal to be output.

The electro-acoustic transducer 130 converts the waveform signal generated by the waveform generation section 120 into an acoustic signal for presentation to the user 100. The electro-acoustic transducer 130 can be composed by using an amplifier and a loudspeaker, for example.

The amplitude envelope extraction section 140 analyzes the waveform signal generated by the waveform generation section 120 to extract an amplitude envelope thereof.

The frequency analysis section 147 determines the frequency of the amplitude envelope which is extracted by the amplitude envelope extraction section 140.

Based on the frequency of the amplitude envelope determined by the frequency analysis section 147, the noise estimation section 150 estimates an electrical noise which is caused by the low-frequency component that has been extracted by the amplitude envelope extraction section 140.

The electrode section 160 includes at least two electrodes which are attached to the periphery(s) of one or both of the ears of the user 100: more specifically, electrodes functioning respectively as a reference electrode and a measurement electrode. The electrode section 160 is composed of metal pieces which come into contact with the skin, optionally with impedance conversion circuitry. Each electrode in the electrode section 160 acquires a potential at the position at which it is disposed. As will be described later, the potential extraction section 170 calculates a potential difference between the reference electrode and the measurement electrode. This potential difference is treated as an electroencephalogram.

It must be noted that, by placing the electrode section 160 in the vicinity of the electro-acoustic transducer 130, a noise occurring under the influence of the electro-acoustic transducer 130 is superposed on the potential of the resultant electroencephalogram. As used herein, the "vicinity" refers to a range where the low-frequency band noise is superposed on the electroencephalogram to a significant, i.e., nonnegligible, extent. For example, when the electro-acoustic transducer is placed at the center of a circle shown hatched in FIG. 5, the hatched region constitutes the "vicinity".

Although FIG. 9 illustrates the electrode section 160 and the electro-acoustic transducer 130 as separate elements, these may be integrally formed. At this time, all of the electrodes that are included in the electrode section 160 may be formed integrally with the electro-acoustic transducer 130, or some of the electrodes (at least one electrode) may be formed integrally with the electro-acoustic transducer 130.

Such constructions may also be adopted in any of the embodiments described below.

The potential extraction section 170 measures a difference between the potentials of two electrodes among the electrodes in the electrode section 160, and extracts a potential change. The potential extraction section 170 includes a CPU, a memory, an AD converter, and an amplifier, for example.

For the potential change which has been extracted by the potential extraction section 170, the noise subtraction section 180 performs a noise counteracting process of reducing the influence of the electrical noise estimated by the noise estimation section 150. Herein, the noise subtraction section 180 reduces the influence of the electrical noise through a subtraction. However, subtraction is only an example of such processes. Any calculation other than a subtraction process may also be employed so long as the noise can be reduced or removed. Whatever constituent element that performs various such calculations including subtraction can be referred to as a noise reduction section. The noise subtraction section 180 exemplifies a noise reduction section.

Based on the result of processing by the noise subtraction section 180, the electroencephalogram determination section 190 determines what sort of intent of the user 100 is reflected on the electroencephalogram, by utilizing a characteristic component contained in the electroencephalogram.

The acoustic output control section 110, the waveform generation section 120, the amplitude envelope extraction section 140, the frequency analysis section 147, the noise estimation section 150, the noise subtraction section 180, and the electroencephalogram determination section 190 are implemented by a CPU and a memory. The CPU and memory may also function as a portion of the potential extraction section 170. FIG. 9 indicates the constituent elements which are implementable by a CPU and a memory with a broken line surrounding them. By executing a computer program which is stored in the memory, the CPU may operate so as to function as one of the aforementioned constituent elements at a given point in time, or operate so that more than one constituent elements appear to be functioning at a given point in time.

Note that the number of CPUs and the number of memories do not need to be one each. For example, one CPU and one memory for electroencephalogram measurement for implementing a part of the amplitude envelope extraction section 140, the frequency analysis section 147, the noise estimation section 150, the noise subtraction section 180, the electroencephalogram determination section 190, and/or the potential extraction section 170 may be provided; another CPU and another memory for controlling content output may be provided for implementing the acoustic output control section 110 and the waveform generation section 120; and these may be independently operated.

Hereinafter, the internal construction of each of the aforementioned constituent elements will be described. For instance, FIG. 10 to FIG. 13 show internal functional blocks in the respective constituent element that is implemented by a CPU and a memory; unless otherwise specified, each such functional block is also implemented by a CPU and/or a memory. The specific operation of each functional block will be described below with reference to FIG. 14, FIG. 18, and so on.

Figure 10:
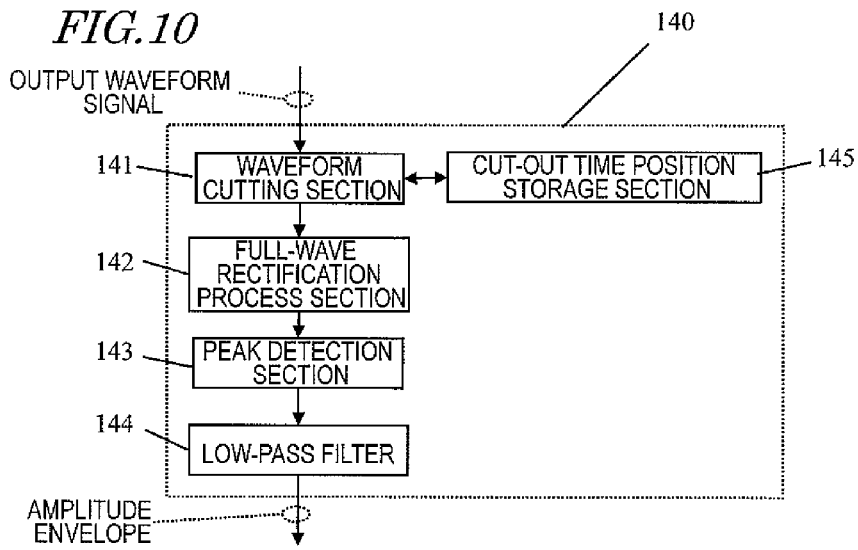
FIG. 10 is a diagram showing the detailed construction of an amplitude envelope extraction section 140.

FIG. 10 shows the detailed construction of the amplitude envelope extraction section 140. The amplitude envelope extraction section 140 includes a waveform cutting section 141, a full-wave rectification process section 142, a peak detection section 143, a low-pass filter 144, and a cut-out time position storage section 145 which is implemented by a memory.

Figure 11:
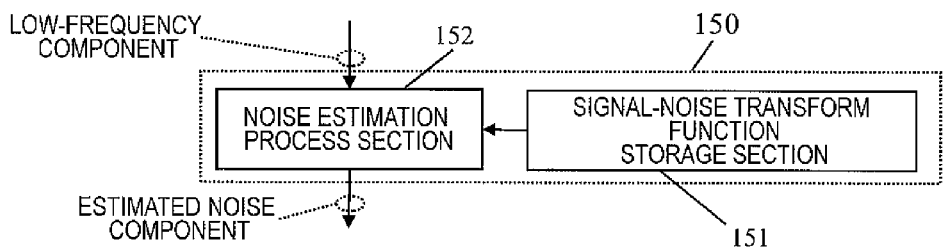
FIG. 11 is a diagram showing the detailed construction of a noise estimation section 150.

FIG. 11 shows the detailed construction of the noise estimation section 150. The noise estimation section 150 includes a signal-noise transform function storage section 151 implemented by a memory and a noise estimation process section 152.

Figure 12:
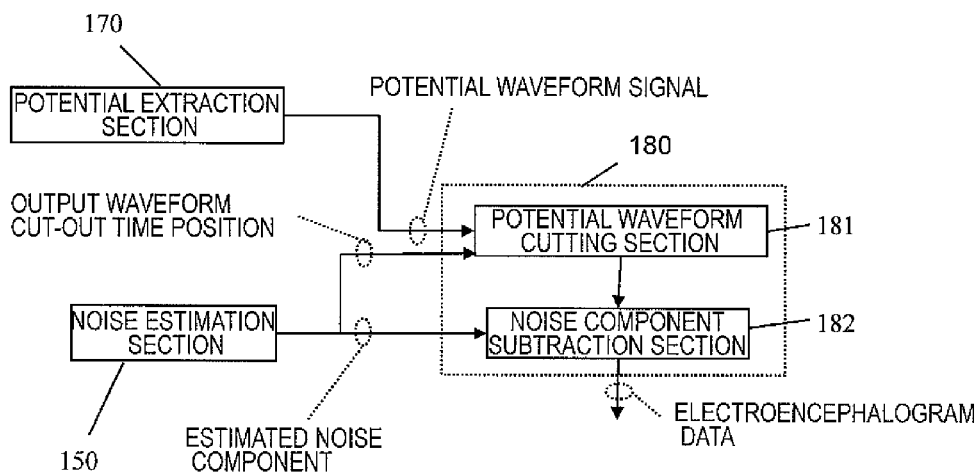
FIG. 12 is a diagram showing the detailed construction of a noise subtraction section 180.

FIG. 12 shows the detailed construction of the noise subtraction section 180. The noise subtraction section 180 includes a potential waveform cutting section 181 and a noise component subtraction section 182.

Figure 13:
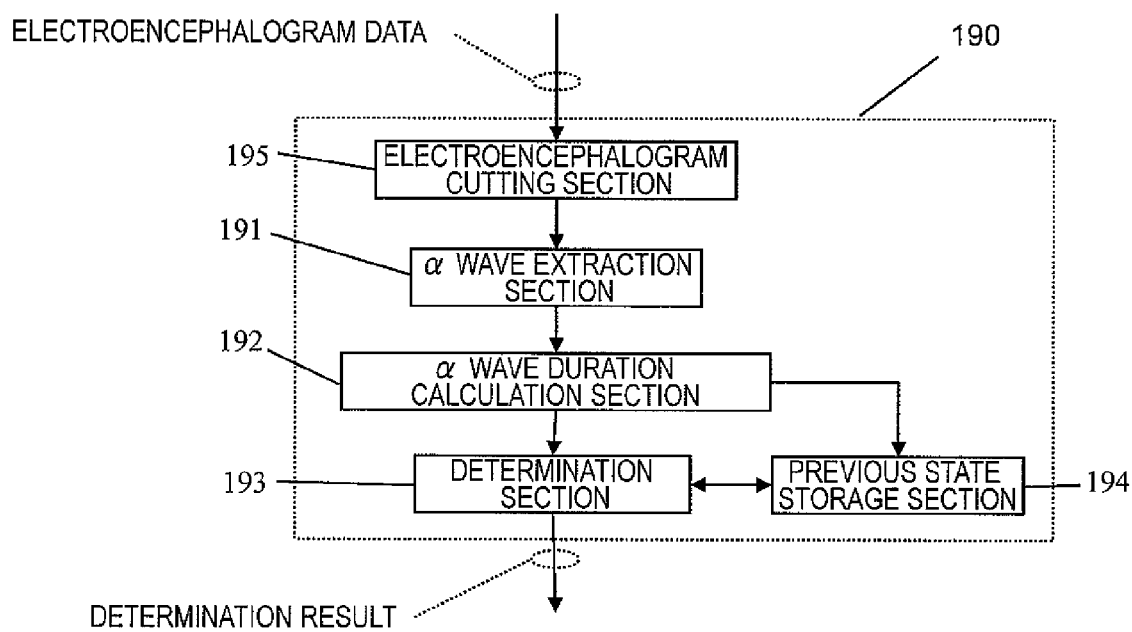
FIG. 13 is a diagram showing the detailed construction of an electroencephalogram determination section 190.

FIG. 13 shows the detailed construction of the electroencephalogram determination section 190. The electroencephalogram determination section 190 includes an α wave extraction section 191, an α wave duration calculation section 192, a determination section 193, a previous state storage section 194, and an electroencephalogram cutting section 195.

Figure 14:
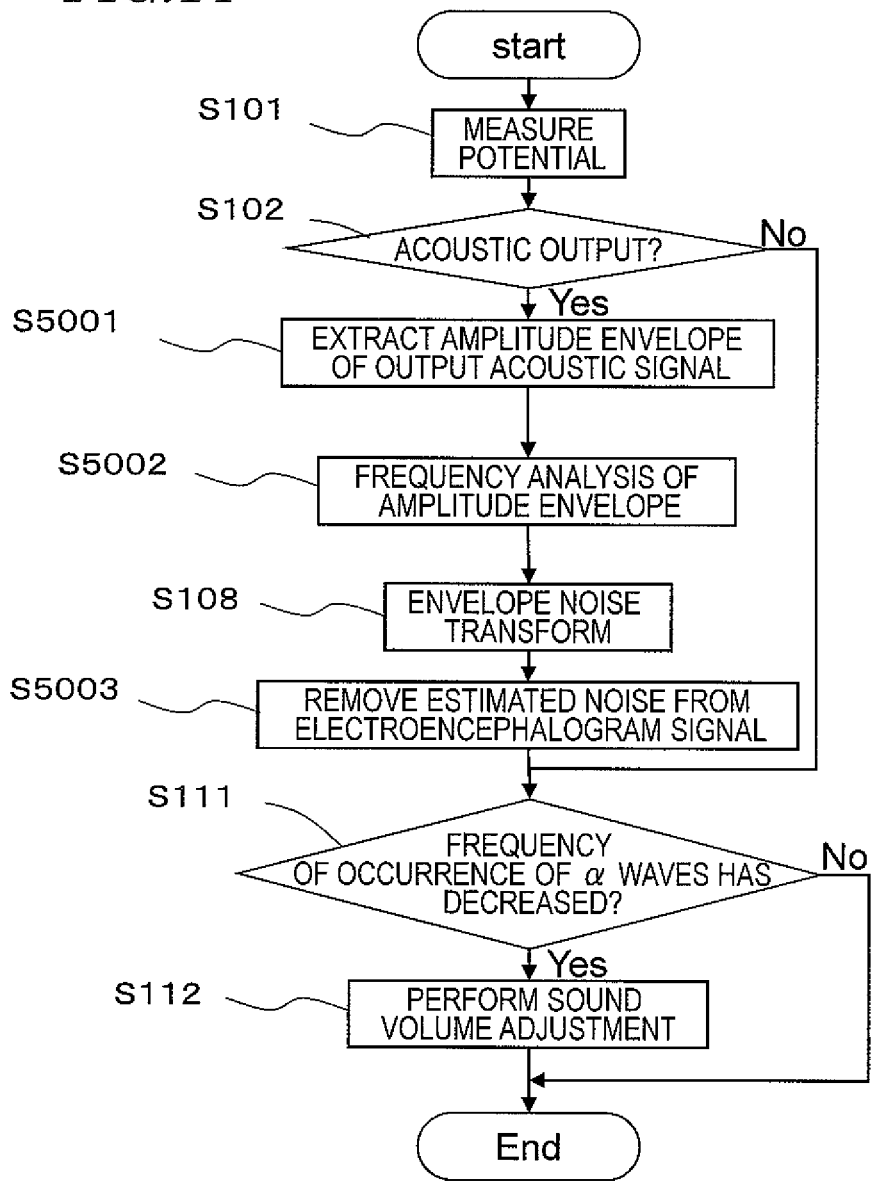
FIG. 14 is a flowchart showing a procedure of processing by the electroencephalogram measurement apparatus 51.

FIG. 14 is a flowchart showing the procedure of processing by the electroencephalogram measurement apparatus 51. Hereinafter, the procedure of processing will be described in order.

At step S101, among the plurality of electrodes in the electrode section 160, the potential extraction section 170 determines a potential difference between a predetermined reference electrode and each other measurement electrode. The reference electrode may be placed at one of the mastoids, for example.

At step S102, the waveform generation section 120 determines whether the acoustic output control section 110 is issuing an instruction for acoustic output or not. In the present embodiment, it is assumed that an instruction for acoustic output is to be given independently of the processing of FIG. 14. When step S102 finds that an instruction for acoustic output is being issued, it is meant that the waveform generation section 120 has been generating and outputting a waveform signal based on that instruction since before step S101 is executed.

If step S102 finds that an instruction for acoustic output is being issued (following Yes from step S102), the process proceeds to step S5001; if an instruction for acoustic output is not being issued (following No from step S102), the process proceeds to step S111.

In the present embodiment, a potential difference that is determined at step S101 while an acoustic signal is being output is presumed to contain a low-frequency electrical noise derived from the output waveform. Therefore, as a process of noise reduction, the electroencephalogram measurement apparatus 51 performs steps S5001, S5002, S108, and S5003.

At step S5001, the amplitude envelope extraction section 140 extracts an amplitude envelope of the output acoustic signal generated by the waveform generation section 120 as a low-frequency component. The method of extracting an amplitude envelope will be described in detail later with reference to FIG. 15.

At step S5002, the frequency analysis section 147 applies a frequency analysis to the amplitude envelope extracted at step S5001 as to its envelope profile. An instantaneous frequency of the envelope, i.e., low-frequency component (or low-range component), is obtained by a procedure of applying a Hilbert transform to the low-range component, calculating an instantaneous angular velocity for each sampling point, and converting the angular velocities into a frequency based on the sampling period, for example.

At step S108, the noise estimation process section 152 determines a coefficient corresponding to the instantaneous frequency of the envelope derived at step S5002.

Figure 16:
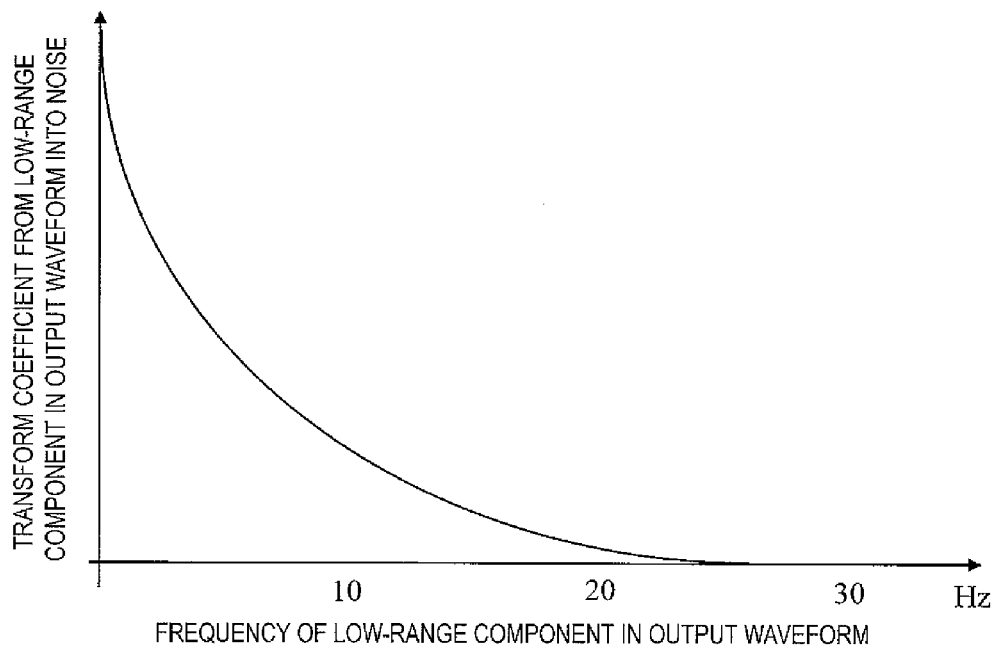
FIG. 16 is a diagram showing an example of a transform function.

The noise estimation process section 152 employs a transform function which is stored in the signal-noise transform function storage section 151. FIG. 16 shows an example of a transform function. The transform function is a mathematical function defining correspondence between the frequency of a low-range component of the output acoustic signal and the transform coefficient. More specifically, the transform function defines correspondence between frequencies and transform coefficients such that the transform coefficient becomes smaller (becomes weaker) as the frequency becomes higher. Furthermore, the transform function is chosen to define transform coefficients which converge to zero between the frequencies of 20 Hz and 30 Hz. The signal-noise transform function storage section 151 may retain a function expression as the transform function, or retain a table which discretely describes the relationship between frequencies and transform coefficients as shown in FIG. 16. Furthermore, the frequencies may be split into predetermined bands, and a transform coefficient may be assigned to each band. However, it is assumed that the sizes of the transform coefficients of the respective bands have a relationship conforming to the relationship shown in FIG. 16. In the present specification, the aforementioned transform function, table, and relationship between band units and transform coefficients will be collectively referred to as "transform rules". The transform rules are rules for establishing correspondence between frequencies and transform coefficients, and may be described in any arbitrary format.

The fact that the transform function converges to zero between 20 Hz and 30 Hz was experimentally confirmed from the frequency of the output signal from the electro-acoustic transducer and the frequency components of potentials recorded with an electrode for electroencephalogram measurement. Twenty hertz is supposed to be the lower-limit frequency of the audible range. This transform function indicates that relatively high frequency components which are in or close to the audible range do not generate noise, but that frequency components which are lower than 20 Hz are likely to induce noise at the electrode for electroencephalogram measurement.

Furthermore, such low frequencies which are likely to induce noise also overlap the frequencies of the electroencephalograms which are used in order to know user states, e.g., α waves, and the event-related potentials which are used in order to know states of perception or judgment. Therefore, by using the transform function such as that shown in FIG. 16 to accurately estimate and remove the noises that originate in the output signal from the electro-acoustic transducer (which may change depending on the frequency), it becomes possible to extract only a noise-free and accurate electroencephalogram from a noise-ridden electroencephalogram. This means that more accurate device manipulations utilizing the electroencephalogram are possible.

Then, by multiplying each value of the envelope (low-frequency component) by the determined coefficient, the noise estimation process section 152 estimates the low-frequency electrical noise originating from the output waveform as a time waveform.

At step S5003, the noise subtraction section 180 removes the noise waveform estimated by the noise estimation process section 152 at step S108 from the electroencephalogram. The method of removal will be described in detail later with reference to FIG. 18.

At step S111 in FIG. 14, the electroencephalogram determination section 190 determines whether the frequency of occurrence of α waves in the electroencephalogram has decreased or not. The electroencephalogram to be used for this process is determined as follows. If the current process follows from a No determination at step S102, the electroencephalogram determination section 190 treats and utilizes the potential difference acquired at step S101 as the electroencephalogram. On the other hand, if the current process follows after the process of step S5003, the electroencephalogram determination section 190 utilizes the electroencephalogram from which the noise waveform has been removed at step S5003. Then, the frequency of occurrence of α waves in that electroencephalogram is evaluated.

The method of evaluating the frequency of occurrence of α waves may be as follows, for example.

The electroencephalogram cutting section 195 cuts out an electroencephalogram waveform spanning a predetermined duration. The α wave extraction section 191 extracts α waves (about 8 Hz to 13 Hz) which are recorded in the electroencephalogram having been cut out by the electroencephalogram cutting section 195. The α wave duration calculation section 192 determines a total duration of the α waves observed within the waveform having been cut out, and the determination section 193 compares it against the total duration of past α waves that is stored in the previous state storage section 194. The duration to be used for determination may be 2 seconds, for example. However, the duration to be used for determination may be any value that defines a sufficient length for conducting a comparison of frequencies of occurrence of α waves, the duration being shorter than the duration of the output waveform that is cut out at step S103.

Specifically, extraction of α waves is performed by the following procedure, for example. First, the α wave extraction section 191 determines a root mean square (RMS) of the entire electroencephalogram that has been cut out. Apart from this, the α wave extraction section 191 splits the electroencephalogram having been cut out into regions each spanning 200 ms, and determines an RMS for each region. Then, among the RMS values of the respective regions, the α wave extraction section 191 identifies an RMS that exceeds the RMS of the entire electroencephalogram having been cut out by 10% or more, and extracts a region corresponding to that RMS. The α wave extraction section 191 smoothes the waveform within the extracted region by a method such as median smoothing, for example, and thereafter counts zero-crossing points to determine a frequency. If this frequency is between 8 Hz and 13 Hz, the 200 ms region is extracted as a zone containing α waves. The aforementioned method of extracting α waves is exemplary; any other method may also be performed.

At step S112, the acoustic output control section 110 adjusts the sound volume of the output acoustic signal. If step S111 finds that the frequency of occurrence of α waves has decreased, i.e., following Yes from step S111, the acoustic output control section 110 decreases the sound volume of the acoustic output (step S112). If step S111 finds that the frequency of occurrence of α waves has not decreased, i.e., following No from S111, the acoustic output control section 110 makes no change in the acoustic output.

Although the present embodiment illustrates manipulation of the sound volume of an acoustic output based on the frequency of occurrence of α waves, any other manipulation may also be controlled, e.g., turning off of the power switch, switching between modes, or the like. In the case of a hearing aid, in particular, a manipulation of automatically switching between a mode for concentrating on conversations, a mode for allocating casual attention to the crowd noise, and the like may be made on the basis of an electroencephalogram.

During the process shown in FIG. 14, the electroencephalogram (e.g., an event-related potential) of the user may fluctuate in terms of amplitude, timing of occurrence, and the like, due to the outputting of the acoustic signal. However, such fluctuations in the electroencephalogram will not affect the aforementioned process because the process of FIG. 14 aims at removing the noise that is directly superposed at an electrode from the electro-acoustic transducer, such noise occurring substantially simultaneously with the outputting of the acoustic signal.

Next, the details of the method of extracting an amplitude envelope at step S5001 shown in FIG. 14 will be described with reference to the flowchart of FIG. 15 and the schematic diagram of FIG. 17.

Figure 15:
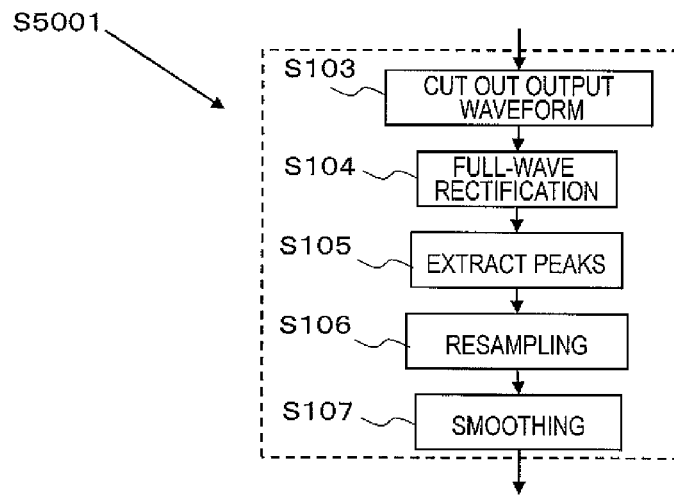
FIG. 15 is a flowchart showing the details of a method of extracting an amplitude envelope at step S5001 shown in FIG. 14.

At step S103 in FIG. 15, the waveform cutting section 141 in the amplitude envelope extraction section 140 cuts out a waveform signal spanning a certain predetermined duration from the waveform signal generated by the waveform generation section 120 at step S102. To the cut-out time position storage section 145, the waveform cutting section 141 stores cut-out time position information: for example, information describing the time (time position) of conducting the cutting (e.g., a duration from a base point in time to the cutting start time in units of seconds). The duration of cutting may be 2 seconds, for example. This duration must be equal to or greater than the duration for which a potential waveform is cut out when making an electroencephalogram determination. The cut-out time position information may be described in any other format that describes a cutting start time and a cutting end time, e.g., from 3 seconds to 5 seconds after a base point in time.

Figure 17:
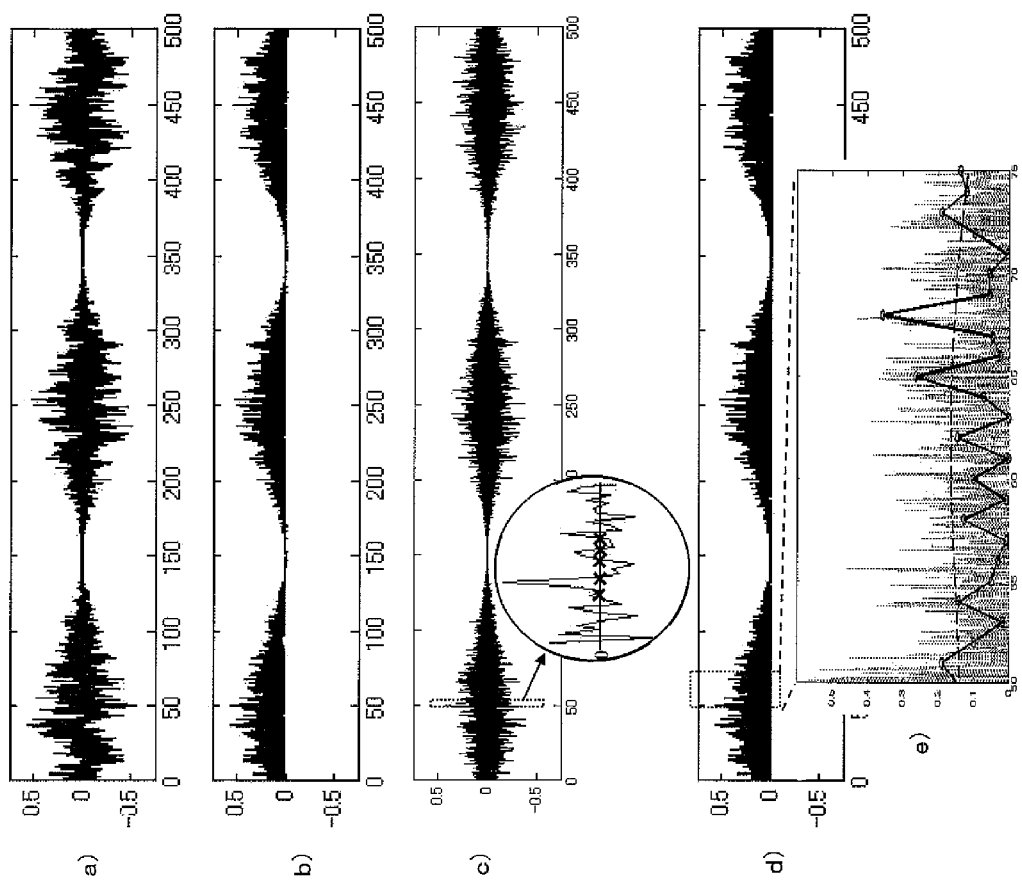
FIG. 17 is waveform diagrams for describing a method of extracting an amplitude envelope.

In FIG. 17, (a) shows an example time waveform of the acoustic signal which is cut out at step S103. The horizontal axis represents elapsed time in units of milliseconds. In FIG. 17, (a) shows α waveform spanning 500 milliseconds. The vertical axis represents the instantaneous value at each sampling point, i.e., a relative value of instantaneous energy. Since an acoustic signal is a compressional wave of air density by nature, its relative value may actually take negative values. Although 500 milliseconds are illustrated in FIG. 17, the process may be conducted over the entire period of the waveform that has been cut out.

At step S104 in FIG. 15, the full-wave rectification process section 142 determines an absolute value of the instantaneous value at each sampling point of the waveform having been cut out by the waveform cutting section 141. This results in a full-wave rectification. In FIG. 17, (b) shows a waveform after conducting the full-wave rectification. This process is a process of folding over, to the positive side, any portion of the acoustic signal shown in (a) of FIG. 17 where its instantaneous value has a negative relative value. The full-wave rectification is a process for allowing an the "sparse"-side amplitude and the "dense"-side amplitude of a compressional wave, with respect to the zero energy state, to be treated in similar manners.

At step S105, the peak detection section 143 detects peaks of the full-wave rectified waveform. Specifically, in the waveform data sequence which is a time sequence of values of the waveform as converted into absolute values at step S104, the peak detection section 143 derives a data sequence of differences between adjoining data points. Then, the values in the data sequence of the full-wave rectified waveform at the respective data positions where the sign is inverted are detected as peak positions.

In FIG. 17, (c) shows a result of detecting differences between adjoining data points in the full-wave rectification process shown in (b) of FIG. 17, i.e., a time sequence of values of the acoustic signal waveform as converted into absolute values. A portion of the waveform is shown in the circle. In the data sequence representing differences between adjoining data points, points indicated by X symbols in the circle are the data positions at which the sign is inverted. The peak detection section 143 detects values in the data sequence of the full-wave rectified waveform, i.e., values in (b) of FIG. 17, that correspond to these points. In FIG. 17, (d) shows the result of extraction.

At step S106 in FIG. 15, the peak detection section 143 extracts and generates a data sequence of peak position data and time positions thereof, as shown in (d) of FIG. 17, and generates an envelope signal of waveform data by resampling this data sequence at an equal time interval.

In FIG. 17, (e) shows enlarged a portion of the waveform of (d). The dotted line in the graph represents values extracted at step S105 illustrated in (d) of FIG. 17, whereas the blank dots represent resampled values. Graphs (a) to (c) in FIG. 17 are obtained with a sampling frequency of 44.1 kHz, whereas graph (e) of FIG. 17 is obtained through resampling at a sampling frequency of 1 kHz.

At step S107 in FIG. 15, the peak detection section 143 outputs the envelope signal generated at step S106 to the low-pass filter 144. The low-pass filter 144 may be an FIR (Finite Impulse Response) filter with a cutoff frequency of 30 Hz, for example. Through the low-pass filter 144, the envelope signal can be smoothed. The data sequence which is output from the low-pass filter 144 is treated as the final envelope signal (amplitude envelope). The envelope signal is output as the presumable low-range component that is contained in the output waveform.

As shown in (e) of FIG. 17, by passing the data sequence shown by the blank dots through the low-pass filter, the data shown by the broken line is obtained. The entirety of (d) of FIG. 17 would appear as shown by the solid line in (f) of FIG. 17.

In FIG. 17, (f) shows the data sequence which is the result of full-wave rectification process generated at step S104 illustrated in (d) of FIG. 17 as well as the data sequence which has passed through the low-pass filter at step S107 (i.e., the envelope). The data value at each point in time indicates the result of full-wave rectification process, the value being read by the indexes on the left vertical axis (i.e., the vertical axis at the 0 time point). On the other hand, the solid line in (f) represents the envelope of that data sequence, with its value being read by the indexes on the right vertical axis (i.e., the vertical axis at the time point of 5000 ms). The values of the envelope are relative values.

Figure 18:
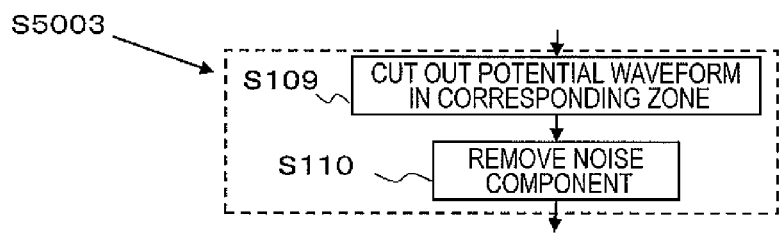
FIG. 18 is a flowchart showing the details of a method of extracting an amplitude envelope at step S5003 shown in FIG. 14.

Next, the details of the noise reduction at step S5003 shown in FIG. 14 will be described with reference to the flowchart of FIG. 18.

At step S109, from the potential waveform acquired at step S101, the potential waveform cutting section 181 (FIG. 12) cuts out a potential waveform at the points in time corresponding to the time zone during which the noise originating from the output waveform was calculated. The potential acquired at step S101 contains the noise originating from the output waveform, i.e., the electrical noise estimated at step S108.

From the potential waveform of each electrode other than the reference electrode that is acquired by the potential extraction section 170, the potential waveform cutting section 181 cuts out a potential waveform which corresponds to the output waveform in time, based on the cut-out time position information of the output waveform which is stored in the noise estimation section 150.

At step S110, the noise component subtraction section 182 subtracts the low-frequency electrical noise originating from the output waveform estimated at step S108 from the potential waveform having been cut out at step S109, and outputs the noise-free potential as the electroencephalogram.

Figure 19:
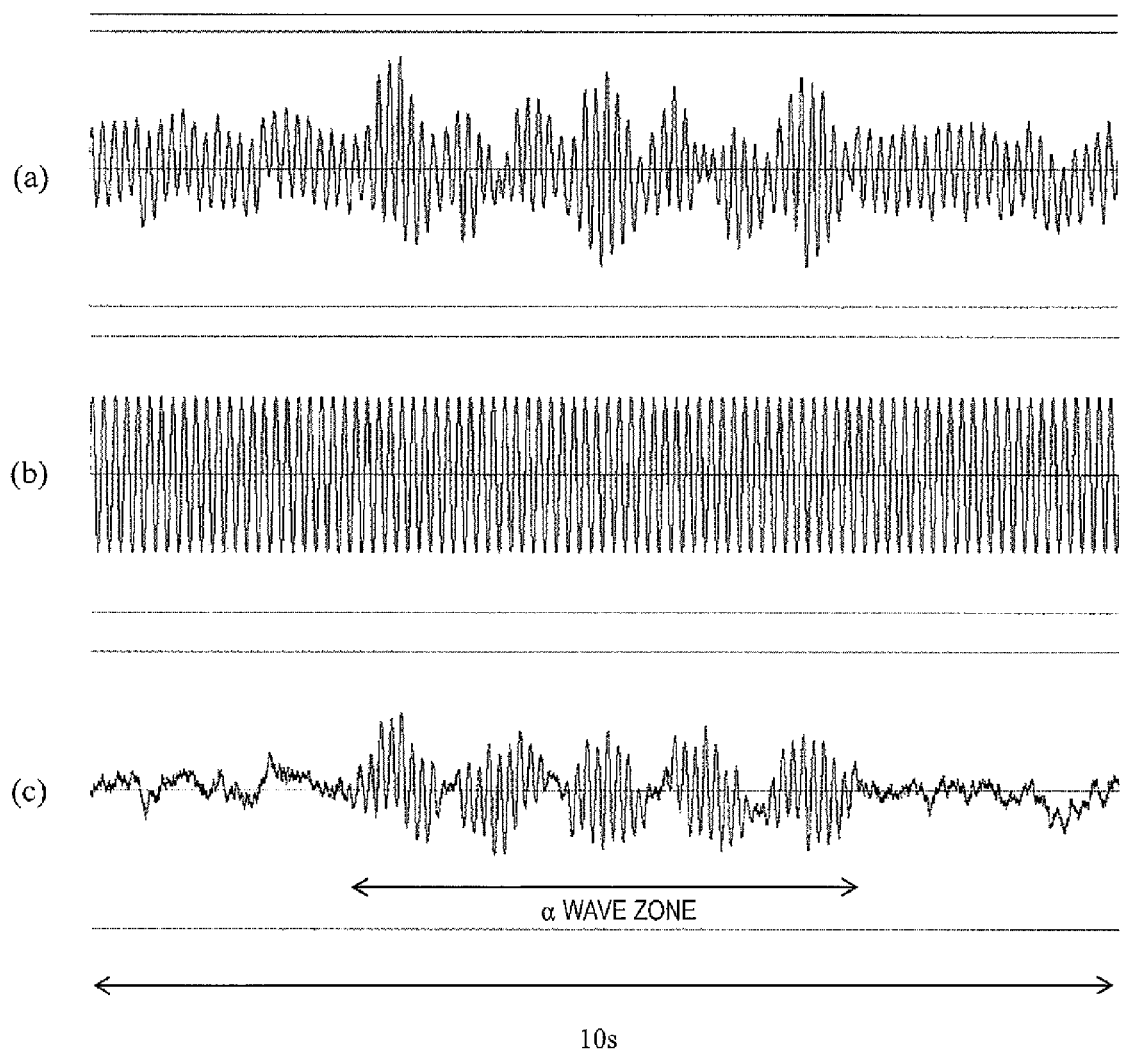
In FIG. 19, (a) is a diagram schematically showing a time waveform of an electroencephalogram containing α waves, on which a low-frequency noise is superposed; (b) is a diagram showing the waveform of the low-frequency noise which is superposed on the electroencephalogram in (a); and (c) is a diagram showing a waveform which is obtained from the waveforms of (a) and (b).

In FIG. 19, (a) schematically shows the time waveform of an electroencephalogram containing α waves, on which a low-frequency noise is superposed. In FIG. 19, (b) shows the waveform of the low-frequency noise which is superposed on the electroencephalogram in FIG. 19(a). From the waveform of FIG. 19(a) having noise superposed thereon, α waves cannot be clearly distinguished, as a result of which an α wave zone which is larger or smaller than actual may be evaluated. By estimating the noise shown in FIG. 19(b) through the procedure from step S5001 to step S108 and subtracting the noise from the waveform of FIG. 19(a), the waveform shown in FIG. 19(c) is obtained. The waveform of FIG. 19(c) indicates a characteristic fusiform α wave of 10 Hz, thus allowing the α wave zone to be accurately determined.

When a low-frequency band electrical noise originating from the acoustic output is mixed, the α waves, which is the characteristic electroencephalographical component for use as an index, cannot be separated from the noise. This may result in a situation where the noise is detected as a α wave at step S111 when actually no α waves exist, thus making it difficult to accurately grasp changes in the frequency of occurrence of α waves. Therefore, sound volume adjustment will not be correctly performed in the example of the present embodiment.

However, the electroencephalogram measurement apparatus 51 operating in the above-described manner analyzes a waveform signal which is output from an electro-acoustic transducer that is in proximity with an electrode, and estimates and removes a low-frequency electrical noise which is mixed in the potential that is recorded at the electrode. As a result, even if the electrode and the electro-acoustic transducer are in proximity and an acoustic signal is directly superposed at the electrode, an electroencephalogram can be measured without the influence from the acoustic output, thus making it possible to monitor user states, such as emotions, drowsiness, etc.

In accordance with the construction of the present embodiment, even if an electrode and an electro-acoustic transducer are disposed in proximity so as to fit within the range of a wearable device, it is possible to monitor user states based on an electroencephalogram. Since there is no need to wear any electrodes other than the wearable device itself, the user's burden associated with the wearing of devices can be reduced.

Although the present embodiment illustrates that the frequency of occurrence of α waves is employed for the monitoring of user states, this is an example. A power ratio between α waves and β waves or the like may be used, or an index based on any other electroencephalographical component may also be employed.

Embodiment 2

Figure 20:
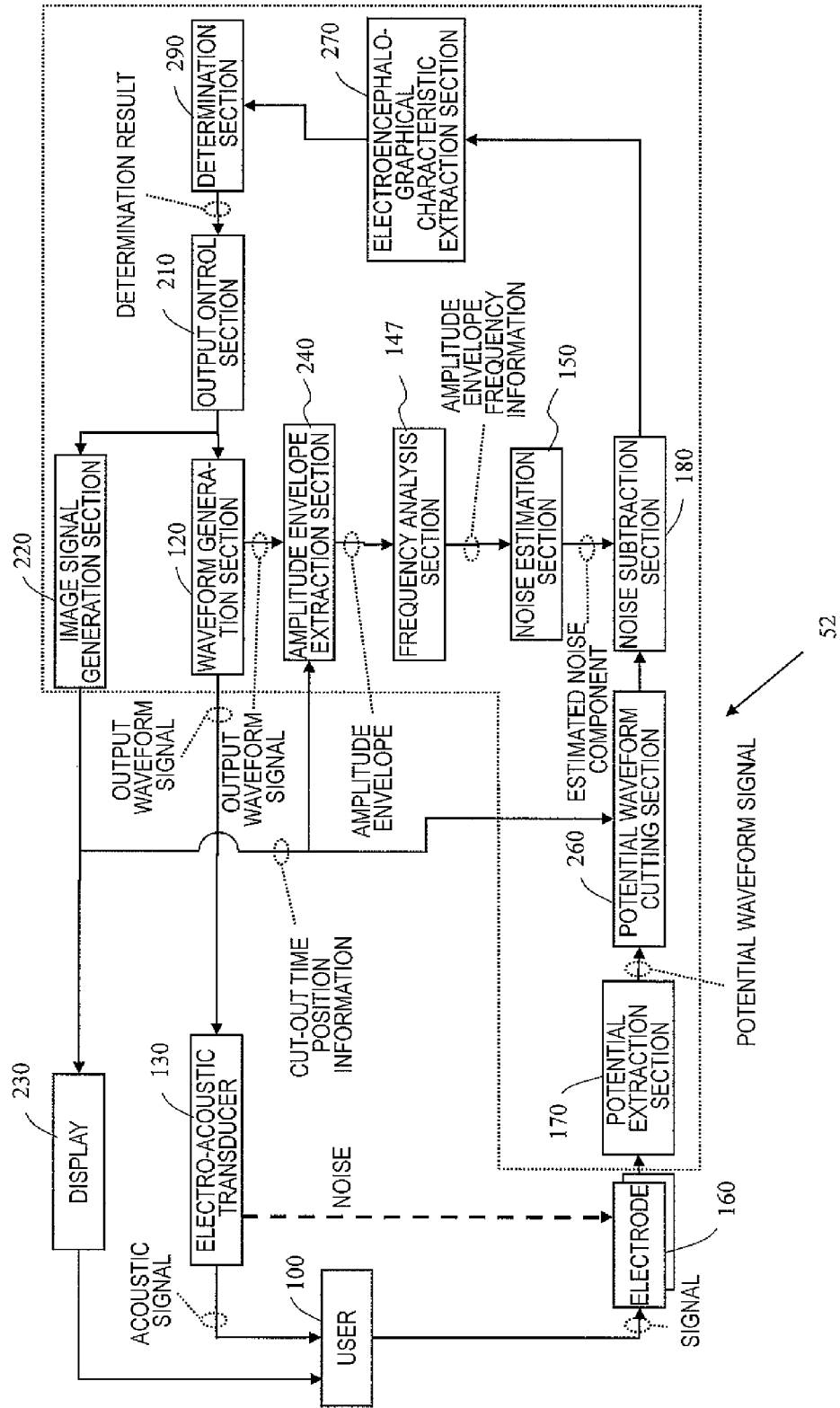
FIG. 20 is a construction diagram of an electroencephalogram measurement apparatus 52 according to Embodiment 2.
Figure 21:
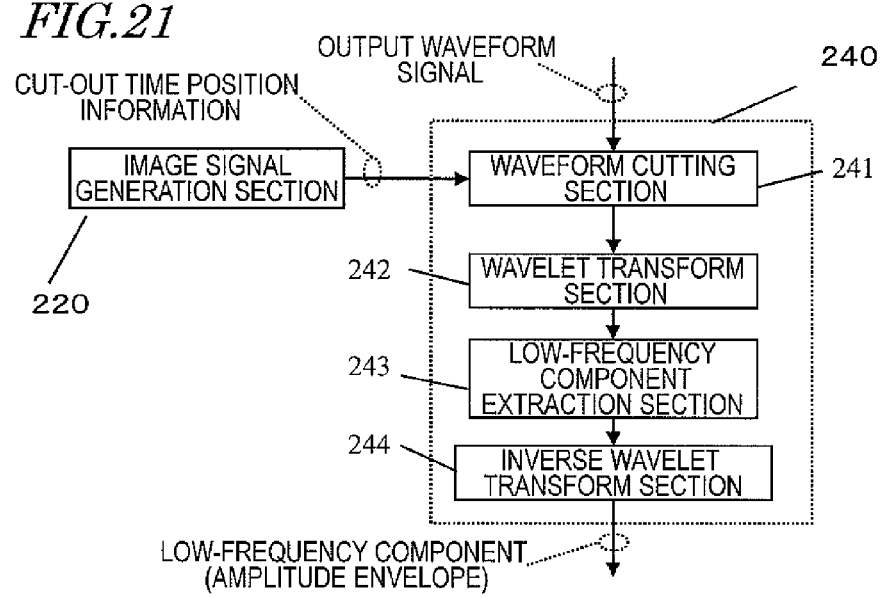
FIG. 21 is a diagram showing the detailed construction of an amplitude envelope extraction section 240.
Figure 22:
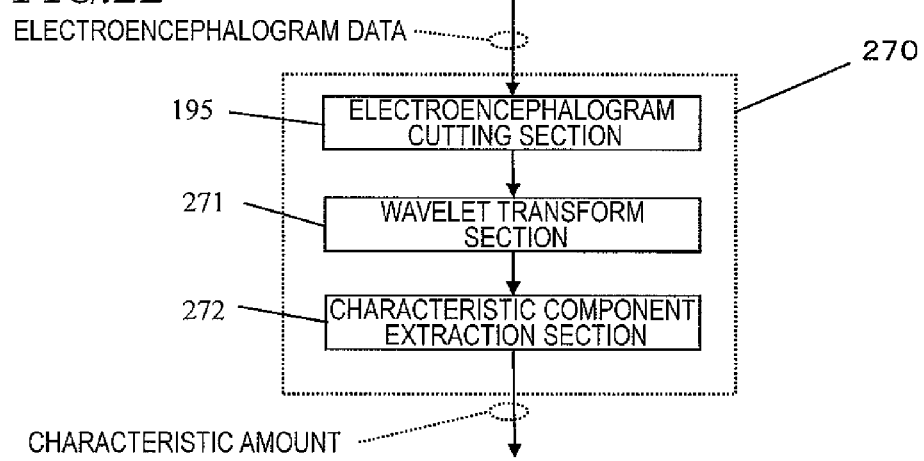
FIG. 22 is a diagram showing the detailed construction of an electroencephalographical characteristic extraction section 270.
Figure 23:
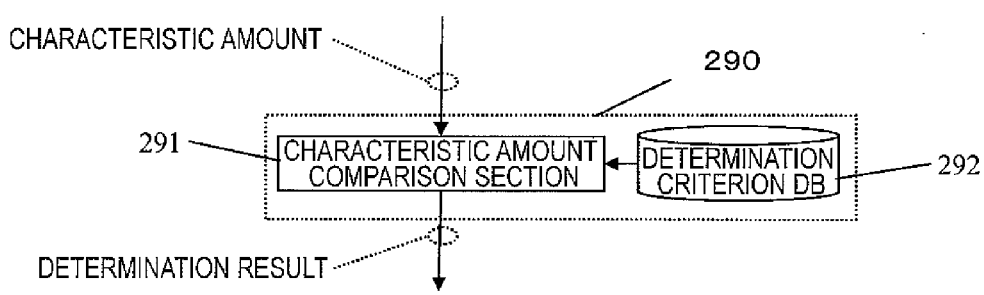
FIG. 23 is a diagram showing the detailed construction of a determination section 290.

FIG. 20 is a construction diagram showing an electroencephalogram measurement apparatus 52 of the present embodiment. FIG. 21 to FIG. 23 show the detailed constructions of constituent elements of the present embodiment. As for FIG. 20, FIG. 21, FIG. 22, and FIG. 23, elements similar to those of Embodiment 1 will be denoted by like numerals, and the descriptions thereof will be omitted.

The present embodiment illustrates an example where a user's intent is acquired with an electroencephalogram interface using an event-related potential in order to control a device. The present embodiment contemplates an HMD as shown in FIG. 6, and relies on the timing of highlighting an option on a display as a trigger for electroencephalogram cutting when acquiring an event-related potential.

The electroencephalogram measurement apparatus 52 includes an output control section 210, a waveform generation section 120, an electro-acoustic transducer 130, an amplitude envelope extraction section 240, a frequency analysis section 147, a noise estimation section 150, a display 230, an electrode section 160, a potential extraction section 170, a potential waveform cutting section 260, a noise subtraction section 180, an electroencephalographical characteristic extraction section 270, and a determination section 290.

The output control section 210 controls outputting from a device.

In accordance with a control signal from the output control section 210, the waveform generation section 120 generates a waveform of the acoustic signal to be output.

The electro-acoustic transducer 130 converts the waveform signal generated by the waveform generation section 120 into an acoustic signal for presentation to the user 100.

The amplitude envelope extraction section 240 analyzes the waveform signal generated by the waveform generation section 120 to extract a low-frequency component therefrom.

The frequency analysis section 147 applies a frequency analysis to the amplitude envelope extracted by the amplitude envelope extraction section 240.

Based on the frequency that is analyzed by the frequency analysis section 147, the noise estimation section 150 estimates an electrical noise which is caused by the low-frequency component that has been extracted by the amplitude envelope extraction section 240.

The image signal generation section 220 generates an image signal, and outputs the image signal in accordance with a control signal from the output control section 210. The image signal generation section 220 sends cut-out time position information to the potential waveform cutting section 260. The cut-out time position information is sent at the moment of highlighting an option, for example. This indicates the timing of highlighting the option. This cut-out time position information is to be utilized for cutting out an electroencephalogram when acquiring an event-related potential.

The display 230 displays an image. The display 230 is a liquid crystal display, for example.

The electrode section 160 is attached to the periphery(s) of one or both of the ears of the user 100.

The potential extraction section 170 extracts potential data. This potential data is also referred to as a potential waveform signal.

In accordance with the cut-out time position information which is output from the image signal generation section 220, the potential waveform cutting section 260 cuts out a potential waveform from the potential data having been extracted by the potential extraction section 170.

For the potential waveform having been cut out by the potential waveform cutting section 260, the noise subtraction section 180 performs a noise counteracting process of reducing the influence of the electrical noise originating from the output waveform as estimated by the noise estimation section 150.

From the electroencephalogram having been processed by the noise subtraction section 180, the electroencephalographical characteristic extraction section 270 extracts a characteristic amount in the electroencephalogram to be used for determination.

Based on the characteristic amount extracted by the electroencephalographical characteristic extraction section 270, the determination section 290 determines the user's intent.

Among the above constituent elements, a CPU and a memory is used to implement a part of the waveform generation section 120, the amplitude envelope extraction section 240, the frequency analysis section 147, the noise estimation section 150, the noise subtraction section 180, the output control section 210, the image signal generation section 210, the potential waveform cutting section 250, the electroencephalographical characteristic extraction section 270, the determination section 290, and/or the potential extraction section 170.

FIG. 21 shows the detailed construction of the amplitude envelope extraction section 240. The amplitude envelope extraction section 240 includes a waveform cutting section 241, a wavelet transform section 242, a low-frequency component extraction section 243, and an inverse wavelet transform section 244.

FIG. 22 shows the detailed construction of the electroencephalographical characteristic extraction section 270. The electroencephalographical characteristic extraction section 270 includes an electroencephalogram cutting section 195, a wavelet transform section 271, and a characteristic component extraction section 272.

The electroencephalographical characteristic extraction section 270 extracts components that are contained in the electroencephalogram waveform. The data of the extracted components is utilized for a process by the determination section 290 of determining whether a P300 component of the event-related potential is contained or not.

As used in the present embodiment, a. "P300 component of the event-related potential" means a characteristic positive component that appears in the electroencephalographical component at a latency of about 300 ms based on the point of highlighting a menu item as a starting point, for example.

The electroencephalogram cutting section 195 cuts out a potential waveform spanning a time range that is necessary for the measurement. Specifically, a zone of −100 milliseconds to 600 milliseconds based on the timing of highlighting is cut out, for example.

The wavelet transform section 271 subjects the continuous electroencephalogram waveform that has been cut out to a time-frequency separation via wavelet transform. From the time-frequency separated data, the characteristic component extraction section 272 extracts the necessary time zone and frequency band as a characteristic component, and sends it to the determination section 290. For example, it is a time zone from 200 ms to 400 ms (300±100 ms) based on the point of highlighting a menu item as a starting point.

FIG. 23 shows the detailed construction of the determination section 290. The determination section 290 includes a characteristic amount comparison section 291 and a determination criteria database 292.

The determination criteria database 292 is constructed on a memory, for example. In advance, the determination criteria database 292 stores the data of the characteristic component which is obtained by subjecting the electroencephalogram waveform containing the typical P300 component to a wavelet transform as described above and the data of a characteristic component which is obtained by subjecting an electroencephalogram waveform not containing the P300 component to a wavelet transform. Each of these is also referred to as "reference data".

The characteristic amount comparison section 291 calculates a similarity level by comparing the characteristic component received from the characteristic component extraction section 272 against the reference data stored in the determination criteria database 292. Then, based on the calculated similarity level, the characteristic amount comparison section 291 determines whether the received characteristic component is closer to the data containing the P300 characteristic component or the data not containing the P300 characteristic component.

FIG. 24 is a flowchart showing the procedure of processing by the electroencephalogram measurement apparatus 52 of the present embodiment. Hereinafter, with reference to FIG. 24, the operation of the electroencephalogram measurement apparatus 52 will be described.

At step S101, the potential extraction section 170 determines a potential difference between a predetermined one reference electrode among the electrodes in the electrode section 160 and each measurement electrode. The reference electrode may be placed at one of the mastoids, for example.

At step S201, the potential waveform cutting section 260 determines whether the output control section 210 is issuing an instruction for presentation of information to become a trigger for event-related potential measurement. Specifically, the presentation of information to become a trigger may be an instruction for the image signal generation section 220 to generate an image for drawing attention of the user by highlighting one item in a menu list that is being indicated on the display as an image, for example.

Figure 25A:
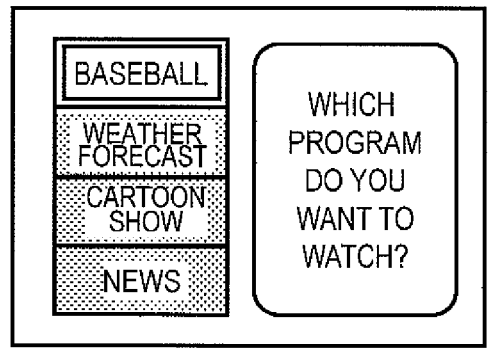
FIGS. 25A to 25D are diagrams showing exemplary screen indications of a menu list when a menu selection is to be made by using an electroencephalogram interface.
Figure 25B:
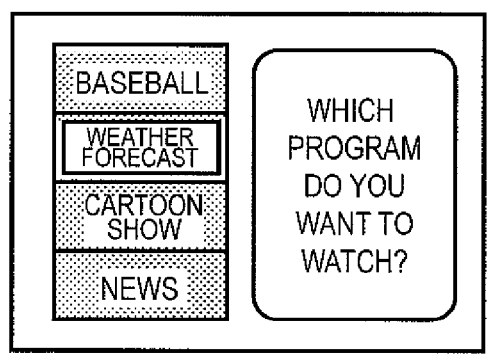
Figure 25C:
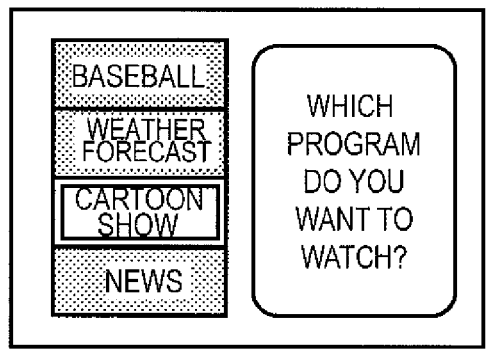
Figure 25D:
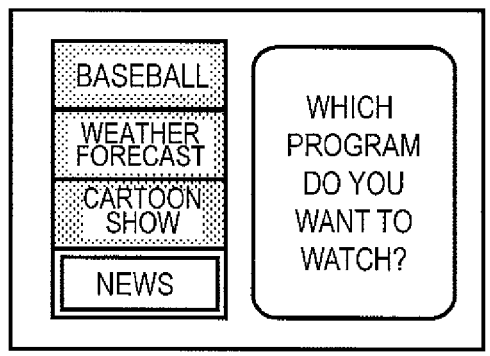

FIGS. 25A to 25D illustrate exemplary screen indications of a menu list when a menu selection is to be made by using an electroencephalogram interface. For example, as shown in FIGS. 25A to 25D, while a selectable menu (i.e., a screen indicating "baseball", "weather forecast", "cartoon show", and "news" in the example of FIGS. 25A to 25D) is being displayed, only one item is highlighted in the menu list. FIGS. 25A to 25D show examples where the respective items of "baseball", "weather forecast", "cartoon show", and "news" are highlighted. In FIG. 25A, for example, "baseball" is highlighted while the other three items are not highlighted.

Based on an instruction to generate an image, the image signal generation section 220 generates image information, and further outputs trigger timing (which in the specific example of the present embodiment is the timing of highlighting an option) to the potential waveform cutting section 260 and the amplitude envelope extraction section 240.

At step S202, based on the timing of highlighting which has been set at step S201, the potential waveform cutting section 260 cuts out a potential waveform spanning a time range that is necessary for the measurement, from the potential waveform extracted by the potential extraction section 170. For example, the potential waveform cutting section 260 may cut out a zone from −100 milliseconds to 600 milliseconds based on the timing of highlighting.

At step S102, it is determined whether there is an instruction for acoustic output from the acoustic output control section 110.

If step S102 finds that there is an instruction for acoustic output, i.e., following Yes from step S102, the process proceeds to step S1000. At step S1000, a noise reduction process is performed because the potential difference which was acquired at step S101 and cut out at step S202 presumably contains a low-frequency electrical noise originating from the output waveform.

On the other hand, if step S102 finds that there is no instruction for acoustic output, i.e., following No from step S102, the process proceeds to step S203. At step S203, the potential waveform which was acquired at step S101 and cut out at step S202 is regarded as the electroencephalogram (event-related potential), and no noise reduction process is performed.

Figure 26:
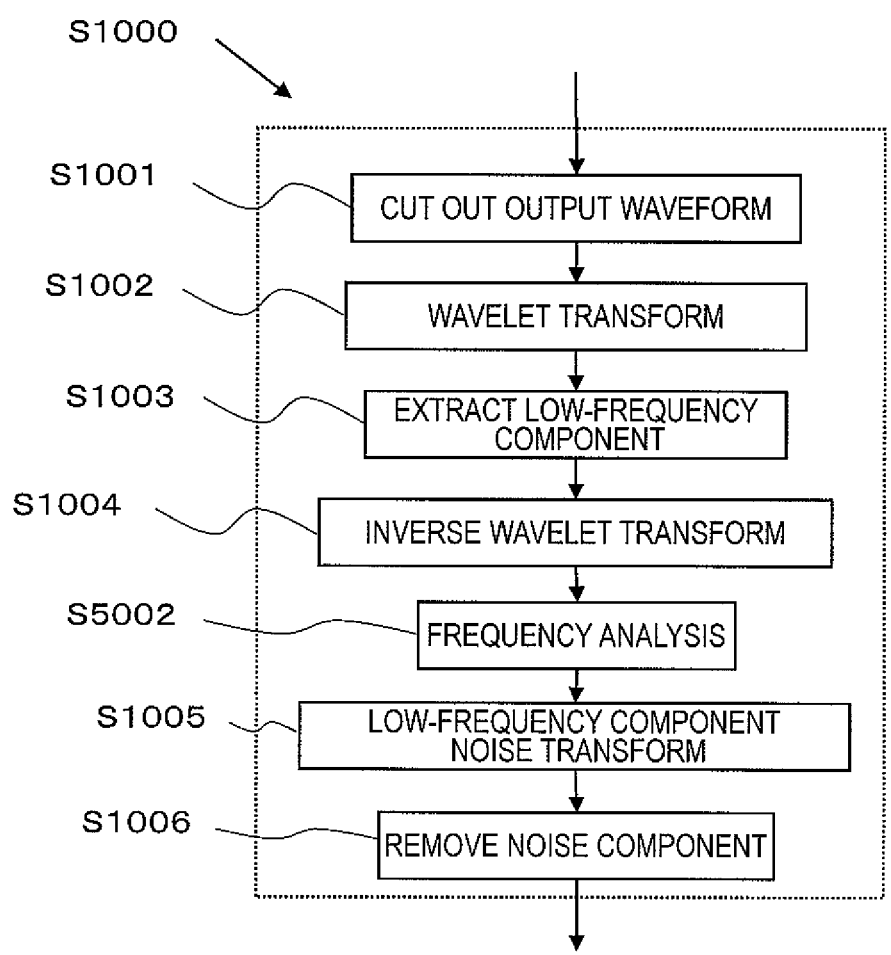
FIG. 26 is a flowchart showing the details of step S1000 in FIG. 24.

FIG. 26 shows the details of step S1000. Step S1000 is executed in order to remove the electrical noise originating from the output waveform in the present embodiment.

Step S1000 is carried out through a procedure from S1001 to S1006 shown in FIG. 26.

At step S1001, based on the timing of highlighting which is output from the image signal generation section 220, the waveform cutting section 241 cuts out a waveform signal corresponding to the time range during which an electroencephalogram is to be measured, from the waveform signal generated by the waveform generation section 120. Specifically, from the output waveform signal, a waveform which is output at a time corresponding to the time range of the potential waveform having been cut out at step S202, or a waveform which is output in a time range containing the corresponding time is cut out.

At step S1002, the wavelet transform section 242 subjects the waveform having been cut out at step S1001 to a wavelet transform to separate it into bands of different frequency components.

At step S1003, the low-frequency component extraction section 243 extracts a component of 30 Hz or less. The component extracted here is a low-frequency component which is expressed in the time-frequency domain. This low-frequency component contains the amplitude envelope component.

At step S1004, the inverse wavelet transform section 244 subjects the low-frequency component extracted at step S1003 to an inverse wavelet transform, and generates a time waveform of the extracted low-frequency component. Through this process, the amplitude envelope of the output signal generated by the waveform generation section 120 can be extracted as a time waveform. Note that the inverse wavelet transform is an opposite process of the wavelet transform, and is a process in which time-frequency separated data is restored into waveform data in the time domain. Since this process is well known, detailed descriptions thereof are omitted.

At step S5002, the frequency analysis section 147 performs a frequency analysis of the amplitude envelope extracted at step S5001 as to its envelope profile. An instantaneous frequency of the envelope, i.e., low-frequency component (or low-range component), is obtained by a procedure of applying a Hilbert transform to the low-range component, calculating an instantaneous angular velocity for each sampling point, and converting the angular velocities into a frequency based on the sampling period, for example. Alternatively, by utilizing the wavelet coefficients from the wavelet transform performed at step S1002, within the low-frequency component extracted at step S1003, the frequency having the largest energy for each sampling point may be regarded as a frequency of the amplitude envelope.

At step S1005, based on the waveform generated at step S1004, the noise estimation section 150 estimates the low-frequency electrical noise originating from the output waveform as a time waveform, similarly to step S108 of Embodiment 1. From a transform function which is stored in the signal-noise transform function storage section 151, the noise estimation process section 152 determines a coefficient corresponding to the instantaneous frequency of the time waveform of the low-frequency component. Then, by multiplying each value of the time waveform of the low-frequency component by that coefficient, the noise estimation process section 152 estimates the low-frequency electrical noise originating from the output waveform as a time waveform.

At step S1006, from the potential waveform cut out at step S202, the noise component subtraction section 182 subtracts the low-frequency electrical noise originating from the output waveform estimated at step S1005, and outputs the noise-free potential as the electroencephalogram.

At step S203, the wavelet transform section 271 applies a wavelet transform to the event-related potential cut out at step S202 or the event-related potential cut out at step S202 and subjected to a noise reduction process at step S1000. As a result, the event-related potential undergoes time-frequency separation. By specifying the electroencephalogram in terms of characteristic amounts of time and frequency, it becomes possible to select and extract the time zone and/or the frequency band in which the characteristic signal of the electroencephalogram occurs when making a selection.

At step S204, from the result of wavelet transform at step S203, the characteristic component extraction section 272 cuts out only a region concerning the electroencephalographical characteristic signal. Specifically, a region of frequencies of 5 Hz or less is cut out, for example. As a result of this, the frequency band of P300, which is the main component of the event-related potential, is extracted; and the electrooculographic potential and electromyographic potential, which will mainly be recorded in a frequency band of 5 Hz or higher, can be removed.

The characteristic component extraction section 272 cut outs the information in a zone from 200 ms to 400 ms after highlighting as an electroencephalographical characteristic component. In other words, in the example of the present embodiment, data sampling points contained in the region from 200 ms to 400 ms and at frequencies of 5 Hz or less are extracted. This is because P300 is a potential change to be observed after the lapse of about 300 ms since a trigger.

At step S205, the characteristic component extraction section 272 combines the data sampling points extracted at step S204 into a single data representing the electroencephalographical characteristic component, which is defined as the electroencephalographical characteristic amount.

At step S206, the characteristic amount comparison section 291 in the determination section 290 determines a similarity level between the characteristic amount generated at step S205 and the reference data stored in the determination criteria database 292, and determines whether the measured event-related potential corresponds to an intent of selecting the highlighted item or an intent of not selecting the highlighted item.

The reference data stored in the determination criteria database 292 are previously-provided electroencephalographical characteristic amounts. The following is the manner in which the inventors have obtained the reference data. First, each one of a plurality of users is asked to clarify in advance which item (option) among a plurality of items he or she is going to select. Then, an electroencephalogram interface experiment is conducted by employing the same electrode positions as those employed when actually using an electroencephalogram interface. Then, as the plurality of items are consecutively highlighted, each user is supposed to make a selection in his or her mind, and the electroencephalograms (event-related potentials) at such times are measured. The recorded event-related potential data is subjected to a wavelet transform similarly to steps S203 to S205 described above, and sampling points in the electroencephalographical characteristic region from 200 ms to 400 ms and at frequencies of 5 Hz or less are extracted and combined, whereby electroencephalographical characteristic amounts are obtained. Such electroencephalographical characteristic amounts are categorized into those pertaining to the item to be selected and those pertaining to any item not to be selected (unselected item). What describes the association between the different types of items and the electroencephalographical characteristic amounts is the reference data. The determination criteria database 292 retains the reference data obtained in this manner.

Note that, as described above, the reference data may be generated based on the electroencephalograms of an unspecified plurality of people; or, in the alternative, the particular user 100 utilizing the electroencephalogram interface may go through an advance learning process as described above, and reference data utilizing the electroencephalogram of the user 100 may be generated.

The characteristic amount comparison section 291 calculates a similarity level which indicates how similar the electroencephalographical characteristic amount generated at step S205 is to the waveform pertaining to the case where an item of selection becomes highlighted. Specifically, the characteristic amount comparison section 291 classifies the reference data stored in the determination criteria database 292 into the two groups of waveforms associated with items to be selected (correct waveforms) and waveforms not to be selected (incorrect waveforms). Then, the characteristic amount comparison section 291 calculates distances between a measured electroencephalographical characteristic amount and the electroencephalographical characteristic amounts of the correct waveform group and the incorrect waveform group, thus calculating similarity levels with respect to the correct waveform group and the incorrect waveform group. In the present embodiment, as a method of similarity level calculation, a linear discriminant technique is employed, and a posterior probability that the characteristic amount obtained at step S205 belongs to the correct waveform group or the incorrect waveform group is defined as a similarity level.

Note that the aforementioned method of similarity level calculation is one example. Other calculation methods may employ techniques such as support vector machine or neural network techniques. These techniques calculate a measure of how much closer a measured electroencephalographical characteristic amount is to the correct waveform group from a border line between the correct waveform group and the incorrect waveform group (i.e., distance from the border line). A similarity level between an electroencephalographical characteristic amount and the correct waveform group may be calculated on this basis.

At step S207, the characteristic amount comparison section 291 compares the similarity level to the correct waveform group and the similarity level to the incorrect waveform group determined at step S206. If the similarity level to the correct waveform group is greater than the similarity level to the incorrect waveform group and yet the similarity level to the correct waveform group is equal to or greater than a predetermined threshold value and the similarity level to the incorrect waveform group is equal to or less than a predetermined threshold value, the characteristic amount comparison section 291 determines that the measured event-related potential represents an intent of selecting the highlighted item. The predetermined threshold values may be 0.7 or more for the similarity level to the correct waveform group, and 0.3 or less for the similarity level to the incorrect waveform group, for example.

In the present embodiment, determination of an intent of selection is performed for each highlight. Alternatively, after highlighting all options and acquiring an event-related potential for the highlighting of each option, the option that has produced a high similarity level to the correct waveform group may be determined as the option intended by the user. For example, after displaying the four indications of FIGS. 25A to 25D and acquiring the event-related potentials therefor, the similarity levels of the event-related potentials for the respective options may be compared, and the option that has produced the highest similarity level to the correct waveform group may be chosen. Each option may be highlighted a plurality of times, in which case a method of generating an arithmetic mean waveform for each option and determining a similarity level to the correct waveform group may be adopted. Or, for the plurality of times of highlighting of each option, a similarity level to the correct waveform group may be obtained for each highlight, and a typical value (e.g., a mean or median) for the plurality of highlights may be utilized for making a comparison of similarity levels to the correct waveform group among options.

At step S207, it is determined whether the similarity level to the correct waveform group is greater than the similarity level to the incorrect waveform group and yet the similarity level to the correct waveform group is equal to or greater than the predetermined threshold value and the similarity level to the incorrect waveform group is equal to or less than the predetermined threshold value or not. If all of these conditions are satisfied, i.e., following Yes from step S207, the output control section 210 executes the item at step S208 because the highlighted item is presumably the selected one. Specifically, the song that has so far been played back may cease to be output, and a song that appears highlighted on the menu list may now begin to be played back, for example.

On the other hand, if step S207 finds that any of the aforementioned conditions is not satisfied, i.e., following No from step S207, the operation is ended.

As described above, the electroencephalogram measurement apparatus 52 analyzes a waveform signal which is output from an electro-acoustic transducer that is in proximity to an electrode, and estimates and removes a low-frequency electrical noise which is mixed in the potential that is recorded at the electrode. As a result, even if the electrode and the electro-acoustic transducer are in proximity, without the influence from the acoustic output, an electroencephalogram can be measured for use in an electroencephalogram interface. Consequently, even if the electrode and the electro-acoustic transducer are disposed in proximity so as to fit within the range of a wearable device, it is possible to utilize an electroencephalogram interface. Since there is no need to wear any electrodes other than the wearable device itself, the user's burden associated with the wearing of devices can be reduced.

Although it is illustrated that the image signal generation section 220 outputs cut-out time position information when an option becomes highlighted, this is an example. After highlighting, the image signal generation section 220 may output information indicating the point of highlighting as the cut-out time position information. In this case, the amplitude envelope extraction section 240 and the potential waveform cutting section 260 may each determine a time zone in which to cut out a necessary waveform from the output waveform signal or from the potential waveform signal, respectively.

Moreover, it is illustrated that the amplitude envelope extraction section 240 performs a wavelet transform at step S203. Instead, the amplitude envelope extraction section 240 may perform a Fourier transform. In this case, the wavelet transform section 242 and the inverse wavelet transform section 244 of FIG. 21 should read as a Fourier transform section performing a Fourier transform and an inverse Fourier transform section performing an inverse Fourier transform, respectively.

First Variant of Embodiment 2

Embodiment 2 illustrates a case where an image output by the display 230 is used as an output for which an electroencephalogram is to be measured. However, any signal presentation to senses other than the visual sense may be employed, e.g., presentation of a tactile sensation to the tactile sense, presentation of an olfactory sensation by spraying a smelling substance to the nose, or presentation of a gustatory sensation by presenting a tasting substance to the tongue.

Figure 27:
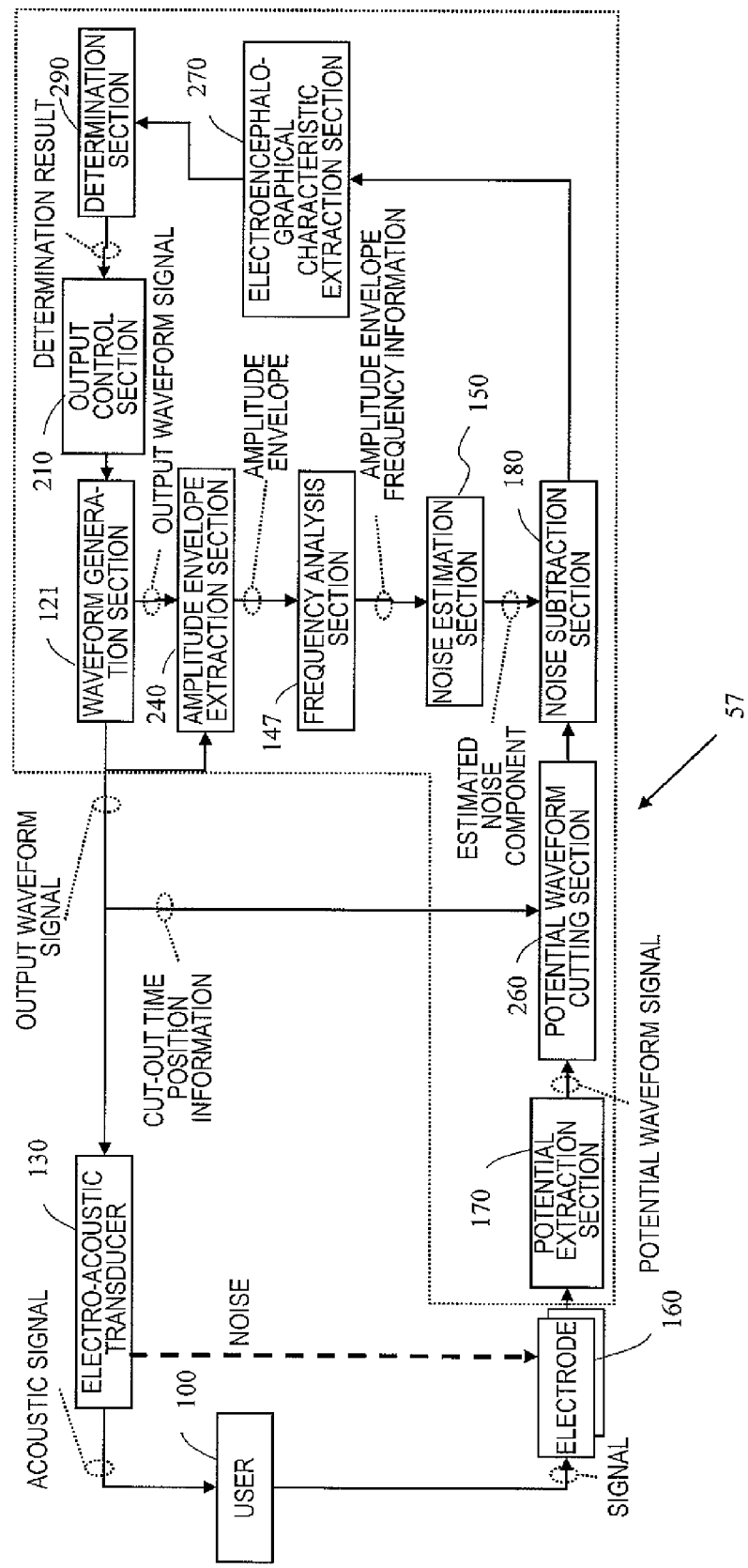
FIG. 27 is a construction diagram showing an electroencephalogram measurement apparatus 57 according to a first variant of Embodiment 2.

For example, outputting of an acoustic signal may be used as a trigger, instead of using the display 230. For instance, in the case of a music player utilizing headphones (e.g., that shown in FIG. 1), the timing of song switching may be utilized as a trigger, as in the "zapping" of songs, where one song is presented after another consecutively. With reference to FIG. 27, the construction of an electroencephalogram measurement apparatus in such an example will be described.

FIG. 27 is a construction diagram of an electroencephalogram measurement apparatus 57 according to a first variant of the present embodiment. By using an electro-acoustic transducer 130 similar to that of Embodiment 1, the electroencephalogram measurement apparatus 57 presents a plurality of songs, cuts out an electroencephalogram with the timing of switching between songs as a trigger, and acquires an event-related potential. Since the electroencephalogram measurement apparatus 57 determines a timing of cutting out an electroencephalogram based on songs alone, it may lack the display 230 which is provided in the electroencephalogram measurement apparatus 52 (FIG. 20) of Embodiment 2. Among the constituent elements of the electroencephalogram measurement apparatus 57, constituent elements having the same functions as those of the electroencephalogram measurement apparatus 52 (FIG. 20), for example, are denoted by the same reference numerals; and the descriptions of any constituent element that are common between them will be omitted. Note that the constituent elements surrounded by the broken line may be implemented by a CPU and/or a memory.

Generally, the processes shown in FIG. 24 and FIG. 26 are executed as the processes by the electroencephalogram measurement apparatus 57 of this variant. The differences consist only in the processes related to the use of the timing of switching between songs as a trigger. Hereinafter, an example thereof will be described.

As shown in FIG. 27, in addition to generating an output waveform, the waveform generation section 121 outputs a timing of song switching to the potential waveform cutting section 260 and the amplitude envelope extraction section 240. This process corresponds to the process in which the image signal generation section 220 outputs a timing of highlighting (step S201 in FIG. 24), described above in Embodiment 2.

At step S202, based on the timing of song switching which is output from the waveform generation section 121, the potential waveform cutting section 260 cuts out a potential waveform spanning a time range that is necessary for the measurement, from the potential waveform extracted by the potential extraction section 170. Moreover, instead of a timing of highlighting which is output from the image signal generation section 220, the waveform cutting section 241 acquires the timing of song switching which is output from the waveform generation section 121.

At step S1001, based on the timing of song switching, the waveform cutting section 241 cuts out a waveform which is output at a time corresponding to the time range of the potential waveform having been cut out at step S202, from the waveform signal generated by the waveform generation section 120. Alternatively, from the output waveform signal, the waveform cutting section 241 cuts out a waveform which is output in a time range containing the corresponding time. Through this process, an electroencephalogram interface similar to that of Embodiment 2 can be constructed even in a wearable device which lacks a display, e.g., a music player.

In the present embodiment, the electroencephalographical characteristic extraction section 270 employs wavelet-based time-frequency separation at step S203. However, any other method may be adopted, e.g., a method employing a time-frequency separation based on the Fourier transform, or a method using latency and amplitude based on peak extraction of electroencephalographical components.

Second Variant of Embodiment 2

Next, a second variant of the electroencephalogram measurement apparatus of the above-illustrated present embodiment will be described. In this variant, a visual stimulation using a display is adopted as a trigger, a different processing from the process of Embodiment 2 is performed.

Figure 28:
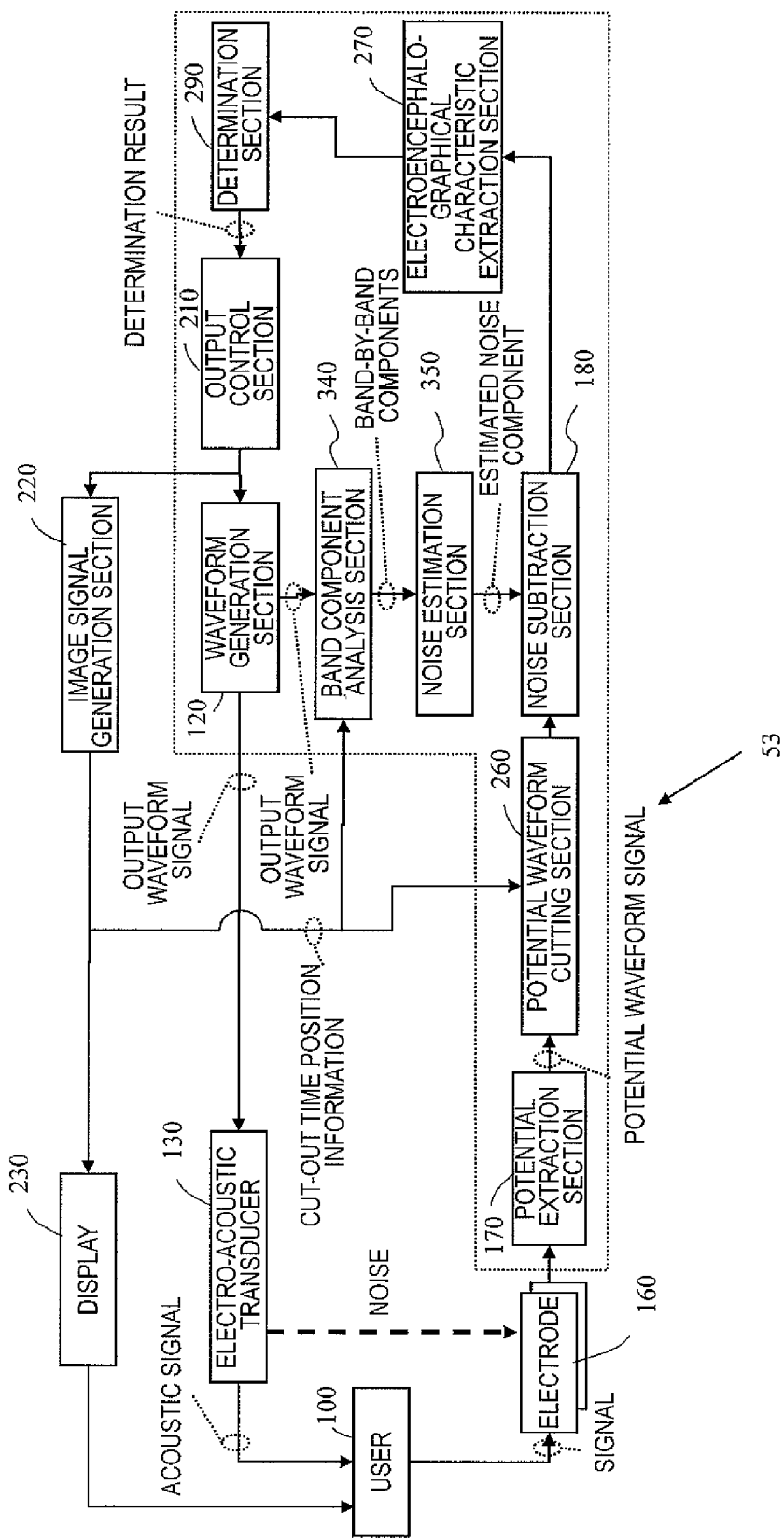
FIG. 28 is a construction diagram showing an electroencephalogram measurement apparatus 53 according to a second variant of Embodiment 2.

FIG. 28 is a construction diagram of an electroencephalogram measurement apparatus 53 according to second variant of the present embodiment.

As in Embodiment 2 above, this variant also assumes that a user's intent is acquired with an electroencephalogram interface using an event-related potential in order to control a device.

This example contemplates an HMD as shown in FIG. 6, and relies on the timing of highlighting an option on the display as a trigger for electroencephalogram cutting when acquiring an event-related potential.

In the electroencephalogram measurement apparatus 53 of this example, a band component analysis section 340 is provided instead of the amplitude envelope extraction section 240 which is provided in the electroencephalogram measurement apparatus 52 of Embodiment 2. Moreover, a noise estimation section 350 is provided instead of the noise estimation section 150. Otherwise, the construction is the same. The constituent elements surrounded by the broken line are similarly implementable by a CPU and/or a memory.

The band component analysis section 340 and the noise estimation section 350 are implemented by a CPU and a memory, as are the amplitude envelope extraction section 240 and the noise estimation section 150 of Embodiment 2.

The electroencephalogram measurement apparatus 53 includes an output control section 210, a waveform generation section 120, an electro-acoustic transducer 130, a band component analysis section 340, a noise estimation section 350, an image signal generation section 220, a display 230, an electrode section 160, a potential extraction section 170, a potential waveform cutting section 260, a noise subtraction section 180, an electroencephalographical characteristic extraction section 270, and a determination section 290.

The band component analysis section 340 analyzes a waveform signal which is generated by the waveform generation section 120, and separates it into band-by-band components.

FIG. 29 shows the detailed construction of the band component analysis section 340. The band component analysis section 340 includes a waveform cutting section 241, a wavelet transform section 242, and a band component splitting section 343.

For the band-by-band components generated by the band component analysis section 340, the noise estimation section 350 in FIG. 28 calculates an electrical noise component for each band and thereafter combines the band-by-band components to generate a waveform, thereby estimating an electrical noise.

FIG. 30 shows the detailed construction of the noise estimation section 350. The noise estimation section 350 includes a band component calculation section 351, a table of signal-noise transform coefficients 352, and an inverse wavelet transform section 353. The table 352 of signal-noise transform coefficients included in the noise estimation section 350 is implemented by a memory.

The processing by the electroencephalogram measurement apparatus 53 will be described with reference to FIG. 31 below, thereby also describing the band component analysis section 340 and the noise estimation section 350. In FIG. 28 to FIG. 30, portions which are identical to those in Embodiment 2 will be denoted by the same reference numerals, and the descriptions thereof will be omitted.

The operation of the electroencephalogram measurement apparatus 52 of this variant is identical to what is illustrated in FIG. 24 except for step S1000. In this variant, too, the timing of highlighting an option is used as an example of trigger information.

Furthermore, step S1000 is also similar to that in the procedure of processing by Embodiment 2 except that the operation from step S1003 to step S1005 in FIG. 26 is replaced by the operation from step S2003 to step S2006. Therefore, descriptions of the other operations may be conveniently omitted.

Figures 31, 32:
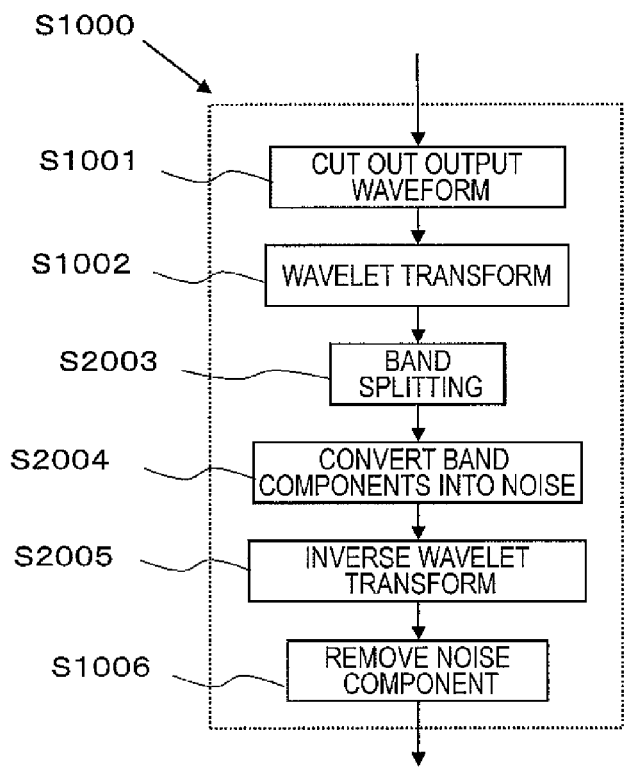
FIG. 31 is a flowchart showing a procedure of processing at step S1000 in FIG. 24 by the electroencephalogram measurement apparatus 53.
FIG. 32 is a diagram showing an example of a table 352 of signal-noise transform coefficients.

FIG. 31 is a flowchart showing the procedure of processing at step S1000 by the electroencephalogram measurement apparatus 53 of this variant. In this variant, too, the process of step S1000 is executed in order to remove electrical noise originating from the output waveform.

At step S2003, the band component splitting section 343 splits the frequency-by-frequency components that have been separated at step S1002 into bands. Specifically, as illustrated in FIG. 32, the components may be split into the following six bands, for example: 0 Hz to 2 Hz; 2 Hz to 4 Hz; 4 Hz to 8 Hz; 8 Hz to 16 Hz; 16 Hz to 32 Hz; and 32 Hz or higher.

At step S2004, as shown in FIG. 30, the band component calculation section 351 refers to a table 352 of signal-noise transform coefficients to determine a transform coefficient corresponding to the component power of each frequency band of the output waveform generated at step S2003. FIG. 32 shows an example of the table 352 of signal-noise transform coefficients. It can be seen from FIG. 32 that coefficients are set in accordance with bands and powers (unit: dB).

Furthermore, the band component calculation section 351 multiplies the data of the band-by-band components of the output waveform by the determined transform coefficients, thus determining band-by-band components of the electrical noise. Specifically, the power of a given band component of the output waveform is indicated in decibels, as a ratio to a reference value which is defined by an input limit value of 90 dB, for example. Although the table of signal-noise transform coefficients is to be generated on the basis of a signal-noise transform function as exemplified in FIG. 16 of Embodiment 1, it should be determined through actual measurements because factors other than the band components of the signal, e.g., the distance between the electrode and the electro-acoustic transducer, will also affect the ratios of signal-to-noise transform.

At step S2005, the inverse wavelet transform section 353 conducts an inverse wavelet transform to combine the band-by-band components determined at step S2004, thus generating the time waveform of an estimated electrical noise.

At the last step S1006 following the above processes, the noise component subtraction section 182 subtracts the electrical noise originating in the output waveform (as estimated at step S2005) from the potential waveform having been cut out at step S202, and outputs the noise-free potential as the electroencephalogram.

The subsequent processes from steps S203 to S208 (FIG. 24) are generally the same as those of Embodiment 2 in principle, the difference being a part of the process of step S204.

At step S204, the characteristic component extraction section 272 cuts out only a region concerning the electroencephalographical characteristic signal from the result of wavelet transform at step S203. Specifically, the characteristic component extraction section 272 extracts data sampling points contained in the region from 200 ms to 400 ms and at frequencies of 5 Hz or less, in order to extract a characteristic feature of the P300 component, for example. Step S205 and the subsequent steps are identical to what was described in Embodiment 2.

Thus, the electroencephalogram measurement apparatus 53 according to this variant of Embodiment 2 attain the same effects as those of the electroencephalogram measurement apparatus 52 of Embodiment 2.

Embodiment 3

Figure 33:
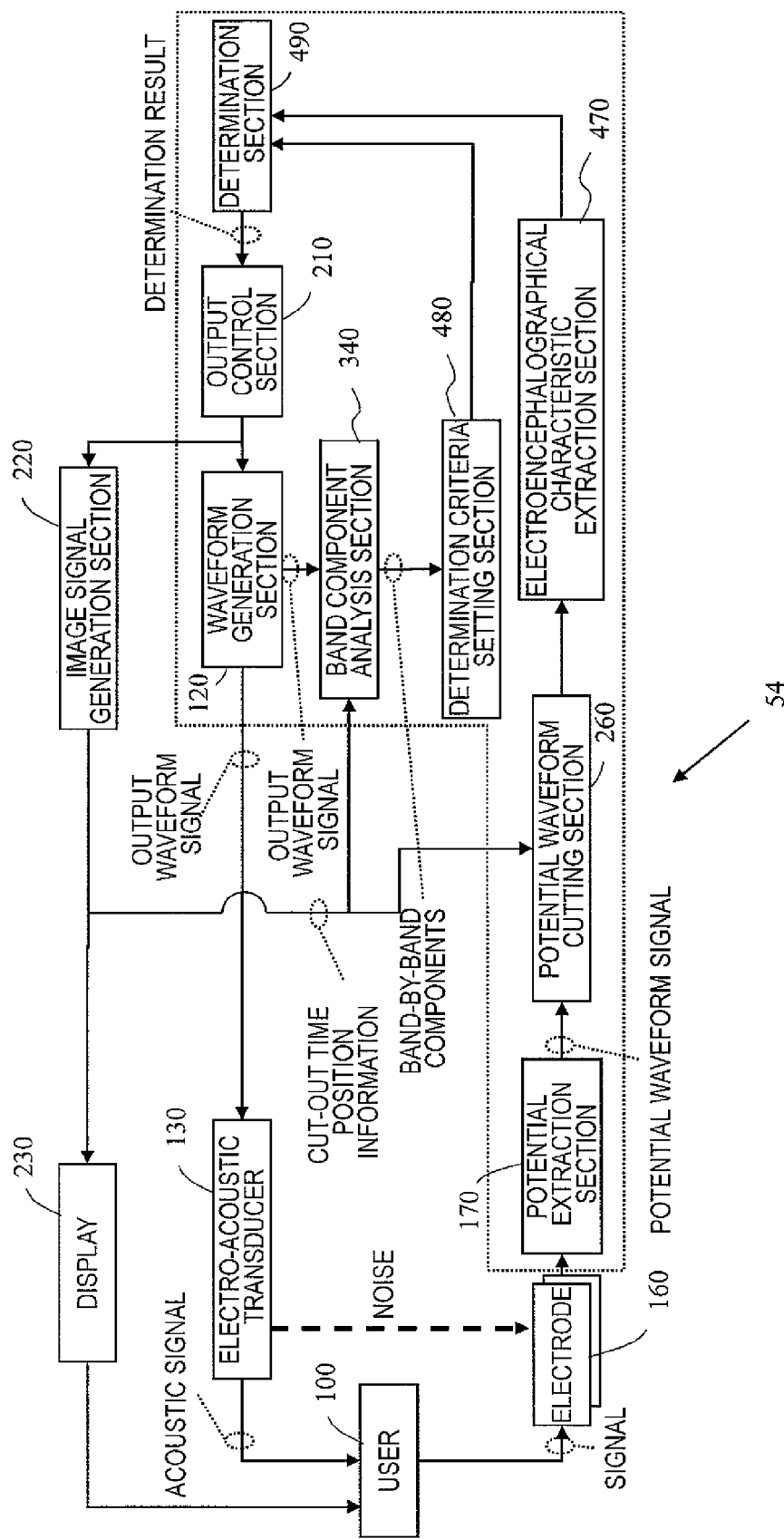
FIG. 33 is a construction diagram of an electroencephalogram measurement apparatus 54 according to Embodiment 3.

FIG. 33 is a construction diagram of an electroencephalogram measurement apparatus 54 according to Embodiment 3. As compared to the electroencephalogram measurement apparatus 53 according to a variant of Embodiment 2, the noise estimation section 350 in the variant of Embodiment 2 is omitted from the electroencephalogram measurement apparatus 54 of the present embodiment. Moreover, a determination criteria setting section 480 is provided instead of the noise subtraction section 180, and a determination section 490 is provided instead of the determination section 390. Otherwise, the electroencephalogram measurement apparatus 54 of the present embodiment has an identical construction to the construction of the electroencephalogram measurement apparatus 53 according to the variant of Embodiment 2. The constituent elements surrounded by the broken line are similarly implementable by a CPU and/or a memory.

As in the above embodiment, the present embodiment also illustrates an example where a user's intent is acquired with an electroencephalogram interface using an event-related potential in order to control a device.

The determination criteria setting section 480 and the determination section 490 are implemented by a CPU and a memory, as are the noise subtraction section 180 and the determination section 390 of the electroencephalogram measurement apparatus 53 according to a variant of Embodiment 2.

As in Embodiment 2, Embodiment 3 illustrates an example where a user's intent is acquired with an electroencephalogram interface using an event-related potential in order to control a device. The present embodiment contemplates an HMD as shown in FIG. 6, and relies on the timing of highlighting an option on a display as a trigger for electroencephalogram cutting when acquiring an event-related potential.

The electroencephalogram measurement apparatus 54 includes an output control section 210, a waveform generation section 120, an electro-acoustic transducer 130, a band component analysis section 340, a determination criteria setting section 480, an image signal generation section 220, a display 230, an electrode section 160, a potential extraction section 170, a potential waveform cutting section 260, an electroencephalographical characteristic extraction section 270, and a determination section 490.

For the band-by-band components generated by the band component analysis section 340, the determination criteria setting section 480 sets determination criteria to be used when making an electroencephalogram determination.

The determination section 490 determines the user's intent from a characteristic amount in the electroencephalogram extracted by the electroencephalographical characteristic extraction section 270, according to the determination criterion having been set by the determination criteria setting section 480.

Figure 34:
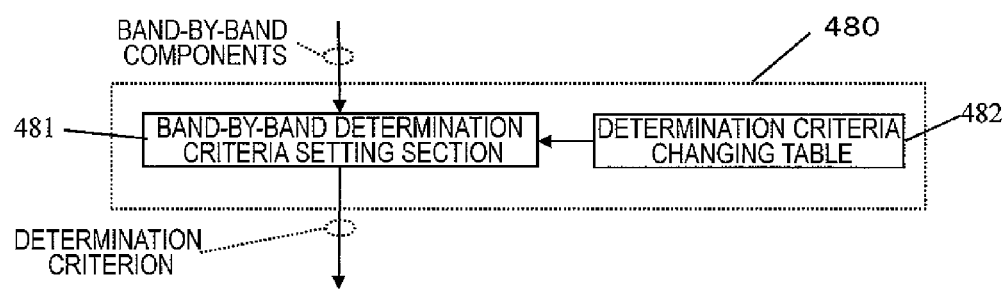
FIG. 34 is a diagram showing the details of a determination criteria setting section 480.

FIG. 34 shows the details of the determination criteria setting section 480. The determination criteria setting section 480 includes a band-by-band determination criteria setting section 481 and a determination criteria changing table 482.

Figure 35:
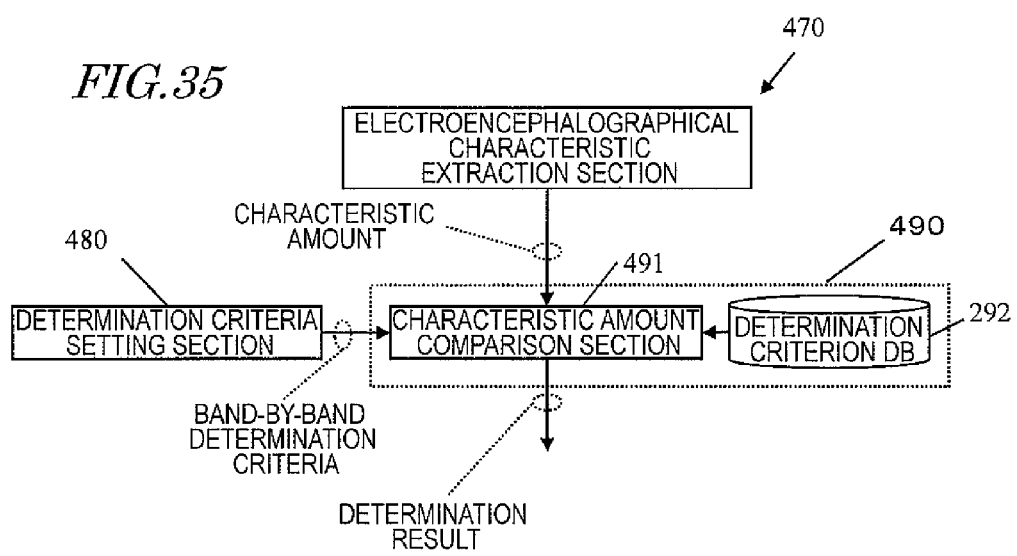
FIG. 35 is a diagram showing the details of a determination section 490.

FIG. 35 shows the details of the determination section 490. The determination section 490 includes a characteristic amount comparison section 491 and a determination criteria database 292. Note that the determination criteria database 292 is implemented by a memory.

The processing by the electroencephalogram measurement apparatus 54 will be described with reference to FIG. 36 below, thereby also describing the determination criteria setting section 480 and the determination section 490. In FIG. 33 to FIG. 35, portions which are identical to those in the variants of Embodiment 2 will be denoted by the same numerals, and the descriptions thereof will be omitted.

Figure 36:
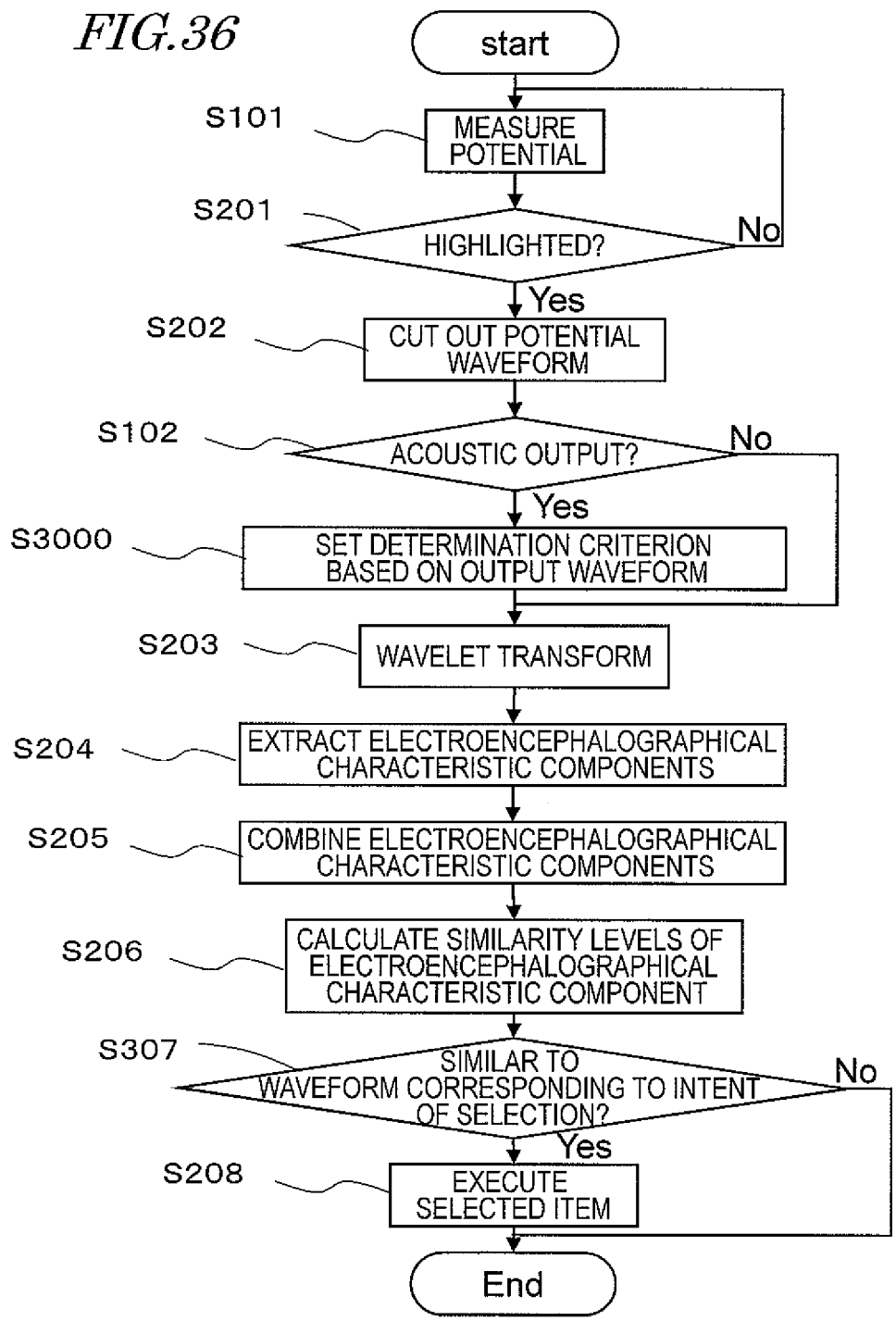
FIG. 36 is a flowchart showing a procedure of processing by the electroencephalogram measurement apparatus 54 of Embodiment 3.

FIG. 36 is a flowchart showing a procedure of processing by the electroencephalogram measurement apparatus of the present embodiment. Since it is similar to Embodiment 2 except that step S1000 is replaced by step S3000 and step S207 is replaced by step S307, descriptions of the other operations may be conveniently omitted.

If step S102 finds that there is an instruction for acoustic output, determination criteria are set based on the output waveform at step S3000. If step S102 finds that there is no instruction for acoustic output, determination criteria are not set because presumably the output waveform exerts no influence on the electroencephalogram.

Figure 37:
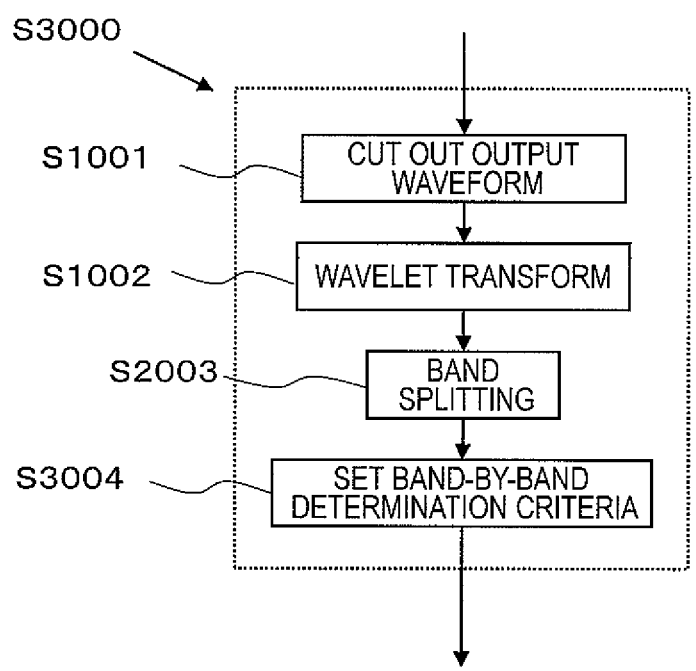
FIG. 37 is a flowchart showing a procedure of processing at step S3000 by the electroencephalogram measurement apparatus 54.

FIG. 37 is a flowchart showing a procedure of processing by the electroencephalogram measurement apparatus 54 at step S3000. Determination criteria are set through this process.

First, steps S1001 and S1002 are as described with respect to Embodiment 2.

On the other hand, at step S2003, the band component splitting section 343 splits the frequency-by-frequency components having been separated at step S1002 into bands. Specifically, the components may be split into the following six bands, for example: 0 Hz to 2 Hz; 2 Hz to 4 Hz; 4 Hz to 8 Hz; 8 Hz to 16 Hz; 16 Hz to 32 Hz; and 32 Hz or higher. The frequency components of an acoustic signal such as a voice or a piece of music change incessantly, even given the same human speaker or the same song, and therefore the electrical noise originating from the output waveform will also change incessantly.

FIG. 38 schematically shows an example of setting determination criteria based on the band components of the output waveform. The hatched portion(s) for each band in FIG. 38 schematically represents changes over time of each band component in a low-frequency region of the output waveform. The power of each frequency band in FIG. 38 is indicated in decibels, as a ratio to a reference value which is defined by an input limit value of 90 dB, for example. For example, the power may be classified into four classes, e.g., less than 10 dB; 10 dB or greater but less than 20 dB; 20 dB or greater but less than 30 dB; and 30 dB or greater. This number of classes will be later discussed in connection with the determination criteria changing table 482 (described later).

The power of each band respectively changes across the time axis. For example, in the band of 2 Hz or less in FIG. 38, there is a large power from 0 to 400 ms, but the power slightly decreases at 400 ms or later. Conversely, in the band from 16 Hz to 32 Hz, the power is not so large from 0 to near 450 ms, but increases near 450 ms and thereafter. When the electrical noise originating from the output waveform changes incessantly in accordance with such changes, there is a need to vary the determination criteria according to the noise situation in order to be able to correctly determine the acquired electroencephalogram.

At step S3004, the band-by-band determination criteria setting section 481 refers to the determination criteria changing table 482. Specifically, among the determination criteria which are adapted to a situation where the output waveform fluctuates over time in each frequency band, the band-by-band determination criteria setting section 481 looks up a determination criterion in a time-frequency range which contains the time-frequency range of an electroencephalographical component which is used in the electroencephalogram interface. For example, as shown in FIG. 38, a time-frequency range containing the time-frequency range of the electroencephalographical component P300, e.g., from 200 ms to 500 ms and at 4 Hz or less, is looked up in the present embodiment.

FIG. 39 shows an example of the determination criteria changing table 482. By using the determination criteria changing table 482, the band-by-band determination criteria setting section 481 sets a determination criterion that corresponds to the component power of each frequency band of the output waveform. As shown in FIG. 39, the power may be classified into the four classes of "less than 10 dB; 10 dB or greater but less than 20 dB; 20 dB or greater but less than 30 dB; and 30 dB or greater", and a lower limit of the similarity level to the correct waveform group and an upper limit of the similarity level to the incorrect waveform group may be set for each band.

In Embodiment 2, the threshold value of similarity level determination at step S207 is fixed. In the present embodiment, however, the threshold value of determination, which is defined by a combination of a similarity level to the correct waveform group and a similarity level to the incorrect waveform group, is to be set for each frequency band of the output waveform.

The table of thresholds values of determination illustrated in FIG. 39 above shows lower limits of the similarity level to the correct waveform group and upper limits of the similarity level to the incorrect waveform group. Furthermore, the threshold value of determination is set dynamically, so as to correspond to the power of each frequency band of the output waveform undergoing incessant changes in each band.

For example, given the changes over time in the power of each frequency band as shown in FIG. 38, there is a power of 30 dB or more in the band of 2 Hz or less, in the zone from 0 to 400 ms. Therefore, by referring to FIG. 39, any event-related potential that satisfies the condition that "the similarity level to the correct waveform group is 0.8 or more and yet the similarity level to the incorrect waveform group is 0.1 or less" is regarded as reflecting the user's intent of selection. For each band, a determination criterion is to be similarly set in accordance with the power of each time zone. Since different frequency bands and time zones are utilized for the determination of different event-related potentials, by providing a determination criterion for each band and each time zone, it becomes possible to cope with various event-related potentials.

In Embodiment 3, the band components of the output waveform are subjected to power and frequency classification as described above, and a determination criterion value is set by looking through the predetermined determination criterion values which are stored in the determination criteria changing table 482. However, the determination criterion value may be set by any other method, such as storing the frequency-power relationship as a mathematical function and setting a determination criterion value by using the mathematical function, so long as determination criteria are set in accordance with the band components of the output waveform.

The subsequent processes from steps S203 to S206 (FIG. 24) are generally the same as those of Embodiment 2 or its variants in principle, the difference being a part of the process of step S204.

At step S204, the characteristic component extraction section 272 cuts out only a region concerning the electroencephalographical characteristic signal from the result of wavelet transform at step S203. Specifically, the characteristic component extraction section 272 extracts data sampling points contained in the region from 200 ms to 400 ms and at frequencies of 4 Hz or less, in order to extract a characteristic feature of the P300 component, for example. Step S205 and the subsequent steps are identical to what was described in Embodiment 2.

At step S307, the characteristic amount comparison section 491 compares the similarity level to the correct waveform group and the similarity level to the incorrect waveform group determined at step S206. If the similarity level to the correct waveform group is greater than the similarity level to the incorrect waveform group and yet the similarity level to the correct waveform group is equal to or greater than the value determined at step S3004 and the similarity level to the incorrect waveform group is equal to or less than the value determined at step S3004, the characteristic amount comparison section 491 determines that the measured event-related potential represents an intent of selecting the highlighted item. The predetermined value may be 0.7 or more for the similarity level to the correct waveform group, and 0.3 or less for the similarity level to the incorrect waveform group, for example.

When the aforementioned condition is satisfied (following Yes from step S307), the output control section 210 executes the item at step S208 because the highlighted item is presumably the selected one. Specifically, the output control section 210 stops outputting the song that has so far been played back, and begins to play back a song that appears highlighted on the menu list, for example.

On the other hand, if step S307 finds that any of the aforementioned conditions is not satisfied, i.e., following No from step S307, the operation is ended.

In the present Embodiment 3, determination criteria are set across the entire time-frequency range at 32 Hz or less in step S3000. Alternatively, determination criteria may be set only in the time-frequency range corresponding to the electroencephalographical component to be used for determination, i.e., in the case of the present embodiment, 200 ms to 500 ms (corresponding to P300) and in the range of 4 Hz or less.

The electroencephalogram measurement apparatus 54 operating as above analyzes a waveform signal which is output from an electro-acoustic transducer that is in proximity to an electrode, and sets a determination criterion that takes into account its influence on the potential which is recorded at the electrode. As a result, even if the electrode and the electro-acoustic transducer are in proximity, without the influence from the acoustic output, an electroencephalogram can be measured for use in an electroencephalogram interface. Consequently, even if the electrode and the electro-acoustic transducer are disposed in proximity so as to fit within the range of a wearable device, it is possible to utilize an electroencephalogram interface. Since there is no need to wear any electrodes other than the wearable device itself, the user's burden associated with the wearing of devices can be reduced.

Variant of Embodiment 3

Next, a variant of the electroencephalogram measurement apparatus according to the above embodiment will be described.

Figure 40:
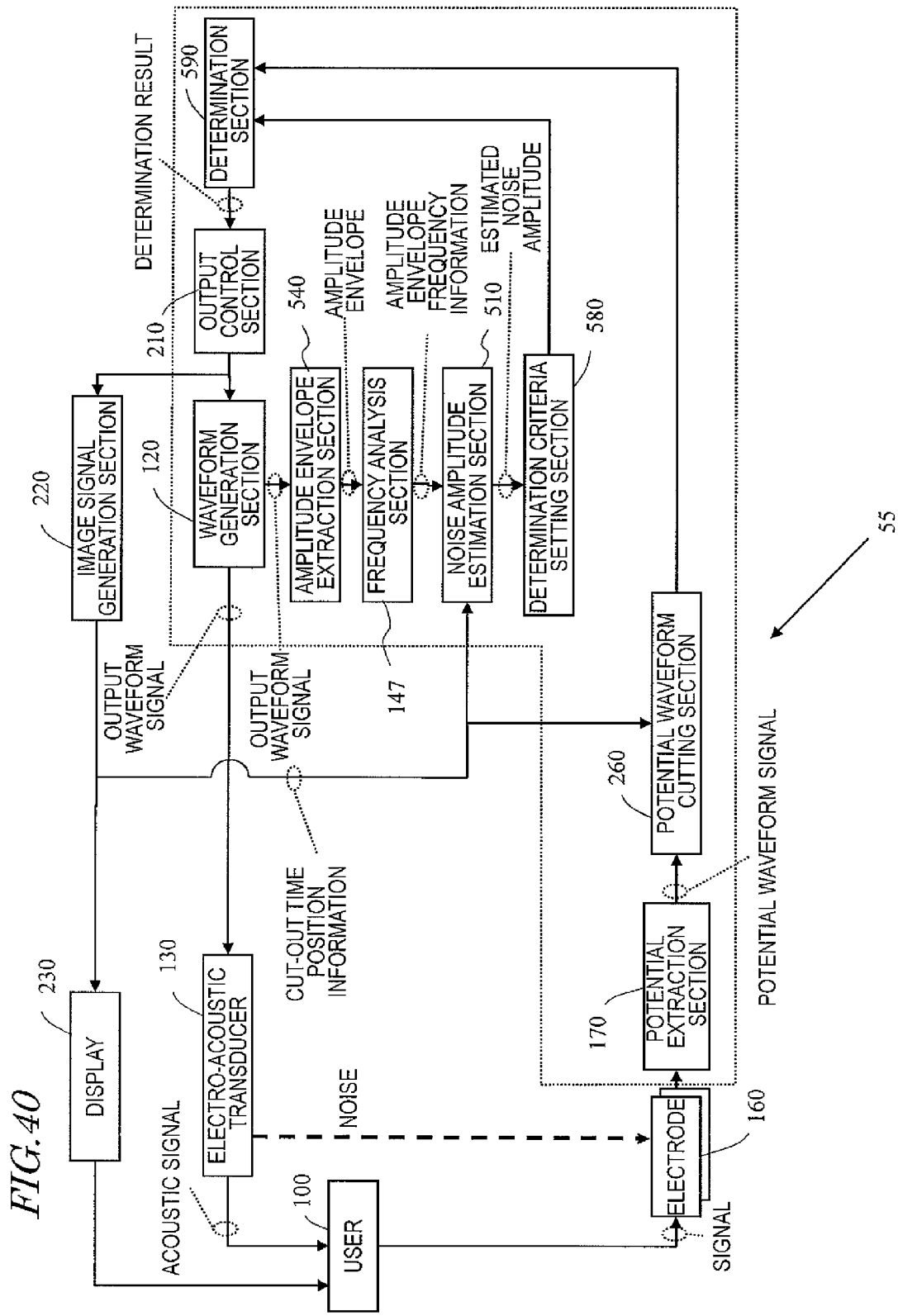
FIG. 40 is a construction diagram of an electroencephalogram measurement apparatus 55 according to a variant of Embodiment 3.

FIG. 40 is a construction diagram of an electroencephalogram measurement apparatus 55 according to a variant of the present embodiment.

As in Embodiment 3, this variant illustrates an example where a user's intent is acquired with an electroencephalogram interface using an event-related potential in order to control a device.

This example contemplates an HMD as shown in FIG. 6, and relies on the timing of highlighting an option on a display as a trigger for electroencephalogram cutting when acquiring an event-related potential.

The electroencephalographical characteristic extraction section 470 of Embodiment 3 is omitted from the electroencephalogram measurement apparatus 55 of this example. Moreover, an amplitude envelope extraction section 540, a frequency analysis section 147, and a noise amplitude calculation section 510 are provided instead of the band component analysis section 340; a determination criteria setting section 580 is provided instead of the determination criteria setting section 480; and a determination section 590 is provided instead of the determination section 490. Otherwise, the construction is the same.

The amplitude envelope extraction section 540, the noise amplitude calculation section 510, the determination criteria setting section 480, and the determination section 590 are implemented by a CPU and a memory. This is similar to the band component analysis section 340, determination criteria setting section 480, and the determination section 490 of Embodiment 3.

The electroencephalogram measurement apparatus 55 includes an output control section 210, a waveform generation section 120, an electro-acoustic transducer 130, an amplitude envelope extraction section 540, a frequency analysis section 147, a noise amplitude estimation section 510, a determination criteria setting section 580, an image signal generation section 220, a display 230, an electrode section 160, a potential extraction section 170, a potential waveform cutting section 260, and a determination section 590. As in the above-described embodiments, the constituent elements surrounded by the broken line are implementable by a CPU and/or a memory.

The amplitude envelope extraction section 540 is constructed by omitting the waveform cutting section 141 and the cut-out time position storage section 145 from the amplitude envelope extraction section 140 of Embodiment 1. The amplitude envelope extraction section 540 analyzes the waveform signal generated by the waveform generation section 120 to extract an amplitude envelope thereof.

The frequency analysis section 147 determines the frequency of the amplitude envelope which is extracted by the amplitude envelope extraction section 140.

In accordance with the frequency of the amplitude envelope determined by the frequency analysis section 147, the noise amplitude estimation section 510 calculates the amplitude of a noise waveform that is mixed in a potential that is measured by the electrode section 160, based on the low-frequency component waveform that is contained in the output acoustic signal having been extracted by the amplitude envelope extraction section 540.

Based on the amplitude level of the noise waveform that is calculated by the noise amplitude estimation section 510, the determination criteria setting section 580 sets determination criteria to be used when making an electroencephalogram determination.

Figure 41:
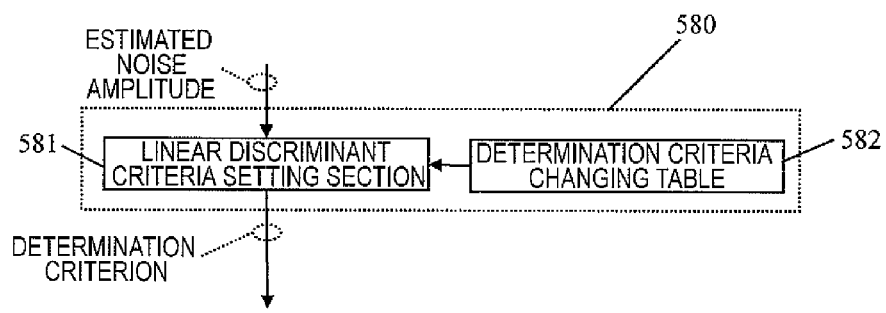
FIG. 41 is a diagram showing the detailed construction of a determination criteria setting section 580.

FIG. 41 shows the detailed construction of the determination criteria setting section 580.

The determination criteria setting section 580 includes a linear discriminant criteria setting section 581 and a determination criteria changing table 582.

In accordance with the determination criterion having been set by the determination criteria setting section 580, the determination section 590 determines the user's intent from the electroencephalogram waveform having been cut out by the potential waveform cutting section 260.

Figure 42:
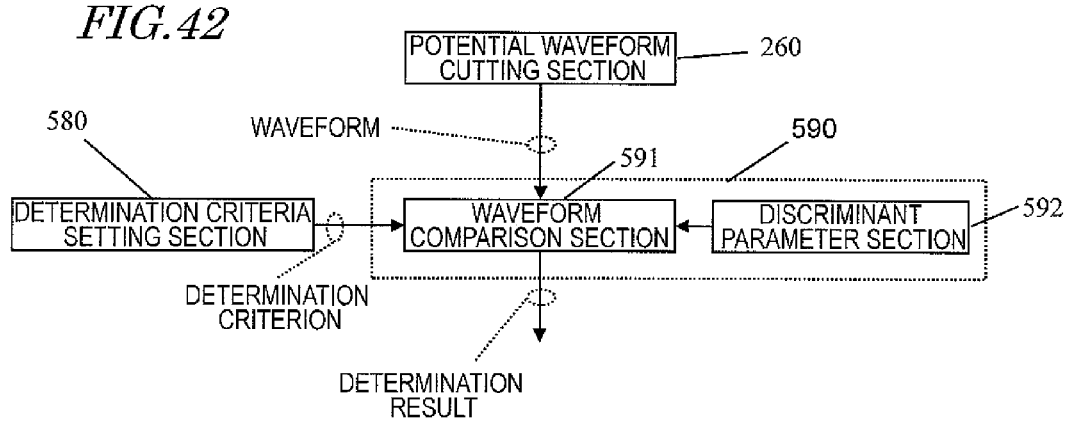
FIG. 42 is a diagram showing the detailed construction of a determination section 590.

FIG. 42 shows the detailed construction of the determination section 590.

The determination section 590 includes a waveform comparison section 591 and a discriminant parameter section 592. The discriminant parameter section 592 is implemented by a memory.

The processing by the electroencephalogram measurement apparatus 53 will be described with reference to FIG. 43 below, thereby also describing the determination criteria setting section 580 and the determination section 590. In FIG. 40 to FIG. 42, portions which are identical to those in Embodiment 3 will be denoted by the same numerals, and the descriptions thereof will be omitted.

Figure 43:
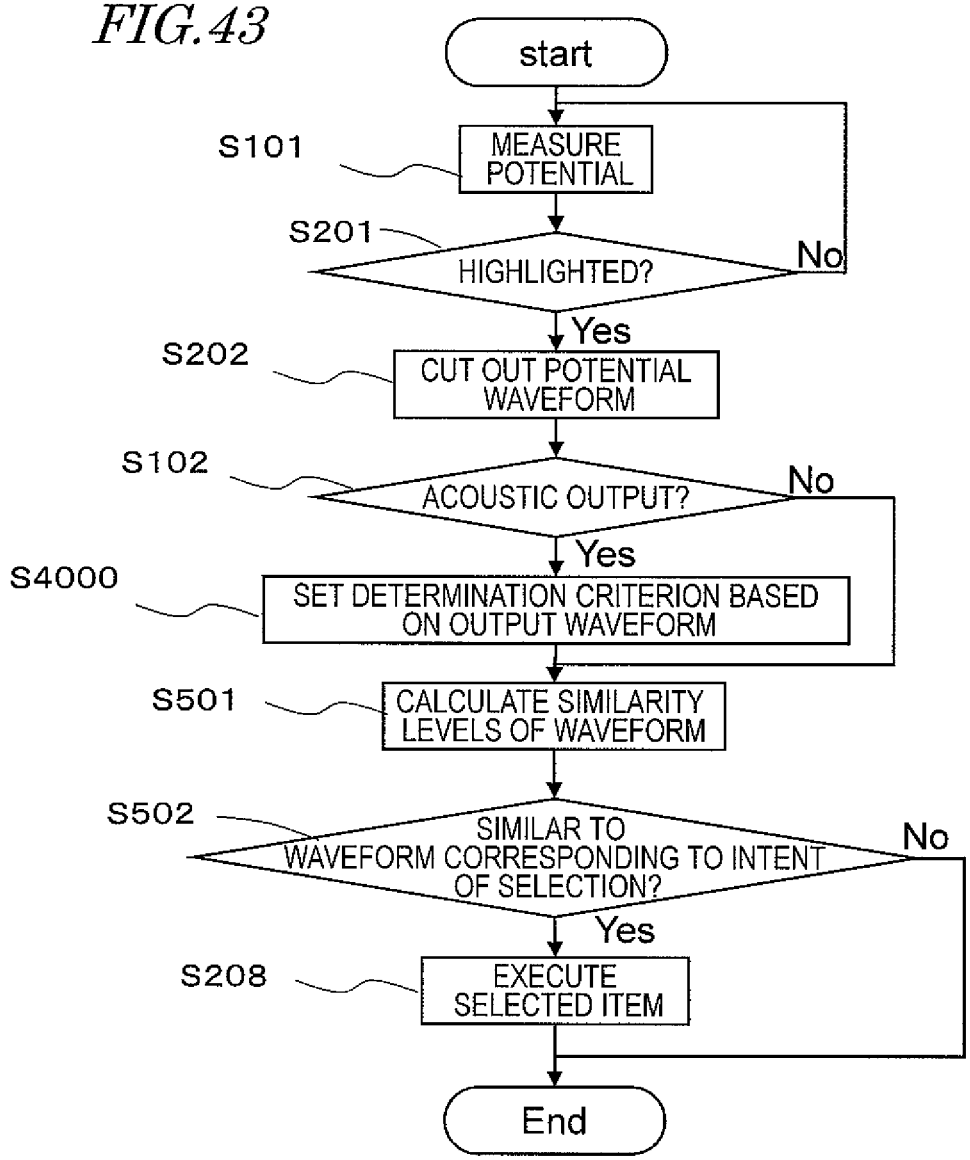
FIG. 43 is a flowchart showing a procedure of processing by an electroencephalogram measurement apparatus 54 according to a variant of Embodiment 3.

FIG. 43 is a flowchart showing a procedure of processing by the electroencephalogram measurement apparatus according to this variant of the present embodiment. Since it is similar to Embodiment 3 except that step S3000 in FIG. 36 is replaced by step S4000, steps S203 to S206 are replaced by step S501, and step S207 is replaced by step S502, descriptions of the other operations may be conveniently omitted.

If step S102 finds that there is an instruction for acoustic output, the determination criteria setting section 580 sets a determination criterion based on the output waveform at step S4000. The details of the determination criterion setting will be described later. If step S102 finds that there is no instruction for acoustic output, determination criteria are not set because presumably the output waveform exerts no influence on the electroencephalogram.

At step S501, the waveform comparison section 591 determines respective similarity levels between the waveform of the event-related potential having been cut out at step S202 and the correct waveform group and the incorrect waveform group. In this example, the waveform comparison section 591 checks the waveform data against a linear discriminant which is stored in the discriminant parameter section 592; as a result, discriminant scores are obtained, and similarity levels are calculated.

However, any other calculation method may be used; for example, previously recorded waveform data may be retained, and a distance may be obtained as a sum total of differences between individual waveforms.

The linear discriminant is derived as follows, for example. First, with respect to each of a plurality of event-related potentials corresponding to correct waveforms and incorrect waveforms which are measured in advance, the waveform comparison section 591 splits the range from 0 milliseconds to 600 milliseconds, based on the trigger as a base point in time, into zones each spanning 20 milliseconds. Then, the waveform comparison section 591 conducts a discriminant analysis, with the dependent variable being whether the discrimination indicates a correct waveform or an incorrect waveform, and the independent variables being mean potentials of the respective 20-millisecond zones. As a result, a linear discriminant can be obtained.

A discriminant which is derived through a discriminant analysis is to be utilized in such a manner that, by defining the degree of contribution which each independent variable makes to the discrimination as a weight, the independent variable of each data is multiplied with the weight for obtaining a total value. By checking one piece of data against the discriminant, a similarity level of the data in question can be calculated with respect to a group of data of each dependent variable, where the data used for generating the discriminant has been classified on the basis of dependent variables.

At step S502, the waveform comparison section 591 further checks the similarity levels calculated at step S501 against the determination criterion having been set at step S4000 to determine whether the measured event-related potential corresponds to an intent of selecting the highlighted item, corresponds to an intent of not selecting the highlighted item, or is indiscriminable.

If the result of determination of step S502 indicates that the measured event-related potential corresponds to an intent of selecting the highlighted item, the process proceeds to step S208. On the other hand, if it indicates that the measured event-related potential does not correspond to an intent of selecting the highlighted item or is indiscriminable, the operation is ended.

At step S208, the output control section 210 executes the item because the highlighted item is presumably the selected one.

Next, the process of the aforementioned step S4000 is described.

Figure 44:
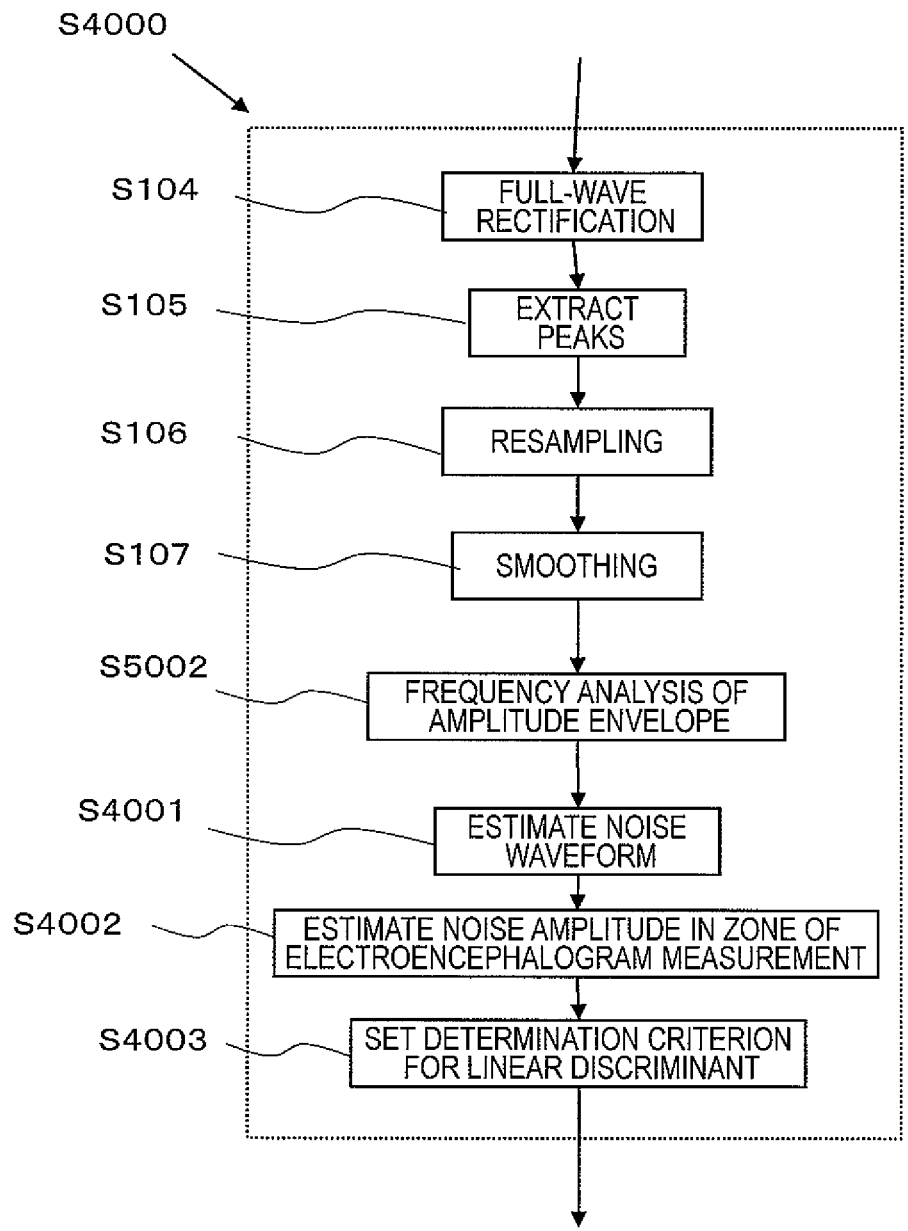
FIG. 44 is a flowchart showing a procedure of processing at step S4000 by the electroencephalogram measurement apparatus 55.

FIG. 44 is a flowchart showing a procedure of processing by the electroencephalogram measurement apparatus 55 at step S4000. A determination criterion is set through this process.

Steps S104 to S107 shown in FIG. 44 are identical to the corresponding processes in FIG. 15. These processes are carried out by the amplitude envelope extraction section 540, whereby a low-frequency component of the output signal is extracted.

At step S5002, the frequency analysis section 147 applies a frequency analysis to the amplitude envelope extracted at step S5001 as to its envelope profile. Since the details of steps S104 to S107 and S5002 have been described with reference to Embodiment 1, the descriptions thereof will be omitted.

At step S4001, in accordance with the frequency of the amplitude envelope determined at step S5002, the noise amplitude estimation section 510 estimates the amplitude of a noise that is superposed on the electroencephalogram measured by the electrode section 160, based on the low-range component generated at step S107. In accordance with a transform function shown in FIG. 16, the noise amplitude estimation section 510 determines a coefficient corresponding to the instantaneous frequency of the amplitude envelope determined at step S5002, and by multiplying each value of the low-frequency component by that coefficient, estimates the low-frequency electrical noise originating from the output waveform as a time waveform.

At step S4002, the noise amplitude estimation section 510 splits the noise waveform estimated at step S4001 by every predetermined time period (e.g., 1 second), and determines the maximum value and minimum value in each zone. A difference between them is defined as the noise amplitude in that zone. Based on a timing of highlighting which is output from the image signal generation section 220, the noise amplitude estimation section 510 determines the noise amplitude of a waveform which is output at a time corresponding to the time range of the potential waveform having been cut out at step S202, from the noise amplitude of each zone estimated from the output waveform signal.

At step S4003, by referring to the determination criteria changing table 582, the linear discriminant criteria setting section 581 sets a determination criterion in accordance with the noise amplitude in the zone of electroencephalogram measurement as estimated at step S4002. The determination criterion is to be used when making a determination as to the electroencephalogram waveform (which is an event-related potential in this example) by using a linear discriminant technique.

For example, when the noise increases and makes the electroencephalogram less clear, the determination criterion is set so that even a somewhat low similarity level to the correct waveforms will be determined as pertaining to a correct waveform, and that the upper limit of the similarity level to incorrect waveforms (i.e., those waveforms excluded from the correct waveforms) is increased in an attempt to capture more correct waveforms. On the other hand, when the noise is so large that it makes the electroencephalogram indiscriminable, determination is avoided altogether.

FIG. 45 shows an example of the determination criteria changing table 582 to be referred to by the linear discriminant criteria setting section 581. If the amplitude of the estimated noise is less than 1 microvolt, the usual determination criterion, i.e., an 80% or higher similarity level to correct waveforms and a 20% or lower similarity level to incorrect waveforms, is selected as the determination criterion. If the amplitude of the estimated noise is equal to or greater than 1 microvolt but less than 3 microvolts, a 70% or higher similarity level to correct waveforms and a 20% or lower similarity level to incorrect waveforms is selected as the determination criterion. If it is equal to or greater than 3 microvolts but less than 7 microvolts, a 70% or higher similarity level to correct waveforms and a 40% or lower similarity level to incorrect waveforms is selected as the determination criterion. If it is equal to or greater than 7 microvolts, no determination criterion is set, and determination is avoided altogether.

In this example, four different determination criteria are set depending on the noise amplitude, as shown in FIG. 45; however, this setting method is only an example. Any other method may be used, e.g., more or less than four different determination criteria may be set. Instead of a table, the determination criteria may be retained in the form of a similarity level determination function.

The electroencephalogram measurement apparatus 55 operating as above analyzes a waveform signal which is output from an electro-acoustic transducer that is in proximity to an electrode, and sets a determination criterion that takes into account its influence on the potential which is recorded at the electrode. As a result, even if the electrode and the electro-acoustic transducer are in proximity, without the influence from the acoustic output, an electroencephalogram can be measured for use in an electroencephalogram interface. Consequently, even if the electrode and the electro-acoustic transducer are disposed in proximity so as to fit within the range of a wearable device, it is possible to utilize an electroencephalogram interface. Since there is no need to wear any electrodes other than the wearable device itself, the user's burden associated with the wearing of devices can be reduced.

Embodiment 4

Figure 46:
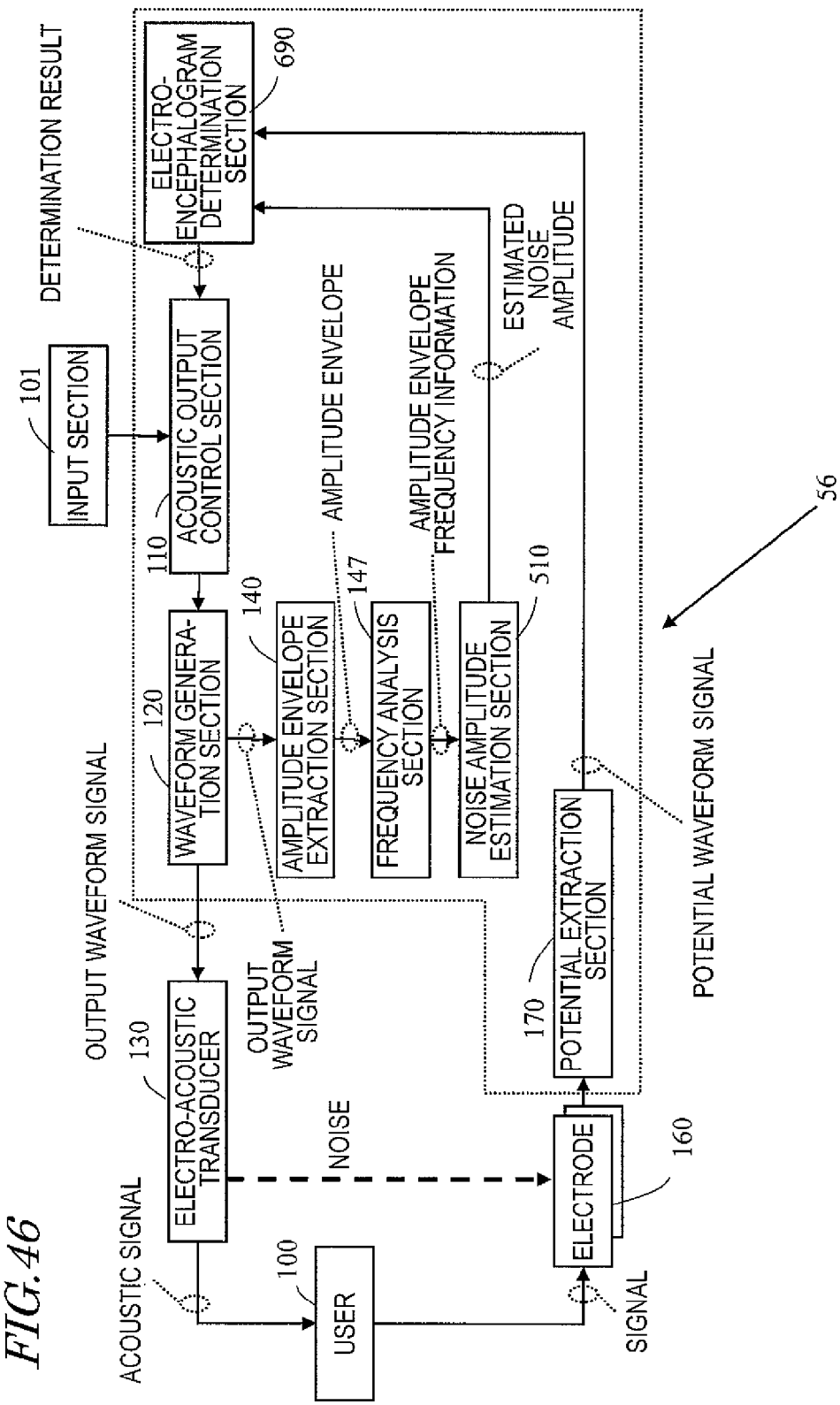
FIG. 46 is a construction diagram of an electroencephalogram measurement apparatus 56 according to Embodiment 4.

FIG. 46 is a construction diagram of an electroencephalogram measurement apparatus 56 according to the present embodiment. As compared to the electroencephalogram measurement apparatus 51 of Embodiment 1, the noise subtraction section 180 in the electroencephalogram measurement apparatus 51 of Embodiment 1 is omitted from the electroencephalogram measurement apparatus 56 of the present embodiment. Moreover, a noise amplitude estimation section 510 is provided instead of the noise estimation section 150, and an electroencephalogram determination section 690 is provided instead of the electroencephalogram determination section 190. Otherwise, the electroencephalogram measurement apparatus 56 of the present embodiment has an identical construction to the construction of the electroencephalogram measurement apparatus 51 according to Embodiment 1. Note that the constituent elements surrounded by the broken line may be implemented by a CPU and/or a memory.

Similarly to Embodiment 1, the present embodiment illustrates an example where user states are monitored based on an electroencephalogram, and a device is automatically controlled in accordance with changes in the electroencephalogram. More specifically, it is an example where the sound volume of an acoustic output is manipulated in accordance with the frequency of occurrence of α waves in the electroencephalogram. Applications to an HMD as shown in FIG. 6 or a hearing aid as shown in FIG. 7 are possible.

Firstly, the noise amplitude estimation section 510 and the electroencephalogram determination section 690 are implemented by a CPU and a memory, as are an acoustic output control section 110, a waveform generation section 120, an amplitude envelope extraction section 140, and a frequency analysis section 147.

The electroencephalogram measurement apparatus 56 includes an input means 101, the acoustic output control section 110, the waveform generation section 120, an electro-acoustic transducer 130, the amplitude envelope extraction section 140, the frequency analysis section 147, the noise amplitude estimation section 510, an electrode section 160, a potential extraction section 170, and the electroencephalogram determination section 690.

In accordance with the frequency of the amplitude envelope determined by the frequency analysis section 147, the noise amplitude estimation section 510 estimates the amplitude of an electrical noise which is caused by a low-frequency component, i.e., amplitude envelope, extracted by the amplitude envelope extraction section 140.

Based on the amplitude of the noise estimated by the noise amplitude estimation section 510, the electroencephalogram determination section 690 sets a determination criterion, and determines a frequency of occurrence of α waves contained in the waveform of potential changes extracted by the potential extraction section 170.

Figure 47:
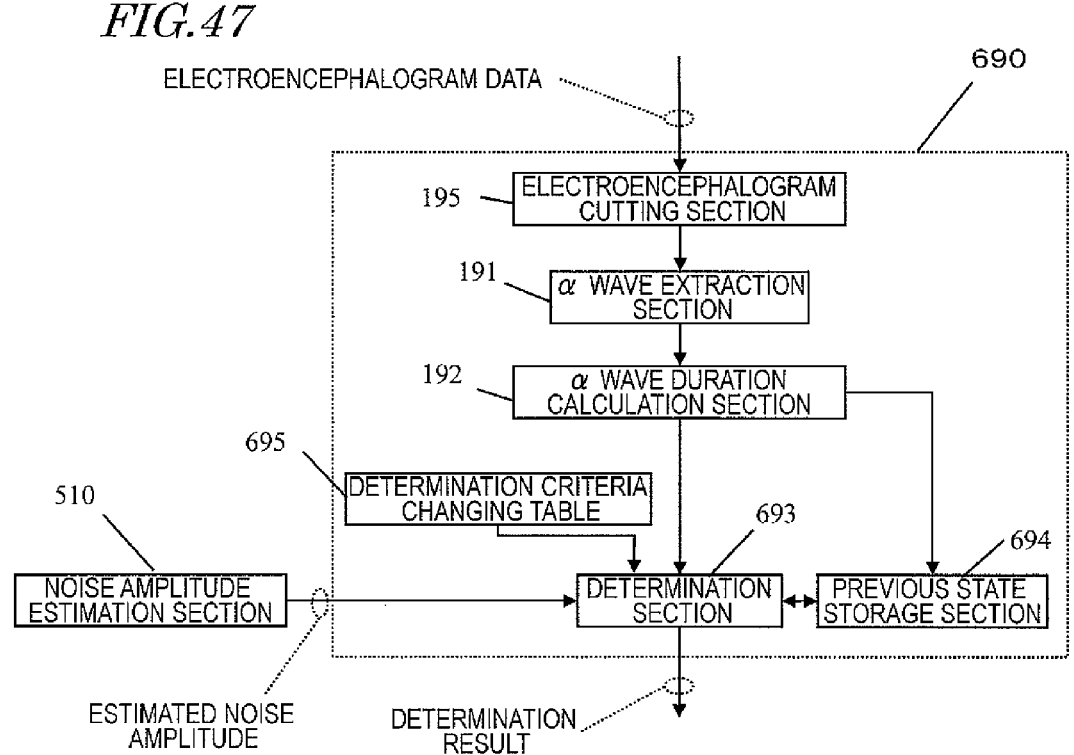
FIG. 47 is a diagram showing the detailed construction of an electroencephalogram determination section 690.

FIG. 47 shows the detailed construction of the electroencephalogram determination section 690. The electroencephalogram determination section 690 includes an electroencephalogram cutting section 195, an α wave extraction section 191, an α wave duration calculation section 192, a determination section 693, a previous state storage section 694, and a determination criteria changing table 695.

In FIG. 46 and FIG. 47, portions which are identical to those in Embodiment 1 will be denoted by the same numerals, and the descriptions thereof will be omitted.

Figure 48:
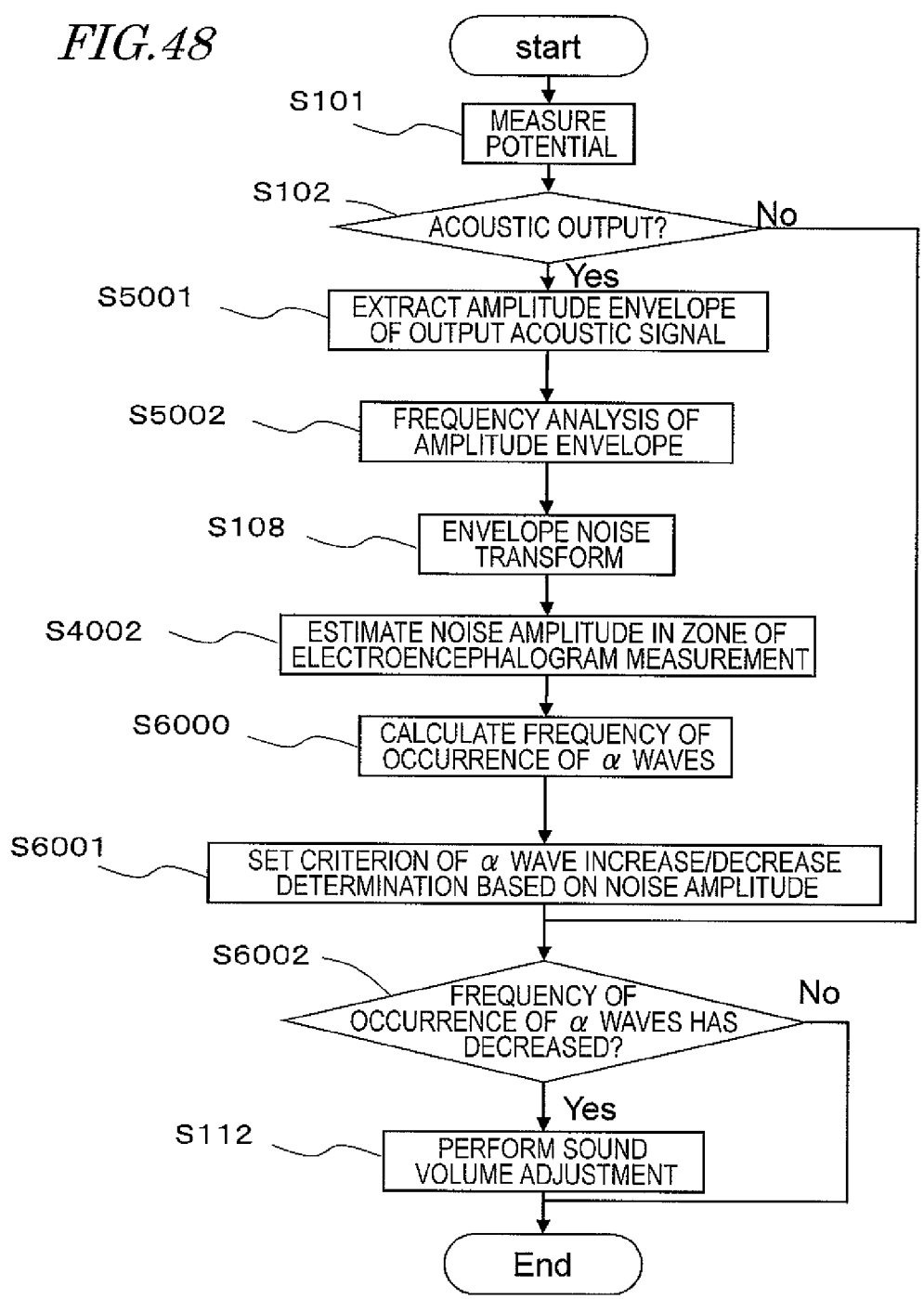
FIG. 48 is a flowchart showing a procedure of processing by the electroencephalogram measurement apparatus 56 according to Embodiment 4.

FIG. 48 is a flowchart showing a procedure of processing by the electroencephalogram measurement apparatus 56 according to the present embodiment. It is similar to Embodiment 1 except that step S5003 in FIG. 14 is replaced by steps S6000 and S6001; step S111 is replaced by step S6002; and S4002 is added; therefore, descriptions of the other operations may be conveniently omitted.

If step S102 finds that an instruction for acoustic output is being issued (following Yes from step S102), the process proceeds to step S5001; if an instruction for acoustic output is not being issued (following No from step S102), the process proceeds to step S6002.

At step S5001, an amplitude envelope is extracted as a low-frequency component, and an instantaneous frequency of the amplitude envelope is analyzed at step S5002. At step S108, a coefficient corresponding to the instantaneous frequency of the envelope, i.e., low-range component. Then at step S4002, as has been described with respect to a variant of Embodiment 3, a noise amplitude is estimated in the zone of electroencephalogram measurement.

At step S6000, the electroencephalogram cutting section 195 cuts out an electroencephalogram waveform spanning a predetermined duration, and the α wave extraction section 191 extracts α waves which are recorded in the electroencephalogram having been cut out by the electroencephalogram cutting section 195. The α wave duration calculation section 192 determines a total duration of the α waves observed within the waveform having been cut out. At step S6001, in accordance with the amplitude of the noise estimated at step S4002, the determination section 193 sets a criterion of alpha wave increase/decrease determination based on a look-up table between noise amplitudes and determination criteria. If No at step S102, control proceeds to step S6002.

FIG. 49 shows an example of the look-up table between noise amplitudes and determination criteria. The processes related to FIG. 49 will be described later.

At step S6002, the electroencephalogram determination section 190 compares the total duration of α waves calculated at step S6001 against the total duration of past α waves that is stored in the previous state storage section 694. Thus, it is determined whether the frequency of occurrence of α waves has decreased or not.

If step S102 finds that there is no instruction for acoustic output, i.e., following No from step S102, the waveform is treated on the assumption that no noise is mixed in the potential difference acquired at step S101. In other words, a predetermined criterion for the case of no noise is used as the determination criterion for determining a decrease in α waves.

Step S112 is a similar process to the process of sound volume adjustment described in Embodiment 1. If the frequency of occurrence of α waves has decreased at step S6002, i.e., following Yes from step S6002, the acoustic output control section 110 decreases the sound volume of the acoustic output (step S112). If step S6002 finds that the frequency of occurrence of α waves has not decreased, i.e., following No from S6002, the acoustic output control section 110 makes no change in the acoustic output.

Now, the method of setting a criterion of α wave increase/decrease determination at step S6001 will be described in detail.

The determination section 193 compares the amplitude value of the noise estimated at step S4002 by the noise amplitude estimation section 510 against a past noise that is stored in the previous state storage section 694. The determination section 193 refers to the determination criteria changing table 695 for the difference between the current noise amplitude and the past noise amplitude, and acquires a rate of change in the criterion shown in FIG. 49, for example.

It is assumed for instance that the current noise amplitude is 3 microvolts and the past noise amplitude stored in the previous state storage section 694 is 1 microvolt, i.e., there is currently an increase of 2 microvolts from the past. In the look-up table of FIG. 49, this information corresponds to the noise amplitude being 5 microvolts or less ("~5 μV" in FIG. 49) and the amount of increase in noise amplitude being between 1 microvolt and 3 microvolts.

Thus, the increase/decrease determination of α waves is adjusted as follows: relative to the predetermined determination criterion for the case of no noise, a difference in duration for recognizing that the total duration of current α waves is longer than that of the past is increased by 20%; and a difference in duration for recognizing that the total duration of current α waves is shorter than that of the past is increased by 10%.

For example, assuming that the difference in total duration for recognizing an increase is 100 milliseconds and the difference in total duration for recognizing a decrease is 50 milliseconds under the normal setting for the no-noise case, if the current noise amplitude is 3 microvolts and the past noise amplitude stored in the previous state storage section 694 is 1 microvolt, then the frequency of occurrence of alpha waves will be determined to have increased when the total duration is 120 milliseconds longer, and the frequency of occurrence of α waves will be determined to have decreased when the total duration is 55 milliseconds shorter.

Although the present embodiment illustrates manipulation of the sound volume of an acoustic output based on the frequency of occurrence of α waves, any other manipulation may also be controlled, e.g., turning off of the power switch, switching between modes, or the like. In the case of a hearing aid, in particular, a manipulation of automatically switching between a mode for concentrating on conversations, a mode for allocating casual attention to the crowd noise, and the like may be made on the basis of an electroencephalogram.

The electroencephalogram measurement apparatus 56 operating as above analyzes a waveform signal which is output from an electro-acoustic transducer that is in proximity to an electrode, estimates the amplitude of a low-frequency electrical noise which is mixed in the potential that is recorded at the electrode, and adaptively changes the determination criterion. As a result, even if the electrode and the electro-acoustic transducer are in proximity, while reducing the influence from the acoustic output, it is possible to monitor user states, such as emotions, drowsiness, etc., via electroencephalogram measurement.

According to the conventional principles, when a low-frequency band electrical noise originating from the acoustic output is mixed, the α waves, which is the characteristic electroencephalographical component for use as an index, cannot be separated from the noise. Although this actually makes α waves unavailable, the noise will be misdetected as α waves at step S111, so that changes in the frequency of occurrence of α waves cannot be accurately grasped. Therefore, sound volume adjustment will not be correctly performed in the example of the present embodiment.

In contrast, the construction of the present embodiment enables an electroencephalogram determination which takes into account the noise influences. Therefore, even if an electrode and an electro-acoustic transducer are disposed in proximity so as to fit within the range of a wearable device, it is possible to monitor user states based on an electroencephalogram. Since there is no need to wear any electrodes other than the wearable device itself, the user's burden associated with the wearing of devices can be reduced.

Although the present embodiment illustrates that the frequency of occurrence of α waves is employed for the monitoring of user states, an index based on any other electroencephalographical component may also be employed, e.g., a power ratio between α waves and β waves.

An electroencephalogram measurement apparatus according to the present invention is widely applicable to the case where an electro-acoustic transducer is in proximity to an electrode for electroencephalogram measurement. It is applicable to various apparatuses which include acoustic output means and which allows an electroencephalogram to be measured in a range of contact with the skin in the ear periphery, e.g., HMDs, music players, and hearing aids. For example, it is useful for constructing an electroencephalogram monitoring apparatus for monitoring user states, or an electroencephalogram interface system which realizes device manipulations or the like by utilizing an electroencephalogram. It is also available for applications such as wearable information devices and communications devices such as mobile phones.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An electroencephalogram measurement apparatus comprising:
    an electroencephalogram measurement unit for measuring an electroencephalogram of a user by using a plurality of electrodes;
    an electro-acoustic transducer for presenting an acoustic signal to the user, the electro-acoustic transducer being in a vicinity of at least one electrode among the plurality of electrodes while the electroencephalogram measurement unit is worn by the user;
    an amplitude envelope extraction unit for extracting an amplitude envelope of the acoustic signal presented by the electro-acoustic transducer;
    a frequency analysis unit for analysing a frequency of the amplitude envelope extracted by the amplitude envelope extraction unit; and
    a noise estimation unit for estimating an electrical noise which originates from the electro-acoustic transducer and is mixed at the at least one electrode by using a previously provided set of transform rules and the frequency of the extracted amplitude envelope analyzed by the frequency analysis unit.

2. The electroencephalogram measurement apparatus of claim 1, wherein,
    the set of transform rules defines correspondence between frequencies of amplitude envelope and transform coefficients; and
    the noise estimation unit estimates the electrical noise by using an instantaneous frequency of the amplitude envelope and the set of transform rules to determine a transform coefficient corresponding to the instantaneous frequency, and multiplying the amplitude envelope by the determined transform coefficient.

3. The electroencephalogram measurement apparatus of claim 2, wherein the noise estimation unit estimates the electrical noise by using a set of transform rules which defines smaller transform coefficients for larger frequencies.

4. The electroencephalogram measurement apparatus of claim 2, wherein the noise estimation unit estimates the electrical noise by using a set of transform rules such that the transform coefficient converges to zero between frequencies of 20 Hz and 30 Hz.

5. The electroencephalogram measurement apparatus of claim 1, further comprising a reduction unit for removing the estimated electrical noise from the electroencephalogram.

6. The electroencephalogram measurement apparatus of claim 1, wherein,
    the set of transform rules is a previously provided transform function; and
    the noise estimation unit determines a transform coefficient relating to a noise estimate value from the frequency of the extracted amplitude envelope according to the previously provided transform function, and, based on the transform coefficient, estimates a noise which originates from the electro-acoustic transducer due to the amplitude envelope and is electrically mixed into an input signal at the at least one electrode.

7. The electroencephalogram measurement apparatus of claim 6, further comprising a reduction unit for removing the estimated electrical noise from the electroencephalogram.

8. The electroencephalogram measurement apparatus of claim 6, wherein the transform function is a mathematical function defining a transform coefficient such that the transform coefficient becomes smaller for higher frequencies, and converges to zero between frequencies of 20 Hz and 30 Hz of a component contained in the presented acoustic signal.

9. The electroencephalogram measurement apparatus of claim 8, wherein the transform function defines mapping of transform coefficients onto a predetermined plurality of bands.

10. The electroencephalogram measurement apparatus of claim 6, wherein the amplitude envelope extraction unit extracts the amplitude envelope of the acoustic signal by applying a time-frequency separation to the acoustic signal through a wavelet transform.

11. The electroencephalogram measurement apparatus of claim 6, wherein the amplitude envelope extraction unit extracts the amplitude envelope of the acoustic signal by applying a time-frequency separation to the acoustic signal through the Fourier transform.

12. The electroencephalogram measurement apparatus of claim 6, wherein, among components which are obtained by applying a time-frequency separation to the acoustic signal, the amplitude envelope extraction unit extracts a frequency component that is equal to or less than a predetermined upper-limit frequency between 20 Hz and 30 Hz as the amplitude envelope of the acoustic signal.

13. The electroencephalogram measurement apparatus of claim 6, wherein the amplitude envelope extraction unit determines from the acoustic signal a frequency component of a time-frequency domain by applying a wavelet transform for a frequency band containing a predetermined electroencephalogram frequency and a predetermined time zone, and extracts and outputs the amplitude envelope of the acoustic signal by applying an inverse wavelet transform to the determined frequency component of the time-frequency domain.

14. The electroencephalogram measurement apparatus of claim 8, wherein the noise estimation unit uses the transform function to determine a transform coefficient corresponding to a frequency component contained in the acoustic signal.

15. The electroencephalogram measurement apparatus of claim 14, further comprising a storage unit for storing the transform function.

16. The electroencephalogram measurement apparatus of claim 1, wherein the at least one electrode is integral with the electro-acoustic transducer.

17. An electroencephalogram measurement apparatus for determining an intent of a user from a measured electroencephalogram according to a previously provided determination criterion, comprising:
    an electroencephalogram measurement unit for measuring an electroencephalogram of the user by using a plurality of electrodes;
    an electro-acoustic transducer for presenting an acoustic signal to the user, the electro-acoustic transducer being in a vicinity of at least one electrode among the plurality of electrodes while the electroencephalogram measurement unit is worn by the user;

an amplitude envelope extraction unit for extracting an amplitude envelope of the acoustic signal presented by the electro-acoustic transducer;

a frequency analysis unit for analyzing a frequency of the amplitude envelope extracted by the amplitude envelope extraction unit;

a noise estimation unit for estimating an electrical noise which originates from the electro-acoustic transducer and is mixed at the at least one electrode by using a previously provided set of transform rules and the frequency of the extracted amplitude envelope analyzed by the frequency analysis unit; and a determination criteria setting unit for changing the determination criterion in accordance with the estimated noise.

18. The electroencephalogram measurement apparatus of claim 17, wherein,
the set of transform rules is a previously provided transform function; and
the noise estimation unit determines a transform coefficient relating to a noise estimate value from the frequency of the extracted amplitude envelope according to the previously provided transform function, and, based on the transform coefficient, estimates a noise which originates from the electro-acoustic transducer due to the amplitude envelope and is electrically mixed into an input signal at the at least one electrode.

19. The electroencephalogram measurement apparatus of claim 18, wherein the amplitude envelope extraction unit extracts the amplitude envelope of the acoustic signal by applying a time-frequency separation to the acoustic signal through a wavelet transform.

20. The electroencephalogram measurement apparatus of claim 18, wherein the amplitude envelope extraction unit extracts the amplitude envelope of the acoustic signal by applying a time-frequency separation to the acoustic signal through the Fourier transform.

21. The electroencephalogram measurement apparatus of claim 18, wherein, among components which are obtained by applying a time-frequency separation to the acoustic signal, the amplitude envelope extraction unit extracts a frequency component that is equal to or less than a predetermined upper-limit frequency between 20 Hz and 30 Hz as the amplitude envelope of the acoustic signal.

22. The electroencephalogram measurement apparatus of claim 18, wherein the amplitude envelope extraction unit determines from the acoustic signal a frequency component of a time-frequency domain by applying a wavelet transform for a frequency band containing a predetermined electroencephalogram frequency and a predetermined time zone, and extracts and outputs the amplitude envelope of the acoustic signal by applying an inverse wavelet transform to the determined frequency component of the time-frequency domain.

23. The electroencephalogram measurement apparatus of claim 17, wherein the determination criterion is a criterion to be used for determining an intent of the user based on similarity levels between the measured electroencephalogram and a plurality of pieces of reference electroencephalogram data, and comprises a threshold value or a combination of a plurality of threshold values for the similarity levels.

24. The electroencephalogram measurement apparatus of claim 17, wherein the at least one electrode is integral with the electro-acoustic transducer.

25. A method of estimating an electrical noise, the method comprising the steps of:
measuring an electroencephalogram of a user with an electroencephalogram measurement unit by using a plurality of electrodes;
presenting an acoustic signal to the user by using an electro-acoustic transducer which is in a vicinity of at least one electrode among the plurality of electrodes while the electroencephalogram measurement unit is worn by the user;
extracting an amplitude envelope of the acoustic signal presented by the electro-acoustic transducer with an amplitude envelope extraction unit;
analysing a frequency of the amplitude envelope with a frequency analysis unit;
with a noise estimation unit, estimating an electrical noise which originates from the electro-acoustic transducer and is mixed at the at least one electrode by using a previously provided set of transform rules and the frequency of the extracted amplitude envelope; and
removing the estimated electrical noise from the electroencephalogram with a reducing unit.

26. A non-transitory computer-readable medium storing a computer program; to be executed by a computer mounted in an electroencephalogram measurement apparatus, wherein the computer program causes the computer to execute the steps of:
receiving data of an electroencephalogram of a user measured with an electroencephalogram measurement unit by using a plurality of electrodes;
presenting an acoustic signal to the user by using an electro-acoustic transducer which is in a vicinity of at least one electrode among the plurality of electrodes while the electroencephalogram measurement unit is worn by the user;
extracting an amplitude envelope of the acoustic signal presented by the electro-acoustic transducer;
analysing a frequency of the amplitude envelope; and
estimating an electrical noise which originates from the electro-acoustic transducer and is mixed at the at least one electrode by using a previously provided set of transform rules and the frequency of the extracted amplitude envelope.

\* \* \* \* \*